United States Patent
Connell et al.

(10) Patent No.: US 10,912,761 B2
(45) Date of Patent: Feb. 9, 2021

(54) METHODS AND COMPOSITIONS INVOLVING RAD51 INHIBITORS

(71) Applicant: The University of Chicago, Chicago, IL (US)

(72) Inventors: Philip P. Connell, Chicago, IL (US); Brian Budke, Chicago, IL (US); Jay H. Kalin, Chicago, IL (US); Michal Pawlowski, Chicago, IL (US); Alan P. Kozikowski, Chicago, IL (US)

(73) Assignee: THE UNIVERSITY OF CHICAGO, Chicago, IL (US)

( * ) Notice: Subject to any disclaimer, the term of this patent is extended or adjusted under 35 U.S.C. 154(b) by 18 days.

(21) Appl. No.: 14/648,115

(22) PCT Filed: Nov. 27, 2013

(86) PCT No.: PCT/US2013/072172
§ 371 (c)(1),
(2) Date: May 28, 2015

(87) PCT Pub. No.: WO2014/085545
PCT Pub. Date: Jun. 5, 2014

(65) Prior Publication Data
US 2015/0306069 A1    Oct. 29, 2015

Related U.S. Application Data

(60) Provisional application No. 61/731,982, filed on Nov. 30, 2012.

(51) Int. Cl.
*A61K 31/496* (2006.01)
*A61K 31/5377* (2006.01)
(Continued)

(52) U.S. Cl.
CPC .......... *A61K 31/402* (2013.01); *A61K 31/496* (2013.01); *A61K 31/5377* (2013.01); *C07D 207/456* (2013.01)

(58) Field of Classification Search
CPC .............. A61K 31/402; A61K 31/5377; A61K 31/496; C07D 207/456
See application file for complete search history.

(56) References Cited

U.S. PATENT DOCUMENTS

2003/0229004 A1    12/2003  Zarling et al. ................... 514/1

FOREIGN PATENT DOCUMENTS

| EP | 1 731 609 | 12/2006 |
| WO | WO 1995/30646 | 11/1995 |

(Continued)

OTHER PUBLICATIONS

Danziger et al., Automated Site-directed Drug Design: A General Algorithm for Knowledge Acquisition about Hydrogen-Bonding Regions at Protein Surfaces, Mar. 22, 1989, the Royal Society, Proceedings of the Royal Society of London.Series B, Biological Sciences, vol. 236, No. 1283, p. 101-113.*

(Continued)

*Primary Examiner* — Savitha M Rao
*Assistant Examiner* — Andrew P Lee
(74) *Attorney, Agent, or Firm* — Norton Rose Fulbright US LLP

(57) ABSTRACT

The present invention concerns methods and compositions involving inhibitors and of RAD51, a protein involved in homologous recombination. In some embodiments, there are methods for sensitizing cells to the effects of DNA damaging agents, which can have particular applications for cancer patients. In some embodiments of the invention, the RAD51 inhibitor is a small molecule that directly affects RAD51 activity, such as its ability to promote filament formation.

20 Claims, 15 Drawing Sheets

(51) Int. Cl.
C07D 207/456 (2006.01)
A61K 31/402 (2006.01)

(56) References Cited

FOREIGN PATENT DOCUMENTS

| WO | WO 2003/013488 | 2/2003 |
|---|---|---|
| WO | WO 2004/097426 | 11/2004 |
| WO | WO 2007/120726 | 10/2007 |
| WO | WO 2008/067863 | 6/2008 |
| WO | WO 2008/157003 | 12/2008 |
| WO | WO 2009/018219 | 2/2009 |
| WO | WO 2009/042270 | 4/2009 |
| WO | WO 2009/154828 | 12/2009 |

OTHER PUBLICATIONS

Patani, Bioisosterism: A Rational Approach in Drug Design, Chem. Rev. 1996, 96, pp. 3147-3176 (Year: 1996).*
McKenna, Persistent DNA damage caused by low levels of mitomycin C induces irreversible cell senescence, Cell Cycle, 2012 11(16), pp. 3132-3140 (Year: 2012).*
Alda et al., Clin. Cancer Res., 4:235-240, 1998.
Bello et al., Biochem. Pharmacal., 63:1585-1588,2002.
Bennardo, et al., PLoS Genet., 4:e1000110, 2008.
Chen et al., J Biol. Chem., 274:32931-32935, 1999.
Chen et al., Proc. Nat!. Acad. Sci. USA, 95:5287-5292, 1998.
Davies et al., Mol. Cell, 7:273-282, 2001.
Esashi et al., Nature, 434:598-604, 2005.
Han et al., Cancer Res., 62:2890-2896, 2002.
Hansen et al., Int. J Cancer, 105:472-479, 2003.
Henning and Sturzbecher, Toxicology, 193:91-109, 2003.
Hine, et al., Proc. Nat. Acad. Sci., 105:20810-20815, 2008.
Ito et al., J Gene Med., 7(8):1044-1052, 2005.
Klein, H., DNA Repair, 7:686-693, 2008.
Maacke et al., Int. J Cancer, 88:907-913, 2000a.
Maacke et al., J Cancer Res. Clin. Oncol., 128:219-222, 2002.
Maacke et al., Oncogene, 19:2791-2795, 2000b.
Mansour, et al. Nucleic Acids Res., 36: 4088-4098, 2008.
Marcus et. al., Cancer, 77(4):697-670, 1996.
Moynahan et al., Mol. Cell, 7:263-272, 2001.
Pellegrini et al., Nature, 420:287-293, 2002.
Porter et al., Br. J Surg., 81:1512-1515, 1994.
Qiao et al., Br. J Cancer, 93:137-143,2005.
Raderschall et al., Cancer Res., 62:219-225, 2002.
Rubin et al., N Engl. J Med., 335:1413-1416, 1996.
Russell et al., Cancer Res., 63:7377-7383, 2003.
Shin et al., Embo. J., 22:4566-4576, 2003.
Slupianek et al., Mol. Cell, 8:795-806, 2001.
Stark, et al., Mol. Cell Biol., 24:9305-9316,2004.
Takata et al., Mol. Cell Biol., 21:2858-2866, 2001.
Vispe et al., Nucleic Acids Res., 26:2859-2864, 1998.
Wong et al., J Biol. Chem., 272:31941-31944, 1997.
Yoshikawa et al., 2000.
Yuan et al., Cancer Res., 59:3547-3551, 1999.
Bishop et al., "Xrcc3 is required for assembly of Rad51 complexes in vivo," J. Biol. Chem., 273:21482-21488, 1998.
Budke, B et al. R1-1: A Chemical Inhibitor of RAD51 That Disrupts Homologous Recombination in Human Cells. Nucleic Acids Research. May 9, 2012, vol. 40; pp. 7347-7357; p. 7349, right column, fourth paragraph to p. 7350, left column, first paragraph; p. 7350, figure 2A. DOI: 10.1093/nar/gks353.
Burgeev et al., Ca2+ activates human homologous recombination protein Rad51 by modulating its ATPase activity, PNAS, 101(27):9988-9993, 2004.
Caldecott and Jeggo, "Cross-sensitivity of gamma-ray-sensitive hamster mutants to crosslinking agents," Mutat. Res., 255:111-121, 1991.

Chen et al., "Expression of BRC repeats in breast cancer cells disrupts the BRCA2-RAD51 complex and leads to radiatoin hypersensitivity and loss of G2/M checkpoint control," J. Biol. Chem., 274(46):32931-32935, 1999.
Chen et al., "The BRC repeats in BRCA2 are critical for RAD51 binding and resistance to methyl methanesulfonate treatment," Proc. Natl. Acad. Sci. USA, 95:5287-5292, 1998.
Collis et al., "Ribozyme minigene-mediated RAD51 down-regulation increases radiosensitivity of human prostate cancer cells," Nucleic Acids Res., 29:1534-1538, 2001.
Cui et al., "The XRCC2 and XRCC3 repair genes are required for chromosome stability in mammalian cells," Mutat. Res., 434:75-88, 1999.
Davies et al., "Role of BRCA2 in control of the RAD51 recombination and DNA repair protein," Mol. Cell, 7:273-282, 2001.
Ellouze et al., "Difference between active and inactive nucleotide cofactors in the effect on the DNA binding and the helical structure of RecA filament : Dissociation of RecA-DNA complex by inactive nucleotides," Eur. J. Biochem., 262(1):88-94, 1999.
Esashi et al., "CDK-dependent phosphorylation of BRCA2 as a regulatory mechanism for recombinational repair," Nature, 434:598-604, 2005.
Fuller and Painter, "A Chinese hamster ovary cell line hypersensitive to ionizing radiation and deficient in repair replication," Mutat. Res., 193:109-121, 1988.
Gasior et al., "Assembly of RecA-like recombinases: distinct roles for mediator proteins in mitosis and meiosis," Proc. Natl. Acad. Sci. USA, 98:8411-8418, 2001.
Godthelp et al., "Mammalian Rad51C contributes to DNA cross-link resistance, sister chromatid cohesion and genomic stability," Nucleic Acids Res., 30:2172-2182, 2002.
Han et al., "Accelerated screening of phage-display output with alkaline phosphatase fusions," Comb. Chem. High Throughput Screen, 7:55-62, 2004.
Han et al., "Identification of differentially expressed genes in pancreatic cancer cells using cDNA microarray," Cancer Res., 62:2890-2896, 2002.
Hansen et al., "The role of RAD51 in etoposide (VP16) resistance in small cell lung cancer," Int. J. Cancer, 105:472-479, 2003.
Henning and Sturzbecher, "Homologous recombination and cell cycle checkpoints: Rad51 in tumour progression and therapy resistance," Toxicology, 193:91-109, 2003.
Hiendleder, "Mitochondrial DNA inheritance after SCNT," Adv. Exp. Med. Biol., 591:103-16, 2007.
International Preliminary Report on Patentability, issued in International Application No. PCT/US2008/071364, dated Feb. 2, 2010.
International Search Report and Written Opinion, issued in International Application No. PCT/US2008/071364, dated Feb. 23, 2009.
International Search Report and Written Opinion, issued in International Application No. PCT/US13/72172, dated Feb. 14, 2014.
Ishibashi et al., "Nonhomologous chromosomal integration of foreign DNA is completely dependent on MUS-53(human Lig4 homolog) in Neurospora," PNAS, 103(40):14871-14876, 2006.
Ishida et al., "DIDS, a chemical compound that inhibits RAD51-mediated homologous pairing and strand exhange," Nucleic Acids Research, 37(10):3367-3376, 2009.
Ito et al., "Rad51 siRNA delivered by HVJ envelope vector enhances the anti-cancer effect of cisplatin," J. Gene Med., 7(8):1044-1052, 2005.
Jayathilaka et al., "A chemical compound that stimulates the human homologous recombination protein RAD51," PNAS, 105(41):15848-15853, 2008.
Jayathilaka et al., "Identification of a small molecule that stimulates human RAD51 protein," Int. J. Radiation Oncology, Biology, Physics, vol. 69, No. 3, Supplement, p. S598, Abstract #2719, 2007.
Kim et al., "Effect of ions and nucleotides on the interactions of yeast Rad51 protein with single-stranded oligonucleotides," J. Biochem. (Tokyo), 129:469-475, 2001.
Lee et al., "A complementary pair of rapid molecular screening assays for RecA activities," Analytical Biochemistry, 367:247-258, 2007.

(56) References Cited

OTHER PUBLICATIONS

Liu et al., "Involvement of Rad51C in two distinct protein complexes of Rad51 paralogs in human cells," Nucleic Acids Res., 30:1009-1015, 2002.
Liu et al., "XRCC2 and XRCC3, new human Rad51-family members, promote chromosome stability and protect against DNA cross-links and other damages," Mol. Cell, 1:783-793, 1998.
Maacke et al., "Autoantibodies in sera of pancreatic cancer patients identify recombination factor Rad51 as a tumour-associated antigen," J. Cancer Res. Clin. Oncol., 128:219-222, 2002.
Maacke et al., "DNA repair and recombination factor Rad51 is over-expressed in human pancreatic adenocarcinoma," Oncogene, 19:2791-2795, 2000.
Maacke et al., "Over-expression of wild-type Rad51 correlates with histological grading of invasive ductal breast cancer," Int. J. Cancer, 88:907-913, 2000.
Masson et al., "Complex formation by the human RAD51C and XRCC3 recombination repair proteins," Proc. Natl. Acad. Sci. USA, 98:8440-8446, 2001.
Masson et al., "Identification and purification of two distinct complexes containing the five RAD51 paralogs," Genes Dev., 15:3296-3307, 2001.
Moynahan et al., "BRCA2 is required for homology-directed repair of chromosomal breaks," Mol. Cell, 7:263-272, 2001.
Ohnishi et al., "In vitro and in vivo potentiation of radiosensitivity of malignant gliomas by antisense inhibition of the RAD51 gene," Biochem. Biophys. Res. Commun., 245:319-324, 1998.
Pellegrini et al., "Insights into DNA recombination from the structure of a RAD51-BRCA2 complex," Nature, 420:287-293, 2002.
Qiao et al., "High-level expression of Rad51 is an independent prognostic marker of survival in non-small-cell lung cancer patients," Br. J. Cancer, 93:137-143, 2005.
Qui et al., "Stereoselective synthesis of chiral IBR2 analogues," J. Org. Chem., 74:2018-2027, 2009.
Raderschall et al., "Elevated levels of Rad51 recombination protein in tumor cells," Cancer Res., 62:219-225, 2002.
Russell et al., "Gleevec-mediated inhibition of Rad51 expression and enhancement of tumor cell radiosensitivity," Cancer Res., 63:7377-7383, 2003.
Shin et al., "Full-length archaeal Rad51 structure and mutants: mechanisms for RAD51 assembly and control by BRCA2," Embo. J., 22:4566-4576, 2003.
Shinohara et al., "Rad51 protein involved in repair and recombination in S. cerevisiae is a RecA-like protein," Cell, 69:457-470, 1992.
Takata et al., "Chromosome instability and defective recombinational repair in knockout mutants of the five Rad51 paralogs," Mol. Cell Biol., 21:2858-2866, 2001.
Tebbs et al., "Correction of chromosomal instability and sensitivity to diverse mutagens by a cloned cDNA of the XRCC3 DNA repair gene," Proc. Natl. Acad. Sci. USA, 92:6354-6358, 1995.
Thompson and Schild, "Homologous recombinational repair of DNA ensures mammalian chromosome stability," Mutat. Res., 477:131-153, 2001.
Thompson and Schild, "The contribution of homologous recombination in preserving genome integrityin mammalian cells," Biochimie., 81:87-105, 1999.
Wachters et al., "Selective targeting of homologous DNA recombatyion repair by gemcitabine," Int. J. of Radiation Oncology, Biology, Physics, 57(2):553-562, 2003.
Wang et al., "Caffeine inhibits homology-directed repair of I-SceI-induced DNA double-stranded breaks," Oncogene, 23(3):824-834, 2004.
Wiese et al., "Interactions involving the Rad51 paralogs Rad51C and XRCC3 in human cells," Nucleic Acids Res., 30:1001-1008, 2002.
Wittung et al., "Thermochemical and kinetic evidence for nucleotide-sequence-dependent RecA-DNA interactions," Eur. J. Biochem., 245:715-719, 1997.
Wong et al., "RAD51 interacts with the evolutionarily conserved BRC motifs in the human breast cancer susceptibility gene brca2," J. Biol. Chem., 272:31941-31944, 1997.
Yoshikawa et al., "Abnormal expression of BRCA1 and BRCA1-interactive DNA-repair proteins in breast carcinomas," Int. J. Cancer, 88:28-36, 2000.
Yu et al., "Dynamic control of Rad51 recombinase by self-association and interaction with BRCA2," Mol. Cell, 12:1029-1041, 2003.
Yuan et al., "BRAC2 is required for ionizing radiation-induced assembly of Rad51 complex in vivo," Cancer Res., 59:3547-3551, 1999.
Zaitseva et al., "The DNA binding properties of Saccharomyces cerevisiae Rad51 protein," J. Biol. Chem., 274:2907-2915, 1999.
Zhang et al., "A Simple Statistical Parameter for Use in Evaluation and Validation of High Throughput Screening Assays," J. Biomol. Screen, 4:67-73, 1999.

* cited by examiner

Figure 5A
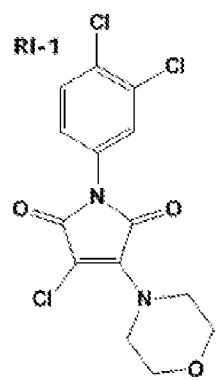
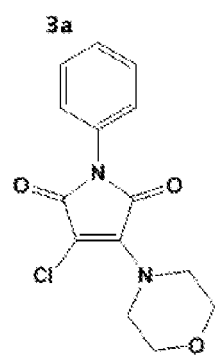
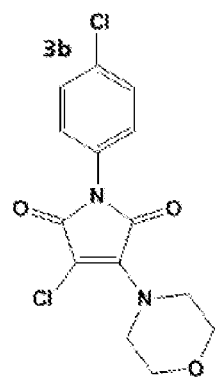
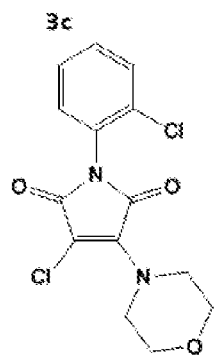
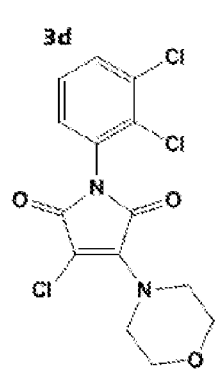
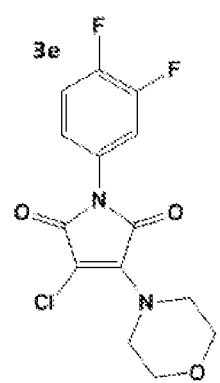
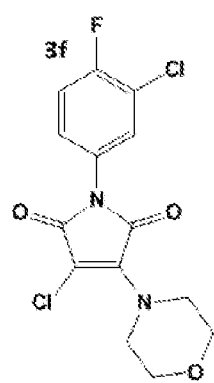
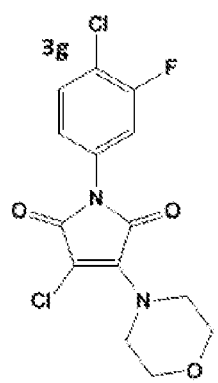
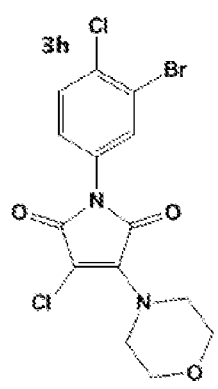
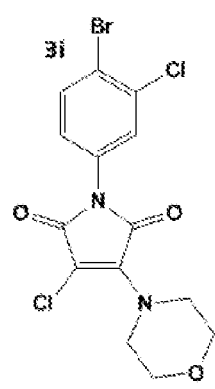

Figure 5B
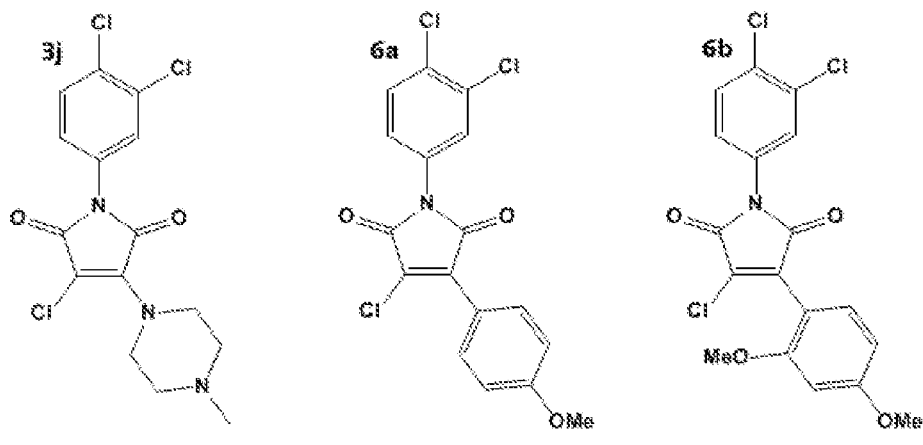
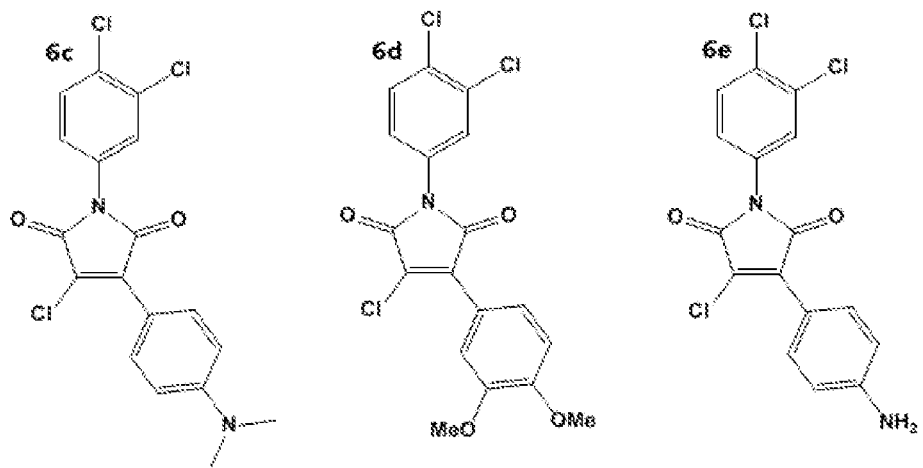
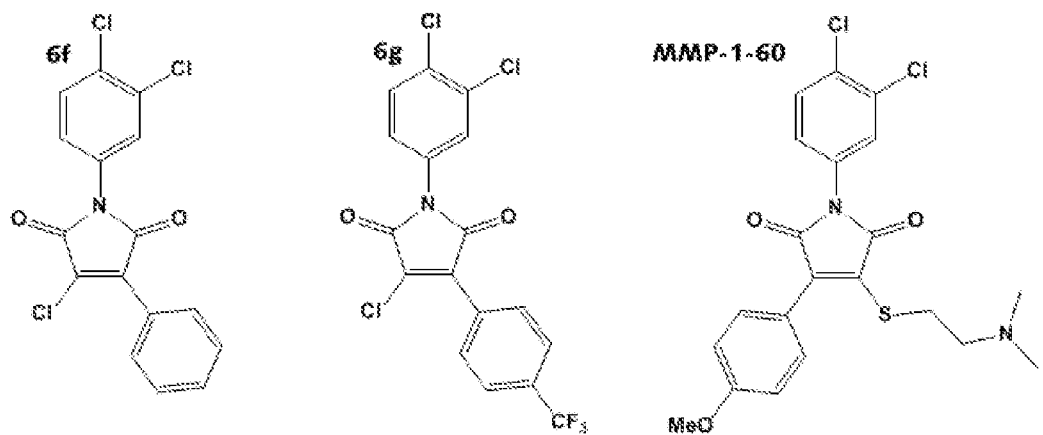

Figure 6A-B
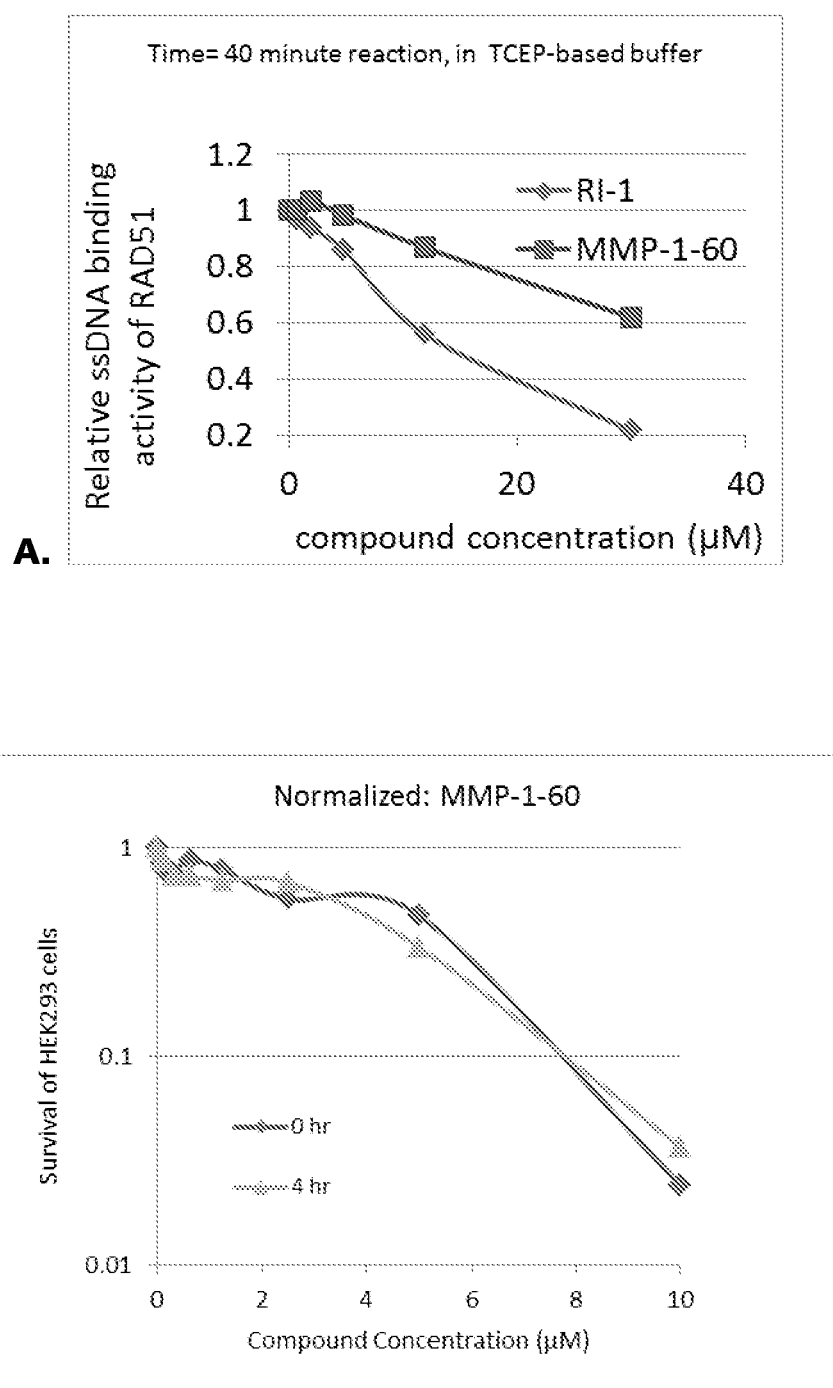

| Analog | R | DNA Binding IC$_{50}$ (μM) | LD$_{50}$ (μM) | Sensitization to MMC |
|---|---|---|---|---|
| 3a | phenyl | 17.85 ± 1.17 | 40.21 ± 4.04 | + |
| 3b | 4-Cl-phenyl | 38.17 ± 2.87 | > 80 | + |
| 3c | 2-Cl-phenyl | 19.70 ± 0.99 | > 80 | N/A |
| 3d | 2,3-diCl-phenyl | 14.88 ± 1.06 | 58.35 ± 5.31 | N/A |
| 3e | 2,4-diF-phenyl | 13.16 ± 0.88 | 19.83 ± 0.79 | + |
| 3f | 2-Cl-4-F-phenyl | 8.32 ± 0.52 | 18.81 ± 0.34 | + |
| 3g | 2-F-3-Cl-phenyl | 7.91 ± 0.50 | 19.74 ± 1.93 | − |
| 3h | 2-Br-3-Cl-phenyl | 9.94 ± 2.37 | 11.65 ± 1.52 | + |
| 3i | 2-Cl-3-Br-phenyl | 3.10 ± 0.28 | 16.32 ± 2.21 | + |

| Analog | R | DNA Binding IC$_{50}$ (μM) | LD$_{50}$ (μM) | Sensitization to MMC |
|---|---|---|---|---|
| 3j | NMe (N-methylpiperazine) | 6.43 ± 0.98 | 14.58 ± 0.92 | + |
| 6a | 4-OMe phenyl | 5.29 ± 1.39 | 10.07 ± 2.36 | − |
| 6b | 2,4-diOMe phenyl | ■ | 5.63 ± 0.92 | − |
| 6c | 4-NMe$_2$ phenyl | 15.62 ± 2.30 | 6.62 ± 1.62 | − |
| 6d | 3,4-diOMe phenyl | 2.14 ± 0.62 | 11.16 ± 2.85 | − |
| 6e | 4-NH$_2$ phenyl | 1.40 ± 0.20 | 2.18 ± 0.21 | − |
| 6f | phenyl | 0.93 ± 0.14 | 11.30 ± 2.71 | − |
| 6g | 4-CF$_3$ phenyl | 0.81 ± 0.02 | 28.29 ± 3.07 | − |

Figure 7C

| Analog | R | DNA Binding IC$_{50}$ (μM) | LD$_{50}$ (μM) | Sensitization to MMC |
|---|---|---|---|---|
| 9a | –Br | 0.37 ± 0.04 | 45.88 ± 1.46 | + |
| 9b | –I | 0.25 ± 0.02 | 66.21 ± 3.33 | – |
| 7a (RI-2) | 4-OMe-phenyl | 44.17 ± 6.75 | 70.16 ± 3.96 | + |
| 7b | 3-OMe-phenyl | ■ | > 80 | N/A |
| 7c | 4-NMe$_2$-phenyl | > 50 | > 80 | N/A |
| 7d | 3,4-di-OMe-phenyl | ■ | > 80 | N/A |
| 7e | 4-NH$_2$-phenyl | > 50 | > 80 | N/A |
| 7f | phenyl | ■ | > 80 | N/A |
| 7g | 4-CF$_3$-phenyl | ■ | > 80 | N/A |

| Analog | R₁ | R₂ | DNA Binding IC$_{50}$ (μM) | LD$_{50}$ (μM) | Sensitization to MMC | cLogP |
|---|---|---|---|---|---|---|
| RI-2 | -C₆H₄-OMe | morpholine | 187.8 ± 42.2 | 70.2 ± 4.0 | + | 4.212 |
| HP-1-16 | morpholine | -S-CH₂CH₂-OH | 91.9 ± 15.3 | 95.5 ± 22.0 | + | 2.162 |
| MMP-1-14 | morpholine | -S-CH₂CH₂-NH₂ | ■ | > 150 | − | 1.599 |
| MMP-1-75 | -C₆H₄-OMe | -S-CH₂CH₂-NH₂ | ■ | 101.6 ± 22.9 | + | 3.502 |
| 14-ING-9 | morpholine | -S-CH₂CH₂-NMe₂ | ■ | > 150 | + | 2.821 |
| MMP-1-73 | -C₆H₄-CF₃ | -S-CH₂CH₂-NMe₂ | 2.6 ± 1.0 | 23.7 ± 6.3 | + | 4.318 |
| MMP-1-77 | -C₆H₃(OMe)₂ | -S-CH₂CH₂-NMe₂ | 3.9 ± 1.3 | 4.7 ± 1.0 | + | 5.566 |
| MMP-1-60 | -C₆H₄-OMe | -S-CH₂CH₂CH₂-NMe₂ | 3.9 ± 1.1 | 5.1 ± 1.1 | + | 4.728 |

Figure 9A-C
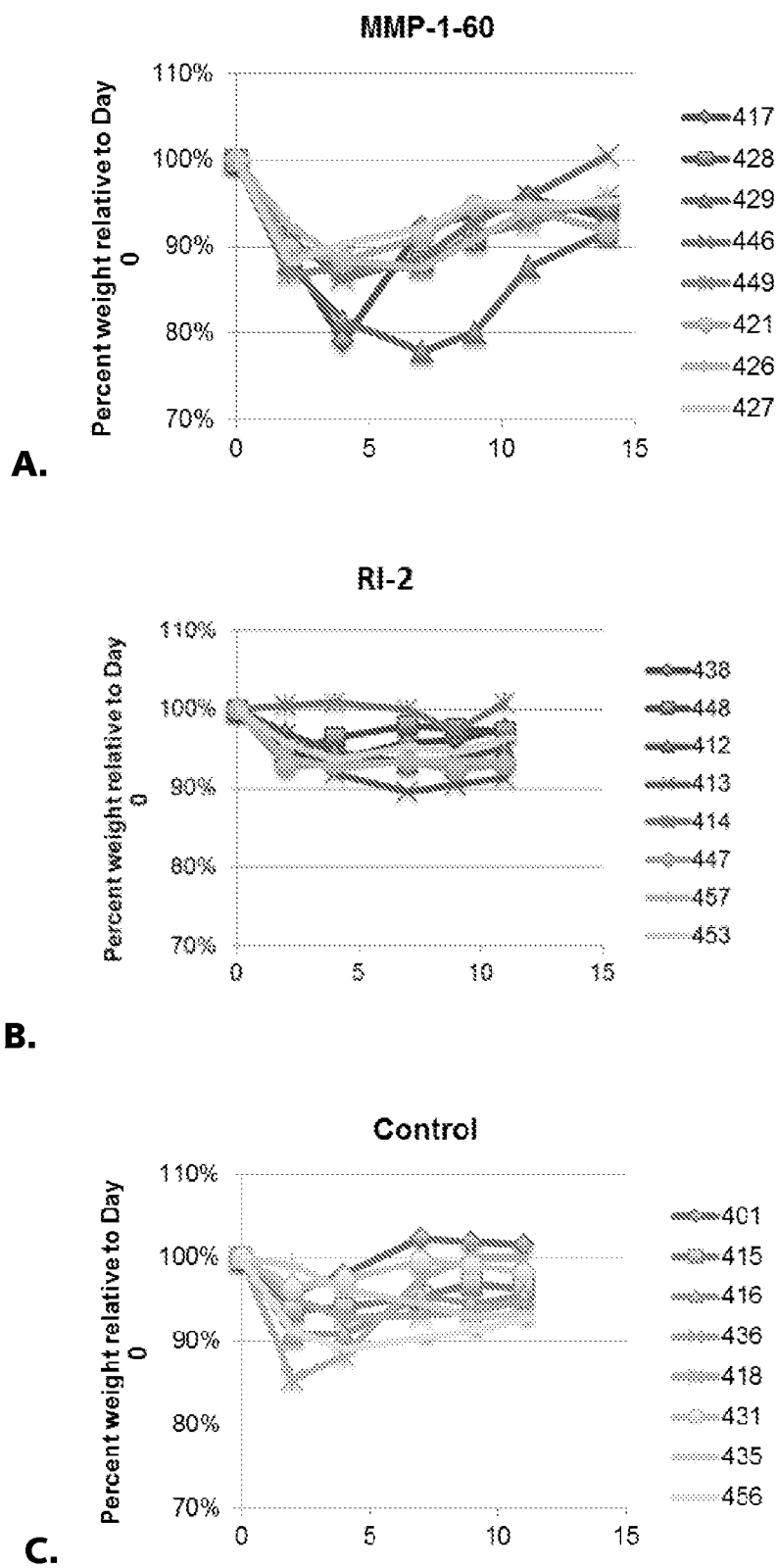

METHODS AND COMPOSITIONS INVOLVING RAD51 INHIBITORS

CROSS REFERENCE TO RELATED APPLICATIONS

This application is a national phase application under 35 U.S.C. 371 of International Application No. PCT/US2013/072172 filed on Nov. 27, 2013, which claims the benefit of priority of U.S. Provisional Patent Application No. 61/731,982 filed on Nov. 30, 2012. The entire contents of each of the above-referenced disclosures are specifically incorporated herein by reference without disclaimer.

STATEMENT REGARDING FEDERALLY SPONSORED RESEARCH OR DEVELOPMENT

This invention was made with government support under grant number R01 CA142642 awarded by the National Institutes of Health. The government has certain rights in the invention.

BACKGROUND OF THE INVENTION

1. Field of the Invention

The present invention relates generally to the fields of biochemistry, cell biology, organic chemistry, and oncology. More specifically, it concerns methods for synthesizing inhibitors of RAD51 and inhibiting RAD51 protein activity in a cell.

2. Description of Related Art

Homologous recombination (HR) is an essential process in eukaryotic cells that provides repair of DNA double-strand breaks (DSBs) and lesions that block DNA replication. Faithful DSB repair by HR utilizes an undamaged sister chromatid as a template to guide the repair process. This distinguishes HR from the error-prone non-homologous end joining (NHEJ) DNA repair pathway (Thompson and Schild, 2001). Since HR facilitates cellular recovery from replication-blocking lesions and collapsed replication forks, cells with impaired HR capacity are known to exhibit profound sensitivities to a class of chemotherapeutic drugs that generate inter-strand DNA crosslinks (ICLs, Tebbs et al., 1995; Liu et al., 1998; Takata et al., 2001).

RAD51 is an evolutionarily conserved protein that is central to HR. One of the initial steps in HR is the polymerization of RAD51 on single-stranded DNA (ssDNA), wherein protomers of RAD51 oligomerize into a helical nucleoprotein filament at the site of damaged DNA. This nucleoprotein filament subsequently searches for a homologous DNA sequence and invades it to form a joint molecule. With the assistance of other related HR proteins, accurate DNA synthesis is then performed using the undamaged sequence as a template. Over-expression of RAD51 protein in cells has been shown to elevate HR efficiency and to generate resistance to ICL-forming drugs (Vispe et al., 1998; Slupianek et al., 2001; Bello et al., 2002; Hansen et al., 2003). This has important implications for oncology research, since RAD51 is over-expressed in a wide range of human cancer cell types (Klein 2008; Hine et al., 2008).

The reliance of cancer cells on RAD51-dependent HR combined with the upregulation of RAD51 in certain human cancer cell types make RAD51 a desirable target for small molecule inhibition.

SUMMARY OF THE INVENTION

Embodiments are based on the identification and characterization of compounds that alter the ability of the RAD51 protein to bind fluorescently labeled oligonucleotides. Therefore, there are methods and compositions involving compounds that directly inhibit the activity of the RAD51 protein. In certain embodiments, methods and compositions concern compounds that decrease, inhibit, or reduce RAD51 activity.

In certain embodiments, there are methods for inhibiting RAD51 protein in a cell comprising providing to the cell an effective amount of a RAD51 protein inhibitor, wherein the inhibitor is a small molecule that directly inhibits the activity of RAD51 protein. This means that small molecules alter the activity of RAD51 protein (or a RAD51 protein analog or homolog) directly (i.e., RAD51 activity decreases when the RAD51 protein is contacted or incubated with the small molecule), and not indirectly, such as by altering the expression level of RAD51.

In some embodiments, the methods and compositions concern a compound that is a RAD51 inhibitor, meaning that the compound directly decreases, inhibits, and/or attenuates RAD51 protein activity when the RAD51 protein is exposed to the compound. The terms "inhibitor" and "antagonist" are used interchangeably herein.

Therefore, embodiments cover a number of methods involving a RAD51 inhibitor, that decrease, inhibit or reduce RAD51 activity by or by at least about 10, 15, 20, 25, 30, 35, 40, 45, 50, 55, 60, 65, 70, 75, 80, 85, 90, 95, or 100% (and any range derivable therein) compared to RAD51 activity in the absence of the RAD51 inhibitor. Therefore, in some embodiments, there are methods for inhibiting RAD51 in a cell comprising providing to the cell an effective amount of a RAD51 small molecule that directly inhibits RAD51 activity in a cell. In particular embodiments, the RAD51 inhibitor decreases RAD51 filament formation when the inhibitor is incubated with RAD51 protein under conditions to promote filament formation. In certain other embodiments, the RAD51 inhibitor attenuates or inhibits homologous recombination via RAD51 inhibition in a cell.

A RAD51 inhibitor is a compound that acts in conjunction with RAD51 protein to inhibit, attenuate or decrease the activity of the RAD51 protein. In certain embodiments the RAD51 inhibitor is a small molecular weight compound. In specific embodiments, the RAD51 inhibitor is a compound of formula:

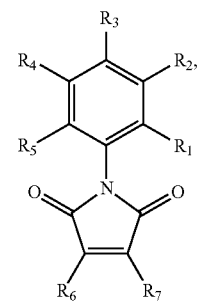

wherein $R_1$-$R_5$ are each separately H or halogen, and $R_6$ and $R_7$ are each independently H, halogen, substituted or unsubstituted aryl, heterocycle, thioether, (amine)thioether, (alkylamine)thioether, (hydroxy)thioether, 4-methylpiperazin-1-yl, N-morpholinyl, 2-(N,N-dimethylamino)-ethylthioether, 2-aminoethylthioether, or 2-hydroxyethylthioether. The RAD51 inhibitor may, in certain embodiments, be selected from the compounds shown in FIG. 5, or a salt thereof. It is specifically contemplated that derivatives, metabolites, and prodrugs of these compounds may also be used as RAD51 inhibitors in some embodiments of the invention.

In some embodiments, the RAD51 inhibitor is a compound of formula:

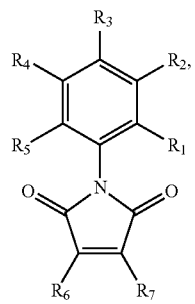

wherein $R_1$-$R_5$ are each separately H or halogen, $R_6$ is a halide and $R_7$ is a substituted or unsubstituted aryl group. The substituted aryl group may be substituted with one or more of the following non-limiting examples: alkoxy, amine, alkylamine, amino, and trihalomethyl. In some embodiments, $R_2$ is a halide. In further embodiments, $R_3$ is a halide. In yet further embodiments, $R_2$ and $R_3$ are each independently, halides. In some embodiments, the RAD51 inhibitor is a compound depicted in FIG. 7B.

In some embodiments, the RAD51 inhibitor is a compound of the formula:

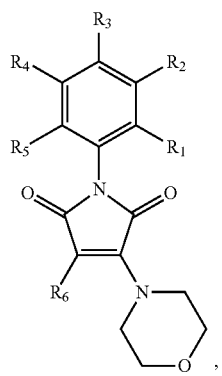

wherein $R_1$-$R_5$ are each separately hydrogen or halogen and $R_6$ is a halide. In some embodiments, $R_2$ is a halide. In further embodiments, $R_3$ is a halide. In yet further embodiments, $R_2$ and $R_3$ are each independently, halides. In some embodiments, the RAD51 inhibitor is a compound depicted in FIG. 7A.

In other embodiments, the RAD51 inhibitor is a compound of the formula:

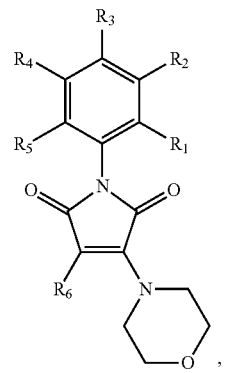

wherein $R_1$, $R_4$ and $R_5$ are each hydrogen atoms, $R_2$ is a halide, $R_3$ is a halide, and $R_6$ is a substituted or unsubstituted aryl group. The substituted aryl group may be substituted with one or more of the following non-limiting examples: alkoxy, amine, alkylamine, amino, and trihalomethyl. In some embodiments, the RAD51 inhibitor is a compound depicted as 7a through 7g in FIG. 7C.

In other embodiments, the RAD51 inhibitor is a compound of the formula:

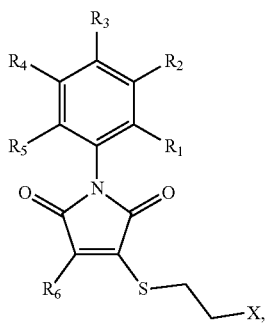

wherein $R_1$, $R_4$ and $R_5$ are each hydrogen atoms, $R_2$ is a halide, $R_3$ is a halide, X is $NH_2$, $NR_{10}R_{11}$, or OH, $R_{10}$ and $R_{11}$, each independently, are alkyl groups, and $R_6$ is a substituted or unsubstituted aryl or a heterocycloalkyl group. In further embodiments $R_{10}$ and $R_{11}$ are each methyl groups. In some embodiments, the heterocycloalkyl group is morpholino. In some embodiments, $R_6$ is a phenyl group substituted with one or more of alkoxy, amino, amine, alkylamine, or trihalomethyl groups. In particular embodiments, the RAD51 inhibitor is a compound depicted as HP-1-16, MMP-1-14, MMP-1-75, 14-ING-9, MMP-1-73, MMP-1-77 or MMP-1-60 in FIG. 7D.

The small molecules described herein typically contain an aryl group. Accordingly, in certain embodiments, compounds comprising one or more aryl groups are contemplated. The aryl groups may be substituted by any substituent known to those of skill in the art (e.g., H, amino, nitro, halo, mercapto, cyano, azido, silyl, hydroxy, alkyl, haloalkyl, dihaloalkyl, trihaloalkyl, alkenyl, alkynyl, aryl, aralkyl, alkoxy, alkenoxy, alkynyloxy, aryloxy, acyloxy, alkylamino, alkenylamino, alkynylamino, arylamino, aralkylamino, amido, alkylthio, alkenylthio, alkynylthio, arylthio, aralkylthio, acylthio, alkylsilyl, phosphonate, phosphinate, or any combination thereof). In certain embodiments, the small molecules are any one or more of the specific chemical compounds whose structures are shown herein.

Additional embodiments concern methods for sensitizing cancer cells to a DNA damaging agent comprising administering to a cancer patient an effective amount of a RAD51 small molecule that directly inhibits RAD51 activity in the cancer cells.

Other embodiments of the invention include methods for inhibiting conception or the use of compositions of the invention as contraceptives. Because homologous recombination is required for the forming function of fertilized eggs and sperm, it is contemplated that RAD51 inhibitors can be used to reduce fertility of an individual by exposing the individual's sex cells to an effective amount of a RAD51 inhibitor.

An "effective amount" of a compound or composition, generally, is defined as that amount sufficient to detectably and repeatedly achieve the stated desired result, for example, to ameliorate, reduce, minimize or limit the extent of the disease or its symptoms or to increase, stimulate, or promote a desirable physiological response, such as homologous recombination. In some embodiments, the stated result may include elimination, eradication or cure of disease.

It is contemplated that in certain embodiments, a cell is a human cell and the subject or patient is a human patient. In other embodiments, a cell is a mammalian cell and the subject or patient is a mammalian patient. In some embodiments, a cell is a Drosophila cell and the subject or patient is a Drosophila patient. It will be understood that different mammals have their own RAD51 protein that would be a homolog of the human protein. In certain other embodiments, the cell is a eukaryotic cell, while in other embodiments, the cell is a prokaryotic cell and a RAD51 protein homolog or analog is the protein that is modulated. In specific embodiments, a cell may be a sex cell, while in others, the cell is a somatic cell. In particular embodiments, cells used in methods of the invention may be from a cell line. In certain embodiments, the cell is a cell from or in any organism described herein. Moreover, in some embodiments the cell is a cancer cell, while in other embodiments a cell is non-cancerous or normal. In some cases, a cancer cell is resistant to chemotherapy or radiation. Furthermore, it is contemplated that a cell can be in a patient. Additionally, a cell may be an embryonic stem (ES) cell, such as a murine ES cell, which are used for generating knockout mice. Alternatively, cells may be murine cells that are used for generating a transgenic mouse. Other transgenic animals can be generated using a particular animals cells in the context of methods of the invention.

Methods can be implemented as treatment for patients with cancer. The cancer may be any cancer treatable by administration of a compound described herein. In certain embodiments, a cancer may be treatable using a combination treatment involving a conventional DNA damaging agent with a RAD51 inhibitor. In some instances, the RAD51 inhibitor may be what allows a cancer to be treated with the DNA damaging agent. Methods can be implemented with any cancer that may be treated with a DNA damaging agent. For example, the cancer may be breast, prostate, ovarian, brain, melanoma, colorectal, liver, lymphoma, lung, oral, head, neck, spleen, lymph node, small intestine, large intestine, blood cells, stomach, pancreatic, endometrium, testicle, skin, esophagus, bone marrow, blood, cervical, bladder, Ewing's sarcoma, thyroid, a glioma, and/ or gastrointestinal. Methods and compositions are applicable to other cancers discussed herein, including pre-cancers and tumor cells.

In some embodiments, a cancer patient may have been treated with or will be treated with a DNA damaging agent. In related embodiments, a subject may have been exposed to a DNA damaging agent (as a harmful agent and not as part of a treatment) or be at risk for such exposure. It is contemplated that in some embodiments, the DNA damaging agent is an alkylating agent, nitrosourea, anti-metabolite, plant alkaloid, plant extract, or radioisotope. In specific embodiments, the DNA damaging agent is actinomycin, amsacrine, anthracyclines, bleomycin, busulfan, camptothecin, carboplatin, chlorambucil, cisplatin, cyclophosphamide, cytoxan, dactinomycin, daunorubicin, docetaxel, doxorubicin, epirubicin, hexamethylmelamineoxaliplatin, iphosphamide, melphalan, merchlorethamine, mitomycin, mitoxantrone, nitrosourea, paclitaxel, plicamycin, procarbazine, teniposide, triethylenethiophosphoramide or etoposide (VP16). Any other DNA damaging agent discussed herein may be implemented in methods. In certain embodiments, the DNA damaging agent is radiation.

Methods may involve multiple administrations of one or more compounds, compositions, and/or agents. In certain embodiments, cells or a subject are provided with a RAD51 inhibitor and a DNA damaging agent. It is contemplated that compounds, compositions, and/or agents may be formulated in a pharmaceutically acceptable formulation in certain embodiments of the invention.

Moreover, in some methods the order in which things are provided to cells or a subject may vary. In some embodiments, a RAD51 inhibitor is provided prior to a DNA damaging agent being provided to a cell or subject. In other embodiments, a RAD51 inhibitor is provided simultaneously with a DNA damaging agent or after the DNA damaging agent is provided. It is contemplated that a RAD51 inhibitor may be provided to a cell or subject within 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 32, 33, 34, 35, 36, 37, 38, 39, 40, 41, 42, 43, 44, 45, 46, 47, 48 hours and/or 1, 2, 3, 4, 5, 6, or 7 days (or any range derivable therein) of the cell or subject being provided with a DNA damaging agent, and vice versa. In certain embodiments, a RAD51 inhibitor is provided before, during, and/or after a DNA damaging agent is provided.

A "disease" is defined as a pathological condition of a body part, an organ, or a system resulting from any cause, such as infection, genetic defect, or environmental stress. A "health-related condition" is defined herein to refer to a condition of a body part, an organ, or a system that may not be pathological, but for which treatment is sought. Examples include conditions for which cosmetic therapy is sought, such as skin wrinkling, skin blemishes, and the like. The disease can be any disease, and non-limiting examples include hyperproliferative diseases such as cancer and pre-malignant lesions, wounds, and infections.

"Prevention" and "preventing" are used according to their ordinary and plain meaning to mean "acting before" or such an act. In the context of a particular disease or health-related condition, those terms refer to administration or application of an agent, drug, or remedy to a subject or performance of a procedure or modality on a subject for the purpose of blocking the onset of a disease or health-related condition.

It is specifically contemplated that any limitation discussed with respect to one embodiment of the invention may apply to any other embodiment of the invention. Furthermore, any composition of the invention may be used in any method of the invention, and any method of the invention may be used to produce or to utilize any composition of the invention.

The use of the term "or" in the claims is used to mean "and/or" unless explicitly indicated to refer to alternatives only or the alternative are mutually exclusive, although the disclosure supports a definition that refers to only alternatives and "and/or."

Throughout this application, the term "about" is used to indicate that a value includes the standard deviation of error for the device and/or method being employed to determine the value.

As used herein the specification, "a" or "an" may mean one or more, unless clearly indicated otherwise. As used herein in the claim(s), when used in conjunction with the word "comprising," the words "a" or "an" may mean one or more than one. As used herein "another" may mean at least a second or more.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE FIGURES

The following drawings form part of the present specification and are included to further demonstrate certain aspects of the present invention. The invention may be better understood by reference to one or more of these drawings in combination with the detailed description of specific embodiments presented herein.

FIG. 2A. Schematic representation of the FP experiments. Reversible vs. irreversible inhibition of RAD51 by compound was tested by incubating compounds with RAD51 while still attached to beads and prior to washing. Alternatively, inhibition of RAD51 by compound was tested by adding the compound after the protein has been released from the beads. FIG. 2B. Inhibition of RAD51 by compound after the protein has been released from the beads. The inhibitory activity of RI-1 on the DNA binding activity of RAD51 was found to be time-dependent, consistent with the requirement for a chemical reaction to achieve inhibitory activity. This time dependence was also observed with other RI-1 analogs with intact Michael acceptor groups (data not shown). In contrast, no time-dependent increase in the inhibitory activity induced by RI-2 was observed. FIG. 2C. Reversible vs. irreversible inhibition of RAD51. Biotinylated RAD51 was immobilized on streptavidin polyacrylamide beads. The RAD51-coated beads were incubated with compound and subsequently washed extensively to remove any compound that was not covalently attached. The treated protein was subsequently cleaved from the beads and tested for DNA binding activity using our standard FP-based assay. As expected, RAD51 protein that had been treated with 10 µM RI-1 prior to washing was significantly inactivated, consistent with RI-1's established role as an irreversible inhibitor. By contrast, RAD51 protein that had been treated with RI-2 (concentrations up to 240 µM) prior to washing exhibited no measurable loss of DNA binding activity, even though RI-2 is known to inhibit RAD51 with an $IC_{50}$ of 44.17 µM in the standard DNA binding assay, indicating that RAD51 inhibition by RI-2 is fully reversible.

FIGS. 5A-5D: Structures of various RAD51 inhibitors of the present invention.

FIGS. 6A-6B: A. ssDNA binding activity of RAD51 in response to RAD51 antagonists. MMP-1-60 displays RAD51 inhibitory activity intermediate to RI-1 and RI-2 (not shown). B. MMP-1-60 toxicity to immortalized human cells. MMP-1-60 displays comparable cell toxicity, after 4 hours of pre-incubation with tissue culture media and no pre-incubation, demonstrating the stability of MMP-1-60.

FIGS. 7A-7D. Structural-activity relationship data for selected RAD51 inhibitors. Inhibitory concentration for DNA binding, lethal dose (50%), sensitization to MMC and octanol/water partition coefficient are listed for RAD51 inhibitors.

FIGS. 9A-9C: A. MMP-1-60 toxicity in mice. Weight loss in mice is measured as an indicator of MMP-1-60 toxicity. The graph illustrates percent weight relative to day for several mice. B. RI-2 toxicity in mice. Weight loss in mice is measured as an indicator of RI-2 toxicity. The graph illustrates percent weight relative to day for several mice. C. Control mice. Percent weight relative to day is illustrated for a number of control mice.

DESCRIPTION OF ILLUSTRATIVE EMBODIMENTS

Figure 1:
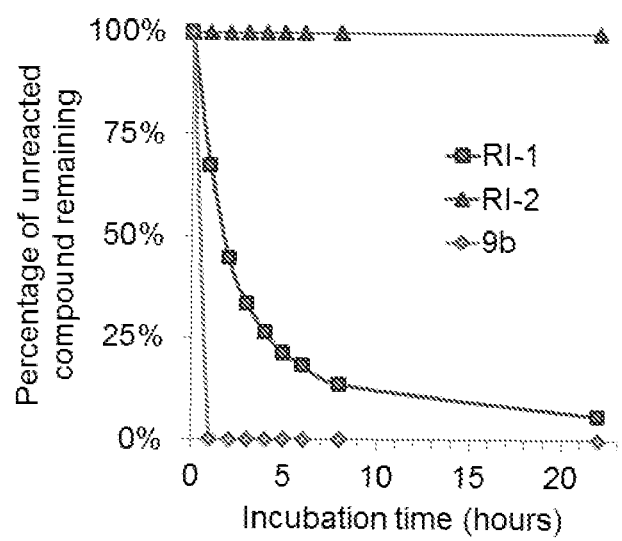
FIG. 1. Reaction of RI-1, RI-2, and 9b with glutathione. Glutathione is a tripeptide that contains a nucleophilic sulfhydryl group. Glutathione may react irreversibly with a Michael acceptor compound containing a suitable leaving group at the 4-position. Compound 9b, containing an iodide at the 4-position, reacts rapidly with glutathione, leaving no detectable compound at the first time point measured. RI-1, containing a less efficient chloride leaving group at the 4-position, displays reduced glutathione reactivity. RI-2, containing a p-anisole at the 4-position exhibited no reactivity toward glutathione after incubation for 24 hours.
Figure 2:
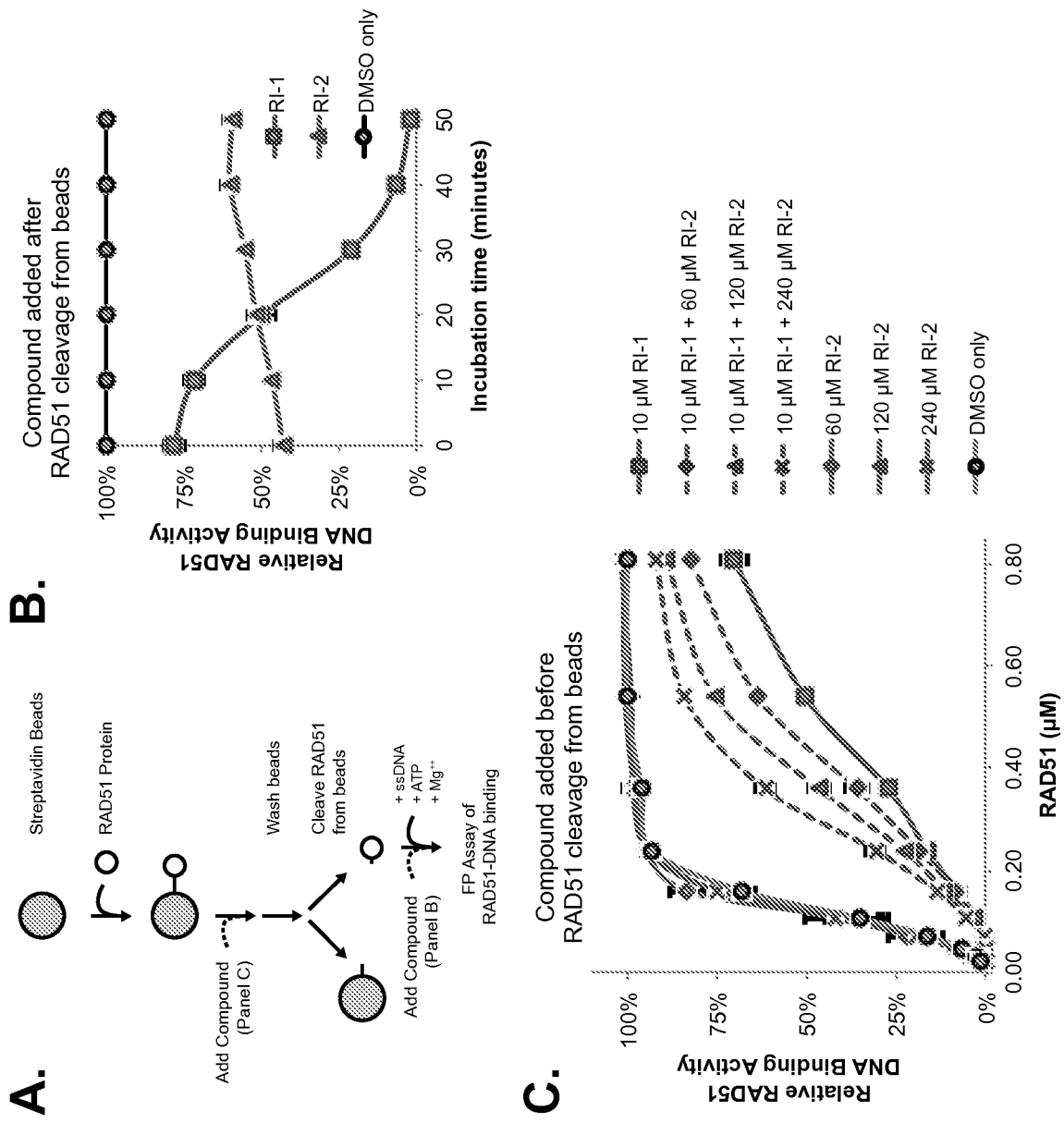
FIGS. 2A-C.

The present invention overcomes the deficiencies of the prior art by providing compounds that inhibit the activity of a protein involved in homologous recombinational (HR) DNA repair, RAD51. As discussed above, HR DNA repair confers cellular resistance to ionizing radiation and certain DNA damaging agents, including some anti-cancer drugs. Pharmacologic manipulation of HR levels may be used to modulate this resistance. RAD51 is the central protein involved in the initiation of HR. Drugs that reduce RAD51 function could potentially be used to inhibit HR in cancer cells, thereby overcoming the resistance of malignant tumors to common oncologic therapies.

A targeted approach that focuses on HR is particularly appealing, since several studies have suggested that HR inhibition preferentially sensitizes tumor cells relative to normal cells (Russell et al., 2003; Ito et al., 2005). In one such study, Gleevec-mediated inhibition of RAD51 expression resulted in an elevated radio-sensitivity for glioma cancer cell lines, but had no significant effect on normal human fibroblasts (Russell et al., 2003). Similarly, Ito et. al. blocked RAD51 expression with siRNA techniques in various human cancer cell lines. The sensitivity to cisplatin was enhanced in all of the human cancer cell lines tested, but not in normal human fibroblasts (Ito et al., 2005). Therefore, a strategy for pharmacologic inhibition of HR holds promise for improving the therapeutic ratios of existing oncology treatments.

A. RAD51 Protein

RAD51 filament formation is a well accepted critical step in the initiation of HR repair. Biochemical studies have shown that RAD51 protein assembles into filaments readily on sites of single stranded DNA (ssDNA). In vitro filament formation is magnesium and ATP dependent, and requires a concentration of RAD51 protein of approximately 250 nM. This reaction also demonstrates cooperativity, such that a threshold level of RAD51 binding to ssDNA will stimulate further filament formation (Zaitseva et al., 1999; Shinohara et al., 1992). One mechanism by which cells can up-regulate filament formation is over-expression of RAD51 protein. RAD51 is over-expressed in a number of human cancer cell lines (Raderschall et al., 2002; Russell et al., 2003; Hansen et al., 2003) and human tumors (Maacke et al., 2000a; Maacke et al., 2000b; Han et al., 2002; Henning and Sturzbecher 2003; Yoshikawa et al., 2000; Qiao et al., 2005). Fluorescence in situ hybridization (FISH) experiments have shown that the RAD51 gene is not amplified. Other experiments have demonstrated that RAD51 protein half-life is normal in tumor cells. Taken together, this suggests that the increased protein levels result from transcriptional up-regulation (Raderschall et al., 2002). There are also data to suggest that RAD51 over-expression can compensate for loss of RAD51 paralog proteins, thus by-passing the need for a mediator protein that would have otherwise been rate limiting (Takata et al., 2001).

RAD51 over-expression is particularly dramatic in the case of pancreatic cancer. Han et al. (2002) performed a cDNA microarray analysis comparing pancreatic cancer cells lines to normal pancreatic cells; RAD51 was among the 30 most over-expressed genes in this analysis. This result was confirmed with an immunohistochemical (IHC) analysis showing strong RAD51 staining in 71.8% of malignant pancreatic tumors in humans (Han et al., 2002). A similar study of 47 human pancreatic tumor tissue specimens showed RAD51 overexpression in 66% of tumors (Maacke et al., 2000b). In fact, RAD51 overexpression is so great that 7% of pancreatic cancer patients generate auto-antibodies to RAD51, which can be detected in their sera (Maacke et al., 2002). A functional analysis using a system of inducible RAD51 overexpression in pancreatic cells directly showed that overexpression confers resistance to DSB's (Maacke et al., 2000b). A growing body of literature agrees with this finding, suggesting that high RAD51 protein expression levels can modulate the resistance of cancer cells to IR (ionizing radiation) and some chemotherapeutic drugs.

B. Homologous Recombination and BRCA1 Mutations

The breast cancer susceptibility gene BRCA2 plays an important role in HR (Moynahan et al., 2001). It has been speculated that BRCA2 protein either chaperones RAD51 monomers, that it serves as mediator for RAD51 filament assembly at sites of DNA damage, and/or that it acts to stabilize existing filaments. A recent report suggested that RAD51 directly interacts with a C-terminal region of BRCA2 protein (Esashi et al., 2005). RAD51 is also known to directly bind six of the eight conserved BRC repeats within human BRCA2 (Chen et al., 1998; Wong et al., 1997). Crystal structure data have been generated using a fusion protein containing BRC4 covalently linked to the C-terminal core domain of RAD51. This and other studies have demonstrated that BRC repeats share a conserved motif that is thought to mimic a primary interface used in RAD51 polymerization (Shin et al., 2003; Pellegrini et al., 2002). Various BRC peptides have been shown capable of blocking self-association by RAD51 monomers, inhibiting RAD51 filament formation, and sensitizing cells to DNA damage (Chen et al., 1999; Davies et al., 2001; Yuan et al., 1999). For example Chen et. al. reported that conditional expression of wild-type BRC4 resulted in hypersensitivity to irradiation and an inability to form radiation-induced RAD51 foci in breast cancer cells (Chen et al., 1999).

Preliminary tumor studies by the present inventors focused on HR by modulating the RAD51 paralog protein XRCC3. Using xenograft tumors grown in nude mice, cisplatin treatment was found to produce regression and cure of HR-deficient xenograft tumors using a treatment schedule that has little effect of HR-competent tumors. Similarly, the HR-deficient tumors were sensitive to relatively low doses of ionizing radiation, compared to HR-competent tumors. Other clinical studies suggest that, like XRCC3-deficient tumors, HR-deficient human tumors (due to BRCA1-mutation) are especially susceptible to DNA damaging chemotherapeutic agents (Porter et al., 1994; Rubin et al., 1996). Tanaka and colleagues found that in a group ovarian cancer patients receiving cisplatin treatment, those defective for BRCA1 had a five-year survival of 79% while patients in the control group had a five-year survival of only 30% (Alda et al., 1998). Similarly, Marcus et al. (1996) found that BRCA1-defective women with breast cancer had relatively favorable outcomes, despite having tumors with higher grade and higher S-phase fraction. Thus, deficiencies of HR may sensitize tumor cells to some chemotherapy drugs and IR, providing evidence that pharmacologic inhibitors of HR are likely to improve the clinical efficacy of cancer treatments.

C. Cancer and DNA Damaging Agents

In certain embodiments, the invention is applicable to the treatment of cancer insofar as such treatments may involve DNA damaging agents.

Cancer cells that may be treated by methods and compositions of the invention also include cells from the bladder, blood, bone, bone marrow, brain, breast, colon, esophagus, gastrointestine, gum, head, kidney, liver, lung, nasopharynx, neck, ovary, prostate, skin, stomach, testis, tongue, or uterus. In addition, the cancer may specifically be of the following histological type, though it is not limited to these: neoplasm, malignant; carcinoma; carcinoma, undifferentiated; giant and spindle cell carcinoma; small cell carcinoma; papillary carcinoma; squamous cell carcinoma; lymphoepithelial carcinoma; basal cell carcinoma; pilomatrix carcinoma; transitional cell carcinoma; papillary transitional cell carcinoma; adenocarcinoma; gastrinoma, malignant; cholangiocarcinoma; hepatocellular carcinoma; combined hepatocellular carcinoma and cholangiocarcinoma; trabecular adenocarcinoma; adenoid cystic carcinoma; adenocarcinoma in adenomatous polyp; adenocarcinoma, familial polyposis coli; solid carcinoma; carcinoid tumor, malignant; branchioloalveolar adenocarcinoma; papillary adenocarcinoma; chromophobe carcinoma; acidophil carcinoma; oxyphilic adenocarcinoma; basophil carcinoma; clear cell adenocarcinoma; granular cell carcinoma; follicular adenocarcinoma; papillary and follicular adenocarcinoma; nonencapsulating sclerosing carcinoma; adrenal cortical carcinoma; endometroid carcinoma; skin appendage carcinoma; apocrine adenocarcinoma; sebaceous adenocarcinoma; ceruminous adenocarcinoma; mucoepidermoid carcinoma; cystadenocarcinoma; papillary cystadenocarcinoma; papillary serous cystadenocarcinoma; mucinous cystadenocarcinoma; mucinous adenocarcinoma; signet ring cell carcinoma; infiltrating duct carcinoma; medullary carcinoma; lobular carcinoma; inflammatory carcinoma; paget's disease, mammary; acinar cell carcinoma; adenosquamous carcinoma; adenocarcinoma squamous metaplasia; thymoma, malignant; ovarian stromal tumor, malignant; thecoma, malignant; granulosa cell tumor, malignant; androblastoma, malignant; sertoli cell carcinoma; leydig cell tumor, malignant; lipid cell tumor, malignant; paraganglioma, malignant; extra-mammary paraganglioma, malignant; pheochromocytoma; glomangiosarcoma; malignant melanoma; amelanotic melanoma; superficial spreading melanoma; malig melanoma in giant pigmented nevus; epithelioid cell melanoma; blue nevus, malignant; sarcoma; fibrosarcoma; fibrous histiocytoma, malignant; myxosarcoma; liposarcoma; leiomyosarcoma; rhabdomyosarcoma; embryonal rhabdomyosarcoma; alveolar rhabdomyosarcoma; stromal sarcoma; mixed tumor, malignant; mullerian mixed tumor; nephroblastoma; hepatoblastoma; carcinosarcoma; mesenchymoma, malignant; brenner tumor, malignant; phyllodes tumor, malignant; synovial sarcoma; mesothelioma, malignant; dysgerminoma; embryonal carcinoma; teratoma, malignant; struma ovarii, malignant; choriocarcinoma; mesonephroma, malignant; hemangiosarcoma; hemangioendothelioma, malignant; Kaposi's sarcoma; hemangiopericytoma, malignant; lymphangiosarcoma; osteosarcoma; juxtacortical osteosarcoma; chondro sarcoma; chondroblastoma, malignant; mesenchymal chondrosarcoma; giant cell tumor of bone; Ewing's sarcoma; odontogenic tumor, malignant; ameloblastic odonto sarcoma; ameloblastoma, malignant; ameloblastic fibrosarcoma; pinealoma, malignant; chordoma; glioma, malignant; ependymoma; astrocytoma; protoplasmic astrocytoma; fibrillary astrocytoma; astroblastoma; glioblastoma; oligodendroglioma; oligodendroblastoma; primitive neuroectodermal; cerebellar sarcoma; ganglioneuroblastoma; neuroblastoma; retinoblastoma; olfactory neurogenic tumor; meningioma, malignant; neurofibrosarcoma; neurilemmoma, malignant; granular cell tumor, malignant; malignant lymphoma; Hodgkin's disease; hodgkin's; paragranuloma; malignant lymphoma, small lymphocytic; malignant lymphoma, large cell, diffuse; malignant lymphoma, follicular; mycosis fungoides; other specified non-Hodgkin's lymphomas; malignant histiocytosis; multiple myeloma; mast cell sarcoma; immunoproliferative small intestinal disease; leukemia; lymphoid leukemia; plasma cell leukemia; erythroleukemia; lymphosarcoma cell leukemia; myeloid leukemia; basophilic leukemia; eosinophilic leukemia; monocytic leukemia; mast cell leukemia; megakaryoblastic leukemia; myeloid sarcoma; and hairy cell leukemia.

The term "DNA damaging agent" refers to any agent that directly or indirectly damages DNA for which homologous recombination could repair the damage. Specific examples of DNA-damaging agents include alkylating agents, nitrosoureas, anti-metabolites, plant alkaloids, plant extracts and radioisotopes. Specific examples of agents also include DNA-damaging drugs, for example, 5-fluorouracil (5-FU), capecitabine, S-1 (Tegafur, 5-chloro-2,4-dihydroxypyridine and oxonic acid), 5-ethynyluracil, arabinosyl cytosine (ara-C), 5-azacytidine (5-AC), 2',2'-difluoro-2'-deoxycytidine (dFdC), purine antimetabolites (mercaptopurine, azathiopurine, thioguanine), gemcitabine hydrochlorine (Gemzar), pentostatin, allopurinol, 2-fluoro-arabinosyl-adenine (2F-ara-A), hydroxyurea, sulfur mustard (bischloroetyhylsulfide), mechlorethamine, melphalan, chlorambucil, cyclophosphamide, ifosfamide, thiotepa, AZQ, mitomycin C, dianhydrogalactitol, dibromoducitol, alkyl sulfonate (busulfan), nitrosoureas (BCNU, CCNU, 4-methyl CCNU or ACNU), procarbazine, decarbazine, rebeccamycin, anthracycline such as doxorubicin (adriamycin; ADR), daunorubicin (Cerubicine), idarubicin (Idamycin) and epirubicin (Ellence), anthracyclin analogs such as mitoxantrone, actinimycin D, non-intercalating topoisomerase inhibitors such as epipodophyllotoxins (etoposide or VP16, teniposide or VM-26), podophylotoxin, bleomycin (Bleo), pepleomycin, compounds that form adducts with nucleic acid including platinum derivatives, e.g., cisplatin (CDDP), trans analog of cisplatin, carboplatin, iproplatin, tetraplatin and oxaliplatin, as well as camptothecin, topotecan, irinotecan (CPT-11), and SN-38. Specific examples of nucleic acid damaging treatments include radiation e.g., ultraviolet (UV), infrared (IR), or α-, β-, or γ-radiation, as well as environmental shock, e.g., hyperthermia. One of skill in the art can identify and use other DNA-damaging agents and treatments.

D. Chemical Definitions

As used herein, a "small molecule" refers to an organic compound that is either synthesized via conventional organic chemistry methods (e.g., in a laboratory) or found in nature. Typically, a small molecule is characterized in that it contains several carbon-carbon bonds, and has a molecular weight of less than about 1500 grams/mole. In certain embodiments, small molecules are less than about 1000 grams/mole. In certain embodiments, small molecules are less than about 550 grams/mole. In certain embodiments, small molecules are between about 200 and about 550 grams/mole. In certain embodiments, small molecules exclude peptides (e.g., compounds comprising 2 or more amino acids joined by a peptidyl bond). In certain embodiments, small molecules exclude nucleic acids.

As used herein, the term "amino" means —$NH_2$; the term "nitro" means —$NO_2$; the term "halo" or "halogen" designates —F, —Cl, —Br or —I; the term "mercapto" means —SH; the term "cyano" means —CN; the term "azido" means —$N_3$; the term "silyl" means —$SiH_3$, and the term "hydroxy" means —OH. In certain embodiments, a halogen may be —Br or —I.

As used herein, a "monovalent anion" refers to anions of a —1 charge. Such anions are well-known to those of skill in the art. Non-limiting examples of monovalent anions include halides (e.g., F$^-$, Cl$^-$, Br$^-$ and I$^-$), NO$_2^-$, NO$_3^-$, hydroxide (OH$^-$) and azide (N$_3^-$).

As used herein, the structure ===== indicates that the bond may be a single bond or a double bond. Those of skill in the chemical arts understand that in certain circumstances, a double bond between two particular atoms is chemically feasible and in certain circumstances, a double bond is not. The present invention therefore contemplates that a double bond may be formed only when chemically feasible.

The term "alkyl" includes straight-chain alkyl, branched-chain alkyl, cycloalkyl(alicyclic), cyclic alkyl, heteroatom-unsubstituted alkyl, heteroatom-substituted alkyl, heteroatom-unsubstituted $C_n$-alkyl, and heteroatom-substituted $C_n$-alkyl. In certain embodiments, lower alkyls are contemplated. The term "lower alkyl" refers to alkyls of 1-6 carbon atoms (that is, 1, 2, 3, 4, 5 or 6 carbon atoms). The term "heteroatom-unsubstituted $C_n$-alkyl" refers to a radical, having a linear or branched, cyclic or acyclic structure, further having no carbon-carbon double or triple bonds, further having a total of n carbon atoms, all of which are nonaromatic, 3 or more hydrogen atoms, and no heteroatoms. For example, a heteroatom-unsubstituted $C_1$-$C_{10}$-alkyl has 1 to 10 carbon atoms. The groups, —CH$_3$ (Me), —CH$_2$CH$_3$ (Et), —CH$_2$CH$_2$CH$_3$ (n-Pr), —CH(CH$_3$)$_2$ (iso-Pr), —CH(CH$_2$)$_2$ (cyclopropyl), —CH$_2$CH$_2$CH$_2$CH$_3$ (n-Bu), —CH(CH$_3$)CH$_2$CH$_3$ (sec-butyl), —CH$_2$CH(CH$_3$)$_2$ (iso-butyl), —C(CH$_3$)$_3$ (tert-butyl), —CH$_2$C(CH$_3$)$_3$ (neo-pentyl), cyclobutyl, cyclopentyl, and cyclohexyl, are all non-limiting examples of heteroatom-unsubstituted alkyl groups. The term "heteroatom-substituted $C_n$-alkyl" refers to a radical, having a single saturated carbon atom as the point of attachment, no carbon-carbon double or triple bonds, further having a linear or branched, cyclic or acyclic structure, further having a total of n carbon atoms, all of which are nonaromatic, 0, 1, or more than one hydrogen atom, at least one heteroatom, wherein each heteroatom is independently selected from the group consisting of N, O, F, Cl, Br, I, Si, P, and S. For example, a heteroatom-substituted $C_1$-$C_{10}$-alkyl has 1 to 10 carbon atoms. The following groups are all non-limiting examples of heteroatom-substituted alkyl groups: trifluoromethyl, —CH$_2$F, —CH$_2$Cl, —CH$_2$Br, —CH$_2$OH, —CH$_2$OCH$_3$, —CH$_2$OCH$_2$CF$_3$, —CH$_2$OC(O) CH$_3$, —CH$_2$NH$_2$, —CH$_2$NHCH$_3$, —CH$_2$N(CH$_3$)$_2$, —CH$_2$CH$_2$Cl, —CH$_2$CH$_2$OH, CH$_2$CH$_2$OC(O)CH$_3$, —CH$_2$CH$_2$NHCO$_2$C(CH$_3$)$_3$, and —CH$_2$Si(CH$_3$)$_3$.

The term "alkenyl" includes straight-chain alkenyl, branched-chain alkenyl, cycloalkenyl, cyclic alkenyl, heteroatom-unsubstituted alkenyl, heteroatom-substituted alkenyl, heteroatom-unsubstituted $C_n$-alkenyl, and heteroatom-substituted $C_n$-alkenyl. In certain embodiments, lower alkenyls are contemplated. The term "lower alkenyl" refers to alkenyls of 1-6 carbon atoms (that is, 1, 2, 3, 4, 5 or 6 carbon atoms). The term "heteroatom-unsubstituted $C_n$-alkenyl" refers to a radical, having a linear or branched, cyclic or acyclic structure, further having at least one nonaromatic carbon-carbon double bond, but no carbon-carbon triple bonds, a total of n carbon atoms, three or more hydrogen atoms, and no heteroatoms. For example, a heteroatom-unsubstituted $C_2$-$C_{10}$-alkenyl has 2 to 10 carbon atoms. Heteroatom-unsubstituted alkenyl groups include: —CH=CH$_2$ (vinyl), —CH=CHCH$_3$, —CH=CHCH$_2$CH$_3$, —CH$_2$CH=CH$_2$ (allyl), —CH$_2$CH=CHCH$_3$, and —CH=CHC$_6$H$_5$. The term "heteroatom-substituted $C_n$-alkenyl" refers to a radical, having a single nonaromatic carbon atom as the point of attachment and at least one nonaromatic carbon-carbon double bond, but no carbon-carbon triple bonds, further having a linear or branched, cyclic or acyclic structure, further having a total of n carbon atoms, 0, 1, or more than one hydrogen atom, and at least one heteroatom, wherein each heteroatom is independently selected from the group consisting of N, O, F, Cl, Br, I, Si, P, and S. For example, a heteroatom-substituted $C_2$-$C_{10}$-alkenyl has 2 to 10 carbon atoms. The groups, —CH=CHF, —CH=CHCl and —CH=CHBr, are non-limiting examples of heteroatom-substituted alkenyl groups.

The term "aryl" includes heteroatom-unsubstituted aryl, heteroatom-substituted aryl, heteroatom-unsubstituted $C_n$-aryl, heteroatom-substituted $C_n$-aryl, heteroaryl, heterocyclic aryl groups, carbocyclic aryl groups, biaryl groups, and single-valent radicals derived from polycyclic fused hydrocarbons (PAHs). The term "heteroatom-unsubstituted $C_n$-aryl" refers to a radical, having a single carbon atom as a point of attachment, wherein the carbon atom is part of an aromatic ring structure containing only carbon atoms, further having a total of n carbon atoms, 5 or more hydrogen atoms, and no heteroatoms. For example, a heteroatom-unsubstituted $C_6$-$C_{10}$-aryl has 6 to 10 carbon atoms. Non-limiting examples of heteroatom-unsubstituted aryl groups include phenyl (Ph), methylphenyl, (dimethyl)phenyl, —C$_6$H$_4$CH$_2$CH$_3$, —C$_6$H$_4$CH$_2$CH$_2$CH$_3$, —C$_6$H$_4$CH(CH$_3$)$_2$, —C$_6$H$_4$CH(CH$_2$)$_2$, —C$_6$H$_3$(CH$_3$)CH$_2$CH$_3$, —C$_6$H$_4$CH=CH$_2$, —C$_6$H$_4$CH=CHCH$_3$, —C$_6$H$_4$C≡CH, —C$_6$H$_4$C≡CCH$_3$, naphthyl, and the radical derived from biphenyl. The term "heteroatom-substituted $C_n$-aryl" refers to a radical, having either a single aromatic carbon atom or a single aromatic heteroatom as the point of attachment, further having a total of n carbon atoms, at least one hydrogen atom, and at least one heteroatom, further wherein each heteroatom is independently selected from the group consisting of N, O, F, Cl, Br, I, Si, P, and S. For example, a heteroatom-unsubstituted $C_1$-$C_{10}$-heteroaryl has 1 to 10 carbon atoms. Non-limiting examples of heteroatom-substituted aryl groups include the groups: —C$_6$H$_4$F, —C$_6$H$_4$Cl, —C$_6$H$_4$Br, —C$_6$H$_4$I, —C$_6$H$_4$OH, —C$_6$H$_4$OCH$_3$, —C$_6$H$_4$OCH$_2$CH$_3$, —C$_6$H$_4$OC(O)CH$_3$, —C$_6$H$_4$NH$_2$, —C$_6$H$_4$NHCH$_3$, —C$_6$H$_4$N(CH$_3$)$_2$, —C$_6$H$_4$CH$_2$OH, —C$_6$H$_4$CH$_2$OC(O)CH$_3$, —C$_6$H$_4$CH$_2$NH$_2$, —C$_6$H$_4$CF$_3$, —C$_6$H$_4$CN, —C$_6$H$_4$CHO, —C$_6$H$_4$CHO, —C$_6$H$_4$C(O)CH$_3$, —C$_6$H$_4$C(O)C$_6$H$_5$, —C$_6$H$_4$CO$_2$H, —C$_6$H$_4$CO$_2$CH$_3$, —C$_6$H$_4$CONH$_2$, —C$_6$H$_4$CONHCH$_3$, —C$_6$H$_4$CON(CH$_3$)$_2$, furanyl, thienyl, pyridyl, pyrrolyl, pyrimidyl, pyrazinyl, quinolyl, indolyl, and imidazoyl. In certain embodiments, heteroatom-substituted aryl groups are contemplated. In certain embodiments, heteroatom-unsubstituted aryl groups are contemplate. In certain embodiments, an aryl group may be mono-, di-, tri-, tetra- penta-substituted with one or more heteroatom-containing substitutents.

The term "aralkyl" includes heteroatom-unsubstituted aralkyl, heteroatom-substituted aralkyl, heteroatom-unsubstituted $C_n$-aralkyl, heteroatom-substituted $C_n$-aralkyl, heteroaralkyl, and heterocyclic aralkyl groups. In certain embodiments, lower aralkyls are contemplated. The term "lower aralkyl" refers to aralkyls of 7-12 carbon atoms (that is, 7, 8, 9, 10, 11 or 12 carbon atoms). The term "heteroatom-unsubstituted $C_n$-aralkyl" refers to a radical, having a single saturated carbon atom as the point of attachment, further having a total of n carbon atoms, wherein at least 6 of the carbon atoms form an aromatic ring structure containing only carbon atoms, 7 or more hydrogen atoms, and no heteroatoms. For example, a heteroatom-unsubstituted $C_7$-$C_{10}$-aralkyl has 7 to 10 carbon atoms. Non-limiting examples of heteroatom-unsubstituted aralkyls are: phenylmethyl (benzyl, Bn) and phenylethyl. The term "heteroatom-substituted $C_n$-aralkyl" refers to a radical, having a single saturated carbon atom as the point of attachment, further having a total of n carbon atoms, 0, 1, or more than one hydrogen atom, and at least one heteroatom, wherein at least one of the carbon atoms is incorporated an aromatic ring structures, further wherein each heteroatom is independently selected from the group consisting of N, O, F, Cl, Br, I, Si, P, and S. For example, a heteroatom-substituted $C_2$-$C_{10}$-heteroaralkyl has 2 to 10 carbon atoms.

The term "acyl" includes straight-chain acyl, branched-chain acyl, cycloacyl, cyclic acyl, heteroatom-unsubstituted acyl, heteroatom-substituted acyl, heteroatom-unsubstituted $C_n$-acyl, heteroatom-substituted $C_n$-acyl, alkylcarbonyl, alkoxycarbonyl and aminocarbonyl groups. In certain embodiments, lower acyls are contemplated. The term "lower acyl" refers to acyls of 1-6 carbon atoms (that is, 1, 2, 3, 4, 5 or 6 carbon atoms). The term "heteroatom-unsubstituted $C_n$-acyl" refers to a radical, having a single carbon atom of a carbonyl group as the point of attachment, further having a linear or branched, cyclic or acyclic structure, further having a total of n carbon atoms, 1 or more hydrogen atoms, a total of one oxygen atom, and no additional heteroatoms. For example, a heteroatom-unsubstituted $C_1$-$C_{10}$-acyl has 1 to 10 carbon atoms. The groups, —CHO, —C(O)CH$_3$, —C(O)CH$_2$CH$_3$, —C(O)CH$_2$CH$_2$CH$_3$, —C(O)CH(CH$_3$)$_2$, —C(O)CH(CH$_2$)$_2$, —C(O)C$_6$H$_5$, —C(O)C$_6$H$_4$CH$_3$, —C(O)C$_6$H$_4$CH$_2$CH$_3$, and —COC$_6$H$_3$(CH$_3$)$_2$, are non-limiting examples of heteroatom-unsubstituted acyl groups. The term "heteroatom-substituted $C_n$-acyl" refers to a radical, having a single carbon atom as the point of attachment, the carbon atom being part of a carbonyl group, further having a linear or branched, cyclic or acyclic structure, further having a total of n carbon atoms, 0, 1, or more than one hydrogen atom, at least one additional heteroatom, in addition to the oxygen of the carbonyl group, wherein each additional heteroatom is independently selected from the group consisting of N, O, F, Cl, Br, I, Si, P, and S. For example, a heteroatom-substituted $C_1$-$C_{10}$-acyl has 1 to 10 carbon atoms. The groups, —C(O)CH$_2$CF$_3$, —CO$_2$H, —CO$_2^-$, —CO$_2$CH$_3$, —CO$_2$CH$_2$CH$_3$, —CO$_2$CH$_2$CH$_2$CH$_3$, —CO$_2$CH(CH$_3$)$_2$, —CO$_2$CH(CH$_2$)$_2$, —C(O)NH$_2$ (carbamoyl), —C(O)NHCH$_3$, —C(O)NHCH$_2$CH$_3$, —CONHCH(CH$_3$)$_2$, —CONHCH(CH$_2$)$_2$, —CON(CH$_3$)$_2$, and —CONHCH$_2$CF$_3$, are non-limiting examples of heteroatom-substituted acyl groups.

The term "alkoxy" includes straight-chain alkoxy, branched-chain alkoxy, cycloalkoxy, cyclic alkoxy, heteroatom-unsubstituted alkoxy, heteroatom-substituted alkoxy, heteroatom-unsubstituted $C_n$-alkoxy, and heteroatom-substituted $C_n$-alkoxy. In certain embodiments, lower alkoxys are contemplated. The term "lower alkoxy" refers to alkoxys of 1-6 carbon atoms (that is, 1, 2, 3, 4, 5 or 6 carbon atoms). The term "heteroatom-unsubstituted $C_n$-alkoxy" refers to a group, having the structure —OR, in which R is a heteroatom-unsubstituted $C_n$-alkyl, as that term is defined above. Heteroatom-unsubstituted alkoxy groups include: —OCH$_3$, —OCH$_2$CH$_3$, —OCH$_2$CH$_2$CH$_3$, —OCH(CH$_3$)$_2$, and —OCH(CH$_2$)$_2$. The term "heteroatom-substituted $C_n$-alkoxy" refers to a group, having the structure —OR, in which R is a heteroatom-substituted $C_n$-alkyl, as that term is defined above. For example, —OCH$_2$CF$_3$ is a heteroatom-substituted alkoxy group.

The term "alkenyloxy" includes straight-chain alkenyloxy, branched-chain alkenyloxy, cycloalkenyloxy, cyclic alkenyloxy, heteroatom-unsubstituted alkenyloxy, heteroatom-substituted alkenyloxy, heteroatom-unsubstituted $C_n$-alkenyloxy, and heteroatom-substituted $C_n$-alkenyloxy. The term "heteroatom-unsubstituted $C_n$-alkenyloxy" refers to a group, having the structure —OR, in which R is a heteroatom-unsubstituted $C_n$-alkenyl, as that term is defined above. The term "heteroatom-substituted $C_n$-alkenyloxy" refers to a group, having the structure —OR, in which R is a heteroatom-substituted $C_n$-alkenyl, as that term is defined above.

The term "alkynyloxy" includes straight-chain alkynyloxy, branched-chain alkynyloxy, cycloalkynyloxy, cyclic alkynyloxy, heteroatom-unsubstituted alkynyloxy, heteroatom-substituted alkynyloxy, heteroatom-unsubstituted $C_n$-alkynyloxy, and heteroatom-substituted $C_n$-alkynyloxy. The term "heteroatom-unsubstituted $C_n$-alkynyloxy" refers to a group, having the structure —OR, in which R is a heteroatom-unsubstituted $C_n$-alkynyl, as that term is defined above. The term "heteroatom-substituted $C_n$-alkynyloxy" refers to a group, having the structure —OR, in which R is a heteroatom-substituted $C_n$-alkynyl, as that term is defined above.

The term "aryloxy" includes heteroatom-unsubstituted aryloxy, heteroatom-substituted aryloxy, heteroatom-unsubstituted $C_n$-aryloxy, heteroatom-substituted $C_n$-aryloxy, heteroaryloxy, and heterocyclic aryloxy groups. The term "heteroatom-unsubstituted $C_n$-aryloxy" refers to a group, having the structure —OAr, in which Ar is a heteroatom-unsubstituted $C_n$-aryl, as that term is defined above. A non-limiting example of a heteroatom-unsubstituted aryloxy group is —OC$_6$H$_5$. The term "heteroatom-substituted $C_n$-aryloxy" refers to a group, having the structure —OAr, in which Ar is a heteroatom-substituted $C_n$-aryl, as that term is defined above.

The term "aralkyloxy" includes heteroatom-unsubstituted aralkyloxy, heteroatom-substituted aralkyloxy, heteroatom-unsubstituted $C_n$-aralkyloxy, heteroatom-substituted $C_n$-aralkyloxy, heteroaralkyloxy, and heterocyclic aralkyloxy groups. The term "heteroatom-unsubstituted $C_n$-aralkyloxy" refers to a group, having the structure —OAr, in which Ar is a heteroatom-unsubstituted $C_n$-aralkyl, as that term is defined above. The term "heteroatom-substituted $C_n$-aralkyloxy" refers to a group, having the structure —OAr, in which Ar is a heteroatom-substituted $C_n$-aralkyl, as that term is defined above.

The term "acyloxy" includes straight-chain acyloxy, branched-chain acyloxy, cycloacyloxy, cyclic acyloxy, heteroatom-unsubstituted acyloxy, heteroatom-substituted acyloxy, heteroatom-unsubstituted $C_n$-acyloxy, heteroatom-substituted $C_n$-acyloxy, alkylcarbonyloxy, arylcarbonyloxy, alkoxycarbonyloxy, aryloxycarbonyloxy, and carboxylate groups. The term "heteroatom-unsubstituted $C_n$-acyloxy" refers to a group, having the structure —OAc, in which Ac is a heteroatom-unsubstituted $C_n$-acyl, as that term is defined above. For example, —OC(O)CH$_3$ is a non-limiting example of a heteroatom-unsubstituted acyloxy group. The term "heteroatom-substituted $C_n$-acyloxy" refers to a group, having the structure —OAc, in which Ac is a heteroatom-substituted $C_n$-acyl, as that term is defined above. For example, —OC(O)OCH$_3$ and —OC(O)NHCH$_3$ are non-limiting examples of heteroatom-unsubstituted acyloxy groups.

The term "alkylamino" includes straight-chain alkylamino, branched-chain alkylamino, cycloalkylamino, cyclic alkylamino, heteroatom-unsubstituted alkylamino, heteroatom-substituted alkylamino, heteroatom-unsubstituted $C_n$-alkylamino, and heteroatom-substituted $C_n$-alkylamino. The term "heteroatom-unsubstituted $C_n$-alkylamino" refers to a radical, having a single nitrogen atom as the point of attachment, further having one or two saturated carbon atoms attached to the nitrogen atom, further having a linear or branched, cyclic or acyclic structure, containing a total of n carbon atoms, all of which are nonaromatic, 4 or more hydrogen atoms, a total of 1 nitrogen atom, and no additional heteroatoms. For example, a heteroatom-unsubstituted $C_1$-$C_{10}$-alkylamino has 1 to 10 carbon atoms. The term "heteroatom-unsubstituted $C_n$-alkylamino" includes groups, having the structure —NHR, in which R is a heteroatom-unsubstituted $C_n$-alkyl, as that term is defined above. A heteroatom-unsubstituted alkylamino group would include —NHCH$_3$, —NHCH$_2$CH$_3$, —NHCH$_2$CH$_2$CH$_3$, —NHCH(CH$_3$)$_2$, —NHCH(CH$_2$)$_2$, —NHCH$_2$CH$_2$CH$_2$CH$_3$, —NHCH(CH$_3$)CH$_2$CH$_3$, —NHCH$_2$CH(CH$_3$)$_2$, —NHC(CH$_3$)$_3$, —N(CH$_3$)$_2$, —N(CH$_3$)CH$_2$CH$_3$, —N(CH$_2$CH$_3$)$_2$, N-pyrrolidinyl, and N-piperidinyl. The term "heteroatom-substituted $C_n$-alkylamino" refers to a radical, having a single nitrogen atom as the point of attachment, further having one or two saturated carbon atoms attached to the nitrogen atom, no carbon-carbon double or triple bonds, further having a linear or branched, cyclic or acyclic structure, further having a total of n carbon atoms, all of which are nonaromatic, 0, 1, or more than one hydrogen atom, and at least one additional heteroatom, that is, in addition to the nitrogen atom at the point of attachment, wherein each additional heteroatom is independently selected from the group consisting of N, O, F, Cl, Br, I, Si, P, and S. For example, a heteroatom-substituted $C_1$-$C_{10}$-alkylamino has 1 to 10 carbon atoms. The term "heteroatom-substituted $C_n$-alkylamino" includes groups, having the structure —NHR, in which R is a heteroatom-substituted $C_n$-alkyl, as that term is defined above.

The term "alkenylamino" includes straight-chain alkenylamino, branched-chain alkenylamino, cycloalkenylamino, cyclic alkenylamino, heteroatom-unsubstituted alkenylamino, heteroatom-substituted alkenylamino, heteroatom-unsubstituted $C_n$-alkenylamino, heteroatom-substituted $C_n$-alkenylamino, dialkenylamino, and alkyl(alkenyl) amino groups. The term "heteroatom-unsubstituted $C_n$-alkenylamino" refers to a radical, having a single nitrogen atom as the point of attachment, further having one or two carbon atoms attached to the nitrogen atom, further having a linear or branched, cyclic or acyclic structure, containing at least one nonaromatic carbon-carbon double bond, a total of n carbon atoms, 4 or more hydrogen atoms, a total of one nitrogen atom, and no additional heteroatoms. For example, a heteroatom-unsubstituted $C_2$-$C_{10}$-alkenylamino has 2 to 10 carbon atoms. The term "heteroatom-unsubstituted $C_n$-alkenylamino" includes groups, having the structure —NHR, in which R is a heteroatom-unsubstituted $C_n$-alkenyl, as that term is defined above. The term "heteroatom-substituted $C_n$-alkenylamino" refers to a radical, having a single nitrogen atom as the point of attachment and at least one nonaromatic carbon-carbon double bond, but no carbon-carbon triple bonds, further having one or two carbon atoms attached to the nitrogen atom, further having a linear or branched, cyclic or acyclic structure, further having a total of n carbon atoms, 0, 1, or more than one hydrogen atom, and at least one additional heteroatom, that is, in addition to the nitrogen atom at the point of attachment, wherein each additional heteroatom is independently selected from the group consisting of N, O, F, Cl, Br, I, Si, P, and S. For example, a heteroatom-substituted $C_2$-$C_{10}$-alkenylamino has 2 to 10 carbon atoms. The term "heteroatom-substituted $C_n$-alkenylamino" includes groups, having the structure —NHR, in which R is a heteroatom-substituted $C_n$-alkenyl, as that term is defined above.

The term "alkynylamino" includes straight-chain alkynylamino, branched-chain alkynylamino, cycloalkynylamino, cyclic alkynylamino, heteroatom-unsubstituted alkynylamino, heteroatom-substituted alkynylamino, heteroatom-unsubstituted $C_n$-alkynylamino, heteroatom-substituted $C_n$-alkynylamino, dialkynylamino, alkyl(alkynyl) amino, and alkenyl(alkynyl)amino groups. The term "heteroatom-unsubstituted $C_n$-alkynylamino" refers to a radical, having a single nitrogen atom as the point of attachment, further having one or two carbon atoms attached to the nitrogen atom, further having a linear or branched, cyclic or acyclic structure, containing at least one carbon-carbon triple bond, a total of n carbon atoms, at least one hydrogen atoms, a total of one nitrogen atom, and no additional heteroatoms. For example, a heteroatom-unsubstituted $C_2$-$C_{10}$-alkynylamino has 2 to 10 carbon atoms. The term "heteroatom-unsubstituted $C_n$-alkynylamino" includes groups, having the structure —NHR, in which R is a heteroatom-unsubstituted $C_n$-alkynyl, as that term is defined above. The term "heteroatom-substituted $C_n$-alkynylamino" refers to a radical, having a single nitrogen atom as the point of attachment, further having one or two carbon atoms attached to the nitrogen atom, further having at least one nonaromatic carbon-carbon triple bond, further having a linear or branched, cyclic or acyclic structure, and further having a total of n carbon atoms, 0, 1, or more than one hydrogen atom, and at least one additional heteroatom, that is, in addition to the nitrogen atom at the point of attachment, wherein each additional heteroatom is independently selected from the group consisting of N, O, F, Cl, Br, I, Si, P, and S. For example, a heteroatom-substituted $C_2$-$C_{10}$-alkynylamino has 2 to 10 carbon atoms. The term "heteroatom-substituted $C_n$-alkynylamino" includes groups, having the structure NHR, in which R is a heteroatom-substituted $C_n$-alkynyl, as that term is defined above.

The term "arylamino" includes heteroatom-unsubstituted arylamino, heteroatom-substituted arylamino, heteroatom-unsubstituted $C_n$-arylamino, heteroatom-substituted $C_n$-arylamino, heteroarylamino, heterocyclic arylamino, and alkyl (aryl)amino groups. The term "heteroatom-unsubstituted $C_n$-arylamino" refers to a radical, having a single nitrogen atom as the point of attachment, further having at least one aromatic ring structure attached to the nitrogen atom, wherein the aromatic ring structure contains only carbon atoms, further having a total of n carbon atoms, 6 or more hydrogen atoms, a total of one nitrogen atom, and no additional heteroatoms. For example, a heteroatom-unsubstituted $C_6$-$C_{10}$-arylamino has 6 to 10 carbon atoms. The term "heteroatom-unsubstituted $C_n$-arylamino" includes groups, having the structure —NHR, in which R is a heteroatom-unsubstituted $C_n$-aryl, as that term is defined above. The term "heteroatom-substituted $C_n$-arylamino" refers to a radical, having a single nitrogen atom as the point of attachment, further having a total of n carbon atoms, at least one hydrogen atom, at least one additional heteroatoms, that is, in addition to the nitrogen atom at the point of attachment, wherein at least one of the carbon atoms is incorporated into one or more aromatic ring structures, further wherein each additional heteroatom is independently selected from the group consisting of N, O, F, Cl, Br, I, Si, P, and S. For example, a heteroatom-substituted $C_6$-$C_{10}$-arylamino has 6 to 10 carbon atoms. The term "heteroatom-substituted $C_n$-arylamino" includes groups, having the structure —NHR, in which R is a heteroatom-substituted $C_n$-aryl, as that term is defined above.

The term "aralkylamino" includes heteroatom-unsubstituted aralkylamino, heteroatom-substituted aralkylamino, heteroatom-unsubstituted $C_n$-aralkylamino, heteroatom-substituted $C_n$-aralkylamino, heteroaralkylamino, heterocyclic aralkylamino groups, and diaralkylamino groups. The term "heteroatom-unsubstituted $C_n$-aralkylamino" refers to a radical, having a single nitrogen atom as the point of attachment, further having one or two saturated carbon atoms attached to the nitrogen atom, further having a total of n carbon atoms, wherein at least 6 of the carbon atoms form an aromatic ring structure containing only carbon atoms, 8 or more hydrogen atoms, a total of one nitrogen atom, and no additional heteroatoms. For example, a heteroatom-unsubstituted $C_7$-$C_{10}$-aralkylamino has 7 to 10 carbon atoms. The term "heteroatom-unsubstituted $C_n$-aralkylamino" includes groups, having the structure —NHR, in which R is a heteroatom-unsubstituted $C_n$-aralkyl, as that term is defined above. The term "heteroatom-substituted $C_n$-aralkylamino" refers to a radical, having a single nitrogen atom as the point of attachment, further having at least one or two saturated carbon atoms attached to the nitrogen atom, further having a total of n carbon atoms, 0, 1, or more than one hydrogen atom, at least one additional heteroatom, that is, in addition to the nitrogen atom at the point of attachment, wherein at least one of the carbon atom incorporated into an aromatic ring, further wherein each heteroatom is independently selected from the group consisting of N, O, F, Cl, Br, I, Si, P, and S. For example, a heteroatom-substituted $C_7$-$C_{10}$-aralkylamino has 7 to 10 carbon atoms. The term "heteroatom-substituted $C_n$-aralkylamino" includes groups, having the structure —NHR, in which R is a heteroatom-substituted $C_n$-aralkyl, as that term is defined above.

The term "amido" includes straight-chain amido, branched-chain amido, cycloamido, cyclic amido, heteroatom-unsubstituted amido, heteroatom-substituted amido, heteroatom-unsubstituted $C_n$-amido, heteroatom-substituted $C_n$-amido, alkylcarbonylamino, arylcarbonylamino, alkoxycarbonylamino, aryloxycarbonylamino, acylamino, alkylaminocarbonylamino, arylaminocarbonylamino, and ureido groups. The term "heteroatom-unsubstituted $C_n$-amido" refers to a radical, having a single nitrogen atom as the point of attachment, further having a carbonyl group attached via its carbon atom to the nitrogen atom, further having a linear or branched, cyclic or acyclic structure, further having a total of n carbon atoms, 1 or more hydrogen atoms, a total of one oxygen atom, a total of one nitrogen atom, and no additional heteroatoms. For example, a heteroatom-unsubstituted $C_1$-$C_{10}$-amido has 1 to 10 carbon atoms. The term "heteroatom-unsubstituted $C_n$-amido" includes groups, having the structure —NHR, in which R is a heteroatom-unsubstituted $C_n$-acyl, as that term is defined above. The group, —NHC(O)CH$_3$, is a non-limiting example of a heteroatom-unsubstituted amido group. The term "heteroatom-substituted $C_n$-amido" refers to a radical, having a single nitrogen atom as the point of attachment, further having a carbonyl group attached via its carbon atom to the nitrogen atom, further having a linear or branched, cyclic or acyclic structure, further having a total of n aromatic or nonaromatic carbon atoms, 0, 1, or more than one hydrogen atom, at least one additional heteroatom in addition to the oxygen of the carbonyl group, wherein each additional heteroatom is independently selected from the group consisting of N, O, F, Cl, Br, I, Si, P, and S. For example, a heteroatom-substituted $C_1$-$C_{10}$-amido has 1 to 10 carbon atoms. The term "heteroatom-substituted $C_n$-amido" includes groups, having the structure —NHR, in which R is a heteroatom-unsubstituted $C_n$-acyl, as that term is defined above. The group, —NHCO$_2$CH$_3$, is a non-limiting example of a heteroatom-substituted amido group.

The term "alkylthio" includes straight-chain alkylthio, branched-chain alkylthio, cycloalkylthio, cyclic alkylthio, heteroatom-unsubstituted alkylthio, heteroatom-substituted alkylthio, heteroatom-unsubstituted $C_n$-alkylthio, and heteroatom-substituted $C_n$-alkylthio. The term "heteroatom-unsubstituted $C_n$-alkylthio" refers to a group, having the structure —SR, in which R is a heteroatom-unsubstituted $C_n$-alkyl, as that term is defined above. The group, —SCH$_3$, is an example of a heteroatom-unsubstituted alkylthio group. The term "heteroatom-substituted $C_n$-alkylthio" refers to a group, having the structure —SR, in which R is a heteroatom-substituted $C_n$-alkyl, as that term is defined above.

The term "alkenylthio" includes straight-chain alkenylthio, branched-chain alkenylthio, cycloalkenylthio, cyclic alkenylthio, heteroatom-unsubstituted alkenylthio, heteroatom-substituted alkenylthio, heteroatom-unsubstituted $C_n$-alkenylthio, and heteroatom-substituted $C_n$-alkenylthio. The term "heteroatom-unsubstituted $C_n$-alkenylthio" refers to a group, having the structure —SR, in which R is a heteroatom-unsubstituted $C_n$-alkenyl, as that term is defined above. The term "heteroatom-substituted $C_n$-alkenylthio" refers to a group, having the structure —SR, in which R is a heteroatom-substituted $C_n$-alkenyl, as that term is defined above.

The term "alkynylthio" includes straight-chain alkynylthio, branched-chain alkynylthio, cycloalkynylthio, cyclic alkynylthio, heteroatom-unsubstituted alkynylthio, heteroatom-substituted alkynylthio, heteroatom-unsubstituted $C_n$-alkynylthio, and heteroatom-substituted $C_n$-alkynylthio. The term "heteroatom-unsubstituted $C_n$-alkynylthio" refers to a group, having the structure —SR, in which R is a heteroatom-unsubstituted $C_n$-alkynyl, as that term is defined above. The term "heteroatom-substituted $C_n$-alkynylthio" refers to a group, having the structure —SR, in which R is a heteroatom-substituted $C_n$-alkynyl, as that term is defined above.

The term "arylthio" includes heteroatom-unsubstituted arylthio, heteroatom-substituted arylthio, heteroatom-unsubstituted $C_n$-arylthio, heteroatom-substituted $C_n$-arylthio, heteroarylthio, and heterocyclic arylthio groups. The term "heteroatom-unsubstituted $C_n$-arylthio" refers to a group, having the structure —SAr, in which Ar is a heteroatom-unsubstituted $C_n$-aryl, as that term is defined above. The group, —SC$_6$H$_5$, is an example of a heteroatom-unsubstituted arylthio group. The term "heteroatom-substituted $C_n$-arylthio" refers to a group, having the structure —SAr, in which Ar is a heteroatom-substituted $C_n$-aryl, as that term is defined above.

The term "aralkylthio" includes heteroatom-unsubstituted aralkylthio, heteroatom-substituted aralkylthio, heteroatom-unsubstituted $C_n$-aralkylthio, heteroatom-substituted $C_n$-aralkylthio, heteroaralkylthio, and heterocyclic aralkylthio groups. The term "heteroatom-unsubstituted $C_n$-aralkylthio" refers to a group, having the structure —SAr, in which Ar is a heteroatom-unsubstituted $C_n$-aralkyl, as that term is defined above. The group, —SCH$_2$C$_6$H$_5$, is an example of a heteroatom-unsubstituted aralkyl group. The term "heteroatom-substituted $C_n$-aralkylthio" refers to a group, having the structure —SAr, in which Ar is a heteroatom-substituted $C_n$aralkyl, as that term is defined above.

The term "acylthio" includes straight-chain acylthio, branched-chain acylthio, cycloacylthio, cyclic acylthio, heteroatom-unsubstituted acylthio, heteroatom-substituted acylthio, heteroatom-unsubstituted $C_n$-acylthio, heteroatom-substituted $C_n$-acylthio, alkylcarbonyloxy, arylcarbonyloxy, alkoxycarbonyloxy, aryloxycarbonyloxy, and carboxylate groups. The term "heteroatom-unsubstituted $C_n$-acylthio" refers to a group, having the structure —SAc, in which Ac is a heteroatom-unsubstituted $C_n$-acyl, as that term is defined above. The group, —SCOCH$_3$, is an example of a heteroatom-unsubstituted acylthio group. The term "heteroatom-substituted $C_n$-acylthio" refers to a group, having the structure —SAc, in which Ac is a heteroatom-substituted $C_n$-acyl, as that term is defined above.

The term "alkylsilyl" includes straight-chain alkylsilyl, branched-chain alkylsilyl, cycloalkylsilyl, cyclic alkylsilyl, heteroatom-unsubstituted alkylsilyl, heteroatom-substituted alkylsilyl, heteroatom-unsubstituted $C_n$-alkylsilyl, and heteroatom-substituted $C_n$-alkylsilyl. The term "heteroatom-unsubstituted $C_n$-alkylsilyl" refers to a radical, having a single silicon atom as the point of attachment, further having one, two, or three saturated carbon atoms attached to the silicon atom, further having a linear or branched, cyclic or acyclic structure, containing a total of n carbon atoms, all of which are nonaromatic, 5 or more hydrogen atoms, a total of 1 silicon atom, and no additional heteroatoms. For example, a heteroatom-unsubstituted $C_1$-$C_{10}$-alkylsilyl has 1 to 10 carbon atoms. An alkylsilyl group includes dialkylamino groups. The groups, —Si(CH$_3$)$_3$ and —Si(CH$_3$)$_2$C(CH$_3$)$_3$, are non-limiting examples of heteroatom-unsubstituted alkylsilyl groups. The term "heteroatom-substituted $C_n$-alkylsilyl" refers to a radical, having a single silicon atom as the point of attachment, further having at least one, two, or three saturated carbon atoms attached to the silicon atom, no carbon-carbon double or triple bonds, further having a linear or branched, cyclic or acyclic structure, further having a total of n carbon atoms, all of which are nonaromatic, 0, 1, or more than one hydrogen atom, and at least one additional heteroatom, that is, in addition to the silicon atom at the point of attachment, wherein each additional heteroatom is independently selected from the group consisting of N, O, F, Cl, Br, I, Si, P, and S. For example, a heteroatom-substituted $C_1$-$C_{10}$-alkylsilyl has 1 to 10 carbon atoms.

The term "phosphonate" includes straight-chain phosphonate, branched-chain phosphonate, cyclophosphonate, cyclic phosphonate, heteroatom-unsubstituted phosphonate, heteroatom-substituted phosphonate, heteroatom-unsubstituted $C_n$-phosphonate, and heteroatom-substituted $C_n$-phosphonate. The term "heteroatom-unsubstituted $C_n$-phosphonate" refers to a radical, having a single phosphorous atom as the point of attachment, further having a linear or branched, cyclic or acyclic structure, further having a total of n carbon atoms, 2 or more hydrogen atoms, a total of three oxygen atom, and no additional heteroatoms. The three oxygen atoms are directly attached to the phosphorous atom, with one of these oxygen atoms doubly bonded to the phosphorous atom. For example, a heteroatom-unsubstituted $C_0$-$C_{10}$-phosphonate has 0 to 10 carbon atoms. The groups, —P(O)(OH)$_2$, —P(O)(OH)OCH$_3$, —P(O)(OH)OCH$_2$CH$_3$, —P(O)(OCH$_3$)$_2$, and —P(O)(OH)(OC$_6$H$_5$) are non-limiting examples of heteroatom-unsubstituted phosphonate groups. The term "heteroatom-substituted $C_n$-phosphonate" refers to a radical, having a single phosphorous atom as the point of attachment, further having a linear or branched, cyclic or acyclic structure, further having a total of n carbon atoms, 2 or more hydrogen atoms, three or more oxygen atoms, three of which are directly attached to the phosphorous atom, with one of these three oxygen atoms doubly bonded to the phosphorous atom, and further having at least one additional heteroatom in addition to the three oxygen atoms, wherein each additional heteroatom is independently selected from the group consisting of N, O, F, Cl, Br, I, Si, P, and S. For example, a heteroatom-unsubstituted $C_0$-$C_{10}$-phosphonate has 0 to 10 carbon atoms.

The term "phosphinate" includes straight-chain phosphinate, branched-chain phosphinate, cyclophosphinate, cyclic phosphinate, heteroatom-unsubstituted phosphinate, heteroatom-substituted phosphinate, heteroatom-unsubstituted $C_n$-phosphinate, and heteroatom-substituted $C_n$-phosphinate. The term "heteroatom-unsubstituted $C_n$-phosphinate" refers to a radical, having a single phosphorous atom as the point of attachment, further having a linear or branched, cyclic or acyclic structure, further having a total of n carbon atoms, 2 or more hydrogen atoms, a total of two oxygen atom, and no additional heteroatoms. The two oxygen atoms are directly attached to the phosphorous atom, with one of these oxygen atoms doubly bonded to the phosphorous atom. For example, a heteroatom-unsubstituted $C_0$-$C_{10}$-phosphinate has 0 to 10 carbon atoms. The groups, —P(O)(OH)H, —P(O)(OH)CH$_3$, —P(O)(OH)CH$_2$CH$_3$, —P(O)(OCH$_3$)CH$_3$, and —P(O)(OC$_6$H$_5$)H are non-limiting examples of heteroatom-unsubstituted phosphinate groups. The term "heteroatom-substituted $C_n$-phosphinate" refers to a radical, having a single phosphorous atom as the point of attachment, further having a linear or branched, cyclic or acyclic structure, further having a total of n carbon atoms, 2 or more hydrogen atoms, two or more oxygen atoms, two of which are directly attached to the phosphorous atom, with one of these two oxygen atoms doubly bonded to the phosphorous atom, and further having at least one additional heteroatom in addition to the two oxygen atoms, wherein each additional heteroatom is independently selected from the group consisting of N, O, F, Cl, Br, I, Si, P, and S. For example, a heteroatom-unsubstituted $C_0$-$C_{10}$-phosphinate has 0 to 10 carbon atoms.

Any apparently unfulfilled valency is to be understood to be properly filled by hydrogen atom(s). For example, a compound with a substituent of —O or —N is to be understood to be —OH or —NH$_2$, respectively.

Any genus, subgenus, or specific compound discussed herein is specifically contemplated as being excluded from any embodiment described herein.

Compounds described herein may be prepared synthetically using conventional organic chemistry methods known to those of skill in the art and/or are commercially available (e.g., ChemBridge Co., San Diego, Calif.).

The claimed invention is also intended to encompass salts of any of the compounds of the present invention. The term "salt(s)" as used herein, is understood as being acidic and/or basic salts formed with inorganic and/or organic acids and bases. Zwitterions (internal or inner salts) are understood as being included within the term "salt(s)" as used herein, as are quaternary ammonium salts such as alkylammonium salts. Nontoxic, pharmaceutically acceptable salts are preferred, although other salts may be useful, as for example in isolation or purification steps during synthesis. Salts include, but are not limited to, sodium, lithium, potassium, amines, tartrates, citrates, hydrohalides, phosphates and the like. A salt may be a pharmaceutically acceptable salt, for example. Thus, pharmaceutically acceptable salts of compounds of the present invention are contemplated.

The term "pharmaceutically acceptable salts," as used herein, refers to salts of compounds of this invention that are substantially non-toxic to living organisms. Typical pharmaceutically acceptable salts include those salts prepared by reaction of a compound of this invention with an inorganic or organic acid, or an organic base, depending on the substituents present on the compounds of the invention.

Non-limiting examples of inorganic acids which may be used to prepare pharmaceutically acceptable salts include: hydrochloric acid, phosphoric acid, sulfuric acid, hydrobromic acid, hydroiodic acid, phosphorous acid and the like. Examples of organic acids which may be used to prepare pharmaceutically acceptable salts include: aliphatic mono- and dicarboxylic acids, such as oxalic acid, carbonic acid, citric acid, succinic acid, phenyl-heteroatom-substituted alkanoic acids, aliphatic and aromatic sulfuric acids and the like. Pharmaceutically acceptable salts prepared from inorganic or organic acids thus include hydrochloride, hydrobromide, nitrate, sulfate, pyrosulfate, bisulfate, sulfite, bisulfate, phosphate, monohydrogenphosphate, dihydrogenphosphate, metaphosphate, pyrophosphate, hydroiodide, hydrofluoride, acetate, propionate, formate, oxalate, citrate, lactate, p-toluenesulfonate, methanesulfonate, maleate, and the like.

Suitable pharmaceutically acceptable salts may also be formed by reacting the agents of the invention with an organic base such as methylamine, ethylamine, ethanolamine, lysine, ornithine and the like.

Pharmaceutically acceptable salts include the salts formed between carboxylate or sulfonate groups found on some of the compounds of this invention and inorganic cations, such as sodium, potassium, ammonium, or calcium, or such organic cations as isopropylammonium, trimethylammonium, tetramethylammonium, and imidazolium.

Derivatives of compounds of the present invention are also contemplated. In certain aspects, "derivative" refers to a chemically modified compound that still retains the desired effects of the compound prior to the chemical modification. Such derivatives may have the addition, removal, or substitution of one or more chemical moieties on the parent molecule. Non-limiting examples of the types modifications that can be made to the compounds and structures disclosed herein include the addition or removal of lower alkanes such as methyl, ethyl, propyl, or substituted lower alkanes such as hydroxymethyl or aminomethyl groups; carboxyl groups and carbonyl groups; hydroxyls; nitro, amino, amide, and azo groups; sulfate, sulfonate, sulfono, sulfhydryl, sulfonyl, sulfoxido, phosphate, phosphono, phosphoryl groups, and halide substituents. Additional modifications can include an addition or a deletion of one or more atoms of the atomic framework, for example, substitution of an ethyl by a propyl; substitution of a phenyl by a larger or smaller aromatic group. Alternatively, in a cyclic or bicyclic structure, heteroatoms such as N, S, or O can be substituted into the structure instead of a carbon atom.

Compounds employed in methods of the invention may contain one or more asymmetrically-substituted carbon or nitrogen atoms, and may be isolated in optically active or racemic form. Thus, all chiral, diastereomeric, racemic form, epimeric form, and all geometric isomeric forms of a structure are intended, unless the specific stereochemistry or isomeric form is specifically indicated. Compounds may occur as racemates and racemic mixtures, single enantiomers, diastereomeric mixtures and individual diastereomers. In some embodiments, a single diastereomer is obtained. The chiral centers of the compounds of the present invention can have the S- or the R-configuration, as defined by the IUPAC 1974 Recommendations. Compounds may be of the D- or L-form, for example. It is well known in the art how to prepare and isolate such optically active forms. For example, mixtures of stereoisomers may be separated by standard techniques including, but not limited to, resolution of racemic form, normal, reverse-phase, and chiral chromatography, preferential salt formation, recrystallization, and the like, or by chiral synthesis either from chiral starting materials or by deliberate synthesis of target chiral centers.

In addition, atoms making up the compounds of the present invention are intended to include all isotopic forms of such atoms. Isotopes, as used herein, include those atoms having the same atomic number but different mass numbers. By way of general example and without limitation, isotopes of hydrogen include tritium and deuterium, and isotopes of carbon include $^{13}C$ and $^{14}C$.

As noted above, compounds of the present invention may exist in prodrug form. As used herein, "prodrug" is intended to include any covalently bonded carriers which release the active parent drug or compounds that are metabolized in vivo to an active drug or other compounds employed in the methods of the invention in vivo when such prodrug is administered to a subject. Since prodrugs are known to enhance numerous desirable qualities of pharmaceuticals (e.g., solubility, bioavailability, manufacturing, etc.), the compounds employed in some methods of the invention may, if desired, be delivered in prodrug form. Thus, the invention contemplates prodrugs of compounds of the present invention as well as methods of delivering prodrugs. Prodrugs of the compounds employed in the invention may be prepared by modifying functional groups present in the compound in such a way that the modifications are cleaved, either in routine manipulation or in vivo, to the parent compound.

Accordingly, prodrugs include, for example, compounds described herein in which a hydroxy, amino, or carboxy group is bonded to any group that, when the prodrug is administered to a subject, cleaves to form a free hydroxyl, free amino, or carboxylic acid, respectively. Other examples include, but are not limited to, acetate, formate, and benzoate derivatives of alcohol and amine functional groups; and alkyl, carbocyclic, aryl, and alkylaryl esters such as methyl, ethyl, propyl, iso-propyl, butyl, isobutyl, sec-butyl, tert-butyl, cyclopropyl, phenyl, benzyl, and phenethyl esters, and the like.

It should be recognized that the particular anion or cation forming a part of any salt of this invention is not critical, so long as the salt, as a whole, is pharmacologically acceptable. Additional examples of pharmaceutically acceptable salts and their methods of preparation and use are presented in *Handbook of Pharmaceutical Salts: Properties, Selection and Use* (2002), which is incorporated herein by reference.

E. Pharmaceutical Formulations and Administration Thereof

1. Pharmaceutical Formulations and Routes of Administration

Pharmaceutical compositions of the present invention comprise an effective amount of one or more candidate substance or additional agent dissolved or dispersed in a pharmaceutically acceptable carrier. The phrases "pharmaceutical or pharmacologically acceptable" refers to molecular entities and compositions that do not produce an adverse, allergic or other untoward reaction when administered to an animal, such as, for example, a human, as appropriate. The preparation of a pharmaceutical composition that contains at least one candidate substance or additional active ingredient will be known to those of skill in the art in light of the present disclosure, as exemplified by Remington's Pharmaceutical Sciences, 18th Ed. Mack Printing Company, 1990, incorporated herein by reference. Moreover, for animal (e.g., human) administration, it will be understood that preparations should meet sterility, pyrogenicity, general safety and purity standards as required by FDA Office of Biological Standards.

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed. Mack Printing Company, 1990, pp. 1289-1329). Except insofar as any conventional carrier is incompatible with the active ingredient, its use in the therapeutic or pharmaceutical compositions is contemplated.

The compounds of the invention may comprise different types of carriers depending on whether it is to be administered in solid, liquid or aerosol form, and whether it need to be sterile for such routes of administration as injection. The present invention can be administered intravenously, intradermally, intraarterially, intraperitoneally, intralesionally, intracranially, intraarticularly, intraprostaticaly, intrapleurally, intratracheally, intranasally, intravitreally, intravaginally, intrarectally, topically, intratumorally, intramuscularly, systemically, subcutaneously, subconjunctival, intravesicularlly, mucosally, intrapericardially, intraumbilically, intraocularally, orally, locally, via inhalation (e.g., aerosol inhalation), via injection, via infusion, via continuous infusion, via localized perfusion bathing target cells directly, via a catheter, via a lavage, in cremes, in lipid compositions (e.g., liposomes), or by other method or any combination of the foregoing as would be known to one of ordinary skill in the art (see, for example, Remington's Pharmaceutical Sciences, 1990).

The actual dosage amount of a composition of the present invention administered to an animal patient can be determined by physical and physiological factors such as body weight, severity of condition, the type of disease being treated, previous or concurrent therapeutic interventions, idiopathy of the patient and on the route of administration. The practitioner responsible for administration will, in any event, determine the concentration of active ingredient(s) in a composition and appropriate dose(s) for the individual subject.

In certain embodiments, pharmaceutical compositions may comprise, for example, at least about 0.1% of a compound of the present invention. In other embodiments, the compound may comprise between about 2% to about 75% of the weight of the unit, or between about 25% to about 60%, for example, and any range derivable therein. In other non-limiting examples, a dose may also comprise from about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per administration, and any range derivable therein. In non-limiting examples of a derivable range from the numbers listed herein, a range of about 5 mg/kg/body weight to about 100 mg/kg/body weight, about 5 microgram/kg/body weight to about 500 milligram/kg/body weight, etc., can be administered, based on the numbers described above.

In any case, the composition may comprise various antioxidants to retard oxidation of one or more component. Additionally, the prevention of the action of microorganisms can be brought about by preservatives such as various antibacterial and antifungal agents, including but not limited to parabens (e.g., methylparabens, propylparabens), chlorobutanol, phenol, sorbic acid, thimerosal, or combinations thereof.

The candidate substance may be formulated into a composition in a free base, neutral or salt form. Pharmaceutically acceptable salts, include the acid addition salts, e.g., those formed with the free amino groups of a proteinaceous composition, or which are formed with inorganic acids such as for example, hydrochloric or phosphoric acids, or such organic acids as acetic, oxalic, tartaric or mandelic acid. Salts formed with the free carboxyl groups can also be derived from inorganic bases such as for example, sodium, potassium, ammonium, calcium or ferric hydroxides; or such organic bases as isopropylamine, trimethylamine, histidine, or procaine.

In embodiments where the composition is in a liquid form, a carrier can be a solvent or dispersion medium comprising but not limited to, water, ethanol, polyol (e.g., glycerol, propylene glycol, liquid polyethylene glycol, etc.), lipids (e.g., triglycerides, vegetable oils, liposomes) and combinations thereof. The proper fluidity can be maintained, for example, by the use of a coating, such as lecithin; by the maintenance of the required particle size by dispersion in carriers such as, for example liquid polyol or lipids; by the use of surfactants such as, for example hydroxypropylcellulose; or combinations thereof such methods. It may be preferable to include isotonic agents, such as, for example, sugars, sodium chloride or combinations thereof.

In other embodiments, one may use eye drops, nasal solutions or sprays, aerosols or inhalants. Such compositions are generally designed to be compatible with the target tissue type. In a non-limiting example, nasal solutions are usually aqueous solutions designed to be administered to the nasal passages in drops or sprays. Nasal solutions are prepared so that they are similar in many respects to nasal secretions, so that normal ciliary action is maintained. Thus, in certain embodiments the aqueous nasal solutions usually are isotonic or slightly buffered to maintain a pH of about 5.5 to about 6.5. In addition, antimicrobial preservatives, similar to those used in ophthalmic preparations, drugs, or appropriate drug stabilizers, if required, may be included in the formulation. For example, various commercial nasal preparations are known and include drugs such as antibiotics or antihistamines.

In certain embodiments the candidate substance is prepared for administration by such routes as oral ingestion. In these embodiments, the solid composition may comprise, for example, solutions, suspensions, emulsions, tablets, pills, capsules (e.g., hard or soft shelled gelatin capsules), sustained release formulations, buccal compositions, troches, elixirs, suspensions, syrups, wafers, or combinations thereof. Oral compositions may be incorporated directly with the food of the diet. In certain embodiments, carriers for oral administration comprise inert diluents, assimilable edible carriers or combinations thereof. In other aspects of the invention, the oral composition may be prepared as a syrup or elixir. A syrup or elixir, and may comprise, for example, at least one active agent, a sweetening agent, a preservative, a flavoring agent, a dye, a preservative, or combinations thereof.

In certain embodiments an oral composition may comprise one or more binders, excipients, disintegration agents, lubricants, flavoring agents, and combinations thereof. In certain embodiments, a composition may comprise one or more of the following: a binder, such as, for example, gum tragacanth, acacia, cornstarch, gelatin or combinations thereof; an excipient, such as, for example, dicalcium phosphate, mannitol, lactose, starch, magnesium stearate, sodium saccharine, cellulose, magnesium carbonate or combinations thereof; a disintegrating agent, such as, for example, corn starch, potato starch, alginic acid or combinations thereof; a lubricant, such as, for example, magnesium stearate; a sweetening agent, such as, for example, sucrose, lactose, saccharin or combinations thereof; a flavoring agent, such as, for example peppermint, oil of wintergreen, cherry flavoring, orange flavoring, etc.; or combinations thereof the foregoing. When the dosage unit form is a capsule, it may contain, in addition to materials of the above type, carriers such as a liquid carrier. Various other materials may be present as coatings or to otherwise modify the physical form of the dosage unit. For instance, tablets, pills, or capsules may be coated with shellac, sugar, or both.

Additional formulations which are suitable for other modes of administration include suppositories. Suppositories are solid dosage forms of various weights and shapes, usually medicated, for insertion into the rectum, vagina, or urethra. After insertion, suppositories soften, melt or dissolve in the cavity fluids. In general, for suppositories, traditional carriers may include, for example, polyalkylene glycols, triglycerides, or combinations thereof. In certain embodiments, suppositories may be formed from mixtures containing, for example, the active ingredient in the range of about 0.5% to about 10%, and preferably about 1% to about 2%.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and/or the other ingredients. In the case of sterile powders for the preparation of sterile injectable solutions, suspensions or emulsion, certain methods of preparation may include vacuum-drying or freeze-drying techniques which yield a powder of the active ingredient plus any additional desired ingredient from a previously sterile-filtered liquid medium thereof. The liquid medium should be suitably buffered if necessary and the liquid diluent first rendered isotonic prior to injection with sufficient saline or glucose. The preparation of highly concentrated compositions for direct injection is also contemplated, where the use of DMSO as solvent is envisioned to result in extremely rapid penetration, delivering high concentrations of the active agents to a small area.

The composition must be stable under the conditions of manufacture and storage, and preserved against the contaminating action of microorganisms, such as bacteria and fungi. It will be appreciated that endotoxin contamination should be kept minimally at a safe level, for example, less that 0.5 ng/mg protein.

In particular embodiments, prolonged absorption of an injectable composition can be brought about by the use in the compositions of agents delaying absorption, such as, for example, aluminum monostearate, gelatin, or combinations thereof 2. Combination Therapy In some embodiments, it is contemplated that the RAD51 modulators of the invention may be used in conjunction with DNA damaging agents as part of a treatment regimen. This process may involve contacting the cell(s) with the agents at the same time or within a period of time wherein separate administration of the agents produces a desired therapeutic benefit. This may be achieved by contacting the cell, tissue or organism with a single composition or pharmacological formulation that includes two or more agents, or by contacting the cell with two or more distinct compositions or formulations, wherein one composition includes one agent and the other includes another.

Compounds discussed herein may precede, be co-current with and/or follow the other agents by intervals ranging from minutes to weeks. In embodiments where the agents are applied separately to a cell, tissue or organism, one would generally ensure that a significant period of time did not expire between the time of each delivery, such that the agents would still be able to exert an advantageously combined effect on the cell, tissue or organism. For example, in such instances, it is contemplated that one may contact the cell, tissue or organism with two, three, four or more modalities substantially simultaneously (i.e., within less than about a minute) as the candidate substance. In other aspects, one or more DNA damaging agents may be administered or provided within 1 minute, 5 minutes, 10 minutes, 20 minutes, 30 minutes, 45 minutes, 60 minutes, 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 22 hours, 23 hours, 24 hours, 25 hours, 26 hours, 27 hours, 28 hours, 29 hours, 30 hours, 31 hours, 32 hours, 33 hours, 34 hours, 35 hours, 36 hours, 37 hours, 38 hours, 39 hours, 40 hours, 41 hours, 42 hours, 43 hours, 44 hours, 45 hours, 46 hours, 47 hours, 48 hours, 1 day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 1 week, 2 weeks, 3 weeks, 4 weeks, 5 weeks, 6 weeks, 7 weeks, or 8 weeks or more, and any range derivable therein, prior to and/or after administering the RAD51 modulator.

Various combination regimens of the agents may be employed. Non-limiting examples of such combinations are shown below, wherein a compound of the present invention is "A" and a second agent, such as a DNA damaging agent, is "B":

A/B/A B/A/B B/B/A A/A/B A/B/B B/A/A A/B/B/B B/A/B/B

B/B/B/A B/B/A/B A/A/B/B A/B/A/B A/B/B/A B/B/A/A

B/A/B/A B/A/A/B A/A/A/B B/A/A/A A/B/A/A A/A/B/A

In some embodiments, more than one course of therapy may be employed. It is contemplated that multiple courses may be implemented. In certain embodiments, a patient may have previously undergone radiation or chemotherapy for a cancer that turns out to be chemotherapy- or radiation-resistant. Alternatively, a patient may have a recurring cancer that is to be treated with a DNA damaging agent.

F. Organisms and Cell Source

Cells that may be used in some methods can be from a variety of sources. Embodiments include the use of mammalian cells, such as cells from monkeys, chimpanzees, rabbits, mice, rats, ferrets, dogs, pigs, humans, and cows. Alternatively, the cells may be from fruit flies, yeast, or *E. coli*, which are all model systems for evaluating homologous recombination.

Methods can involve cells, tissues, or organs involving the heart, lung, kidney, liver, bone marrow, pancreas, skin, bone, vein, artery, cornea, blood, small intestine, large intestine, brain, spinal cord, smooth muscle, skeletal muscle, ovary, testis, uterus, and umbilical cord.

Moreover, methods can be employed in cells of the following type: platelet, myelocyte, erythrocyte, lymphocyte, adipocyte, fibroblast, epithelial cell, endothelial cell, smooth muscle cell, skeletal muscle cell, endocrine cell, glial cell, neuron, secretory cell, barrier function cell, contractile cell, absorptive cell, mucosal cell, limbus cell (from cornea), stem cell (totipotent, pluripotent or multipotent), unfertilized or fertilized oocyte, or sperm.

Moreover, methods can be implemented with or in plants or parts of plants, including fruit, flowers, leaves, stems, seeds, cuttings. Plants can be agricultural, medicinal, or decorative.

G. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Fluorescence Polarization and Cell-Based Assays

The synthesized compounds were tested for biological activity in a two-stage manner. They were first evaluated for their ability to inhibit the binding of human RAD51 protein to ssDNA. This primary assay utilizes a fluorescence polarization (FP) based method that involves incubation of purified RAD51 protein with oligonucleotides, which are end-labeled with a fluorescent tag. The binding of RAD51 to this substrate ssDNA is quantified as a function of polarization of light emitted by the fluorescent tag. Chemical analogs were then tested further using secondary cell-based assays. Since cell lethality from RI-1 is thought to be a function of cellular RAD51 inhibition for RI-1, $LD_{50}$ values were used as a surrogate measurement of in vivo activity against RAD51 in cells. This cell-based assay was also simultaneously utilized to evaluate for compound-induced sensitization of cells to the cross-linking chemotherapeutic drug MMC, thereby confirming that toxic effects are secondary to HR inhibition.

Example 2

RI-2 Inhibits HR DNA Repair and Sensitizes Cells to Cross-Linking Chemotherapy

Figure 3:
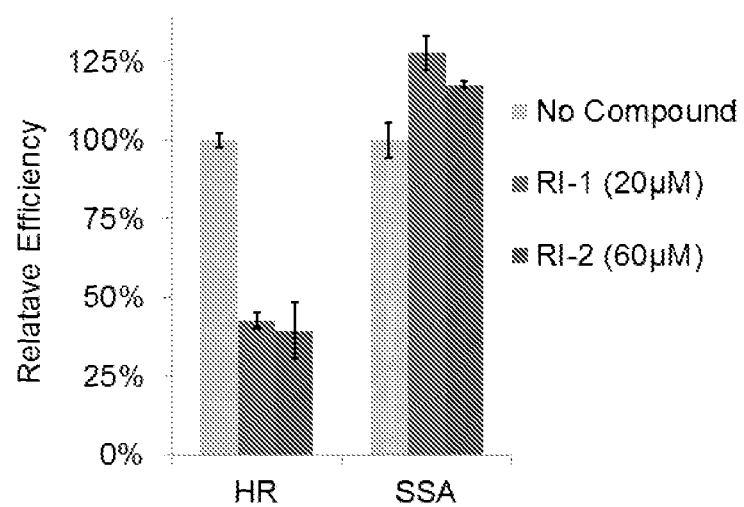
FIG. 3. Relative DNA repair efficiencies. RI-2 inhibits the efficiency of DNA repair in human cells, containing either an HR or SSA reporter. Reporter-containing HEK293 cells were electroporated with an I-SceI endonuclease-expressing plasmid, incubated with compounds as indicated for 24 hours, and subjected to FACS analysis 24 hours thereafter. Incubation of cells with 20 µM RI-1 led to an inhibition of HR and a stimulation of SSA. Despite its lack of Michael acceptor activity, RI-2 at 60 µM also led to an inhibition of HR and a stimulation of SSA by specific inhibition of RAD51 in cells.
Figure 4:
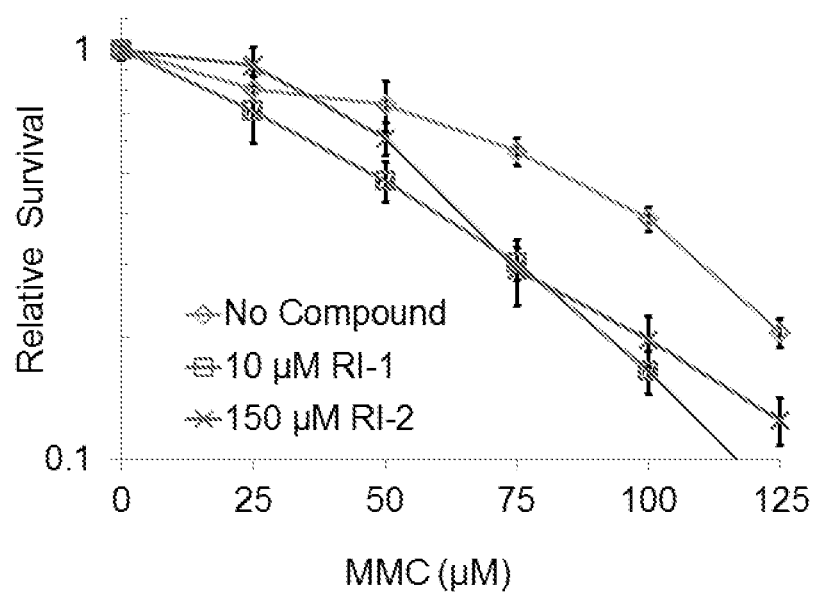
FIG. 4. RI-2 sensitizes human cells to cross-linking chemotherapy. HEK293 cells were sequentially incubated for 24 hours in media containing varying concentrations of MMC, followed by 24 hours in media containing RI-1 or RI-2. Cells were then allowed to grow in drug-free media for an additional 5-7 days. Average survival for each condition is normalized to the MMC-free control of that condition.
Figure 5C:
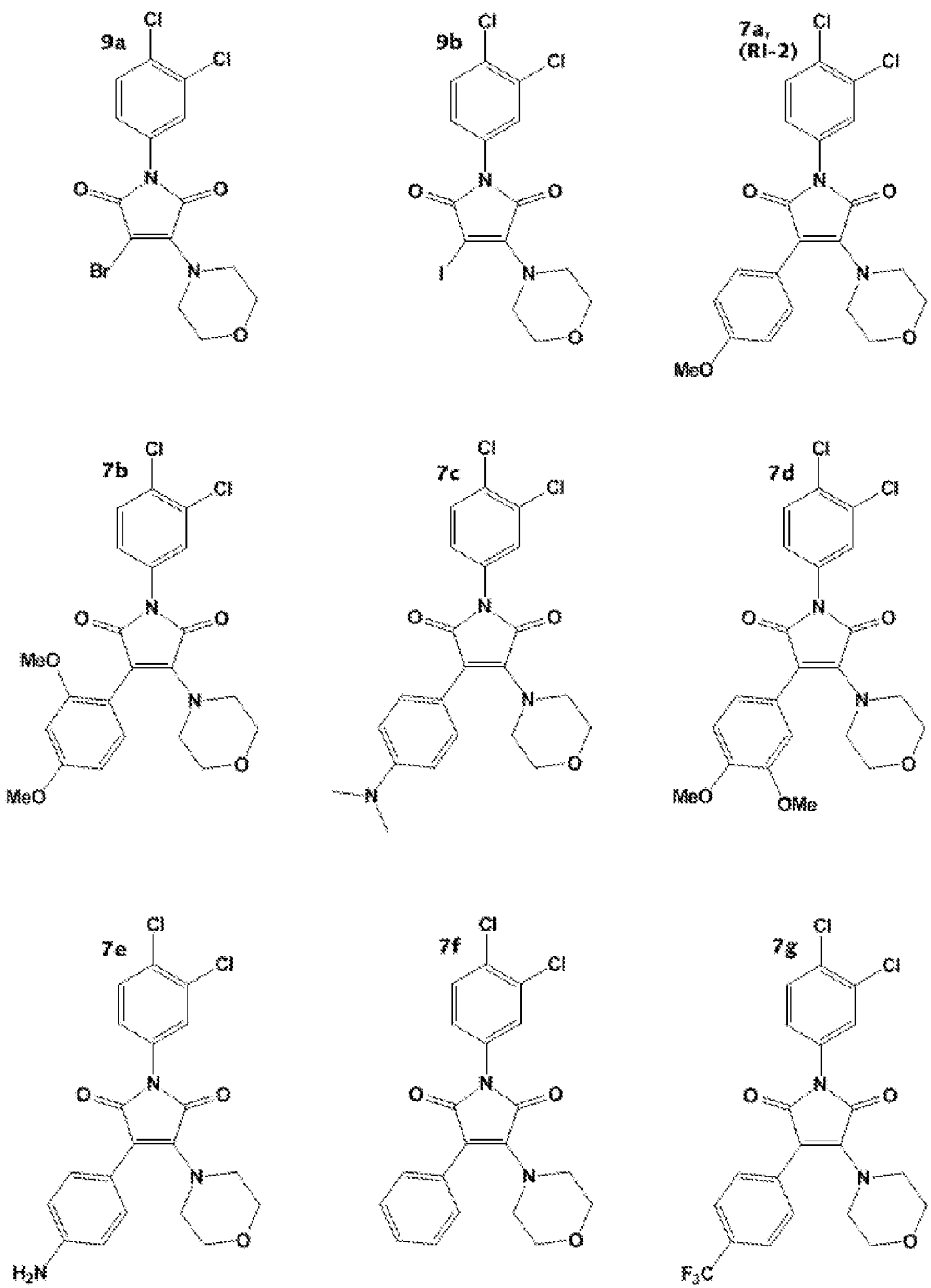
Figure 5D:
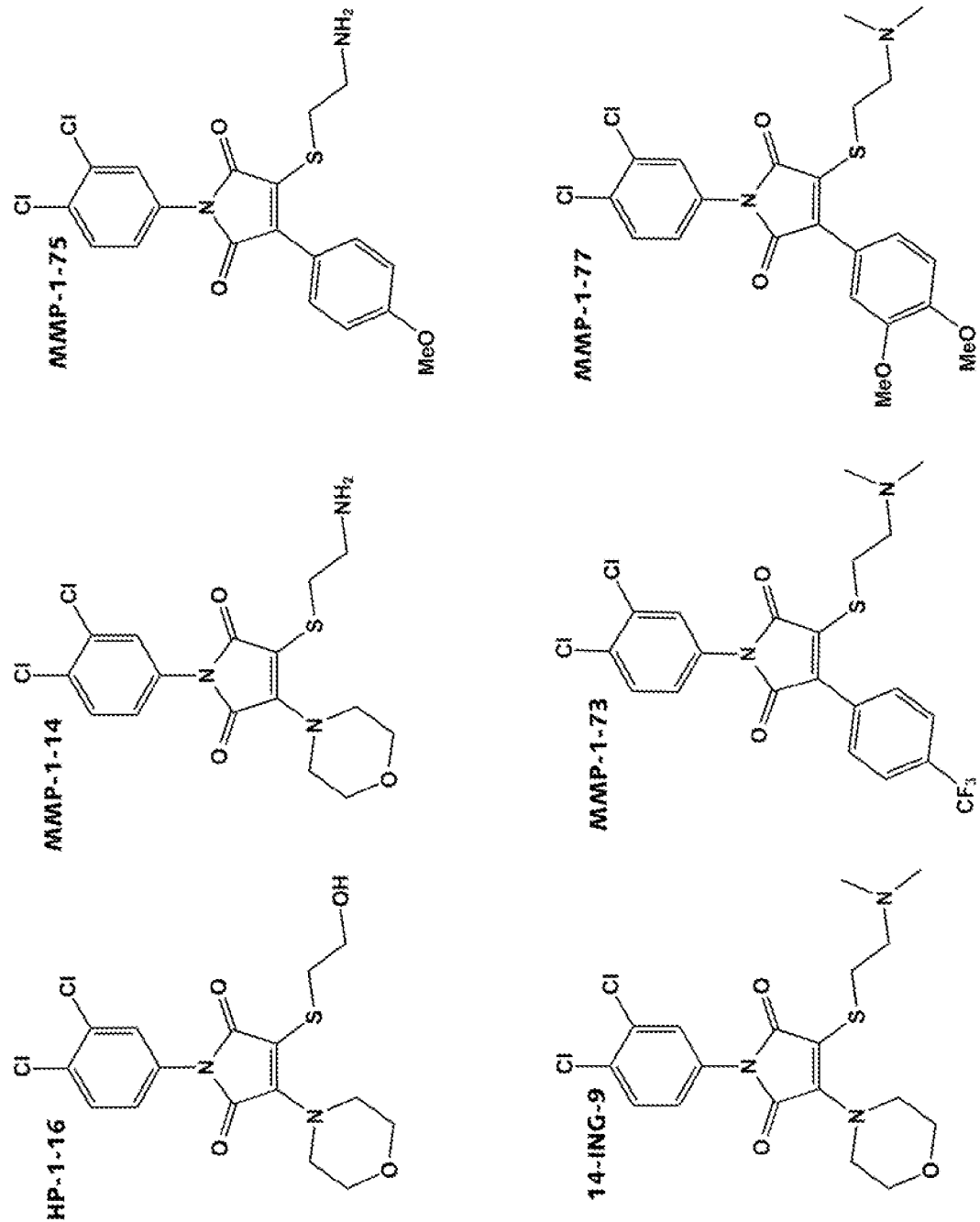
Figure 7A:
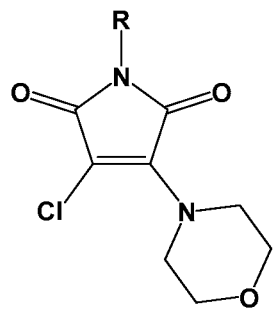
Figure 7B:
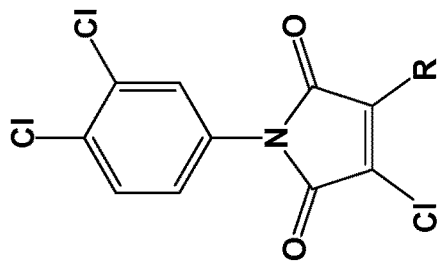
Figure 7D:
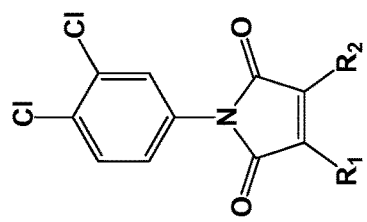
Figure 8:
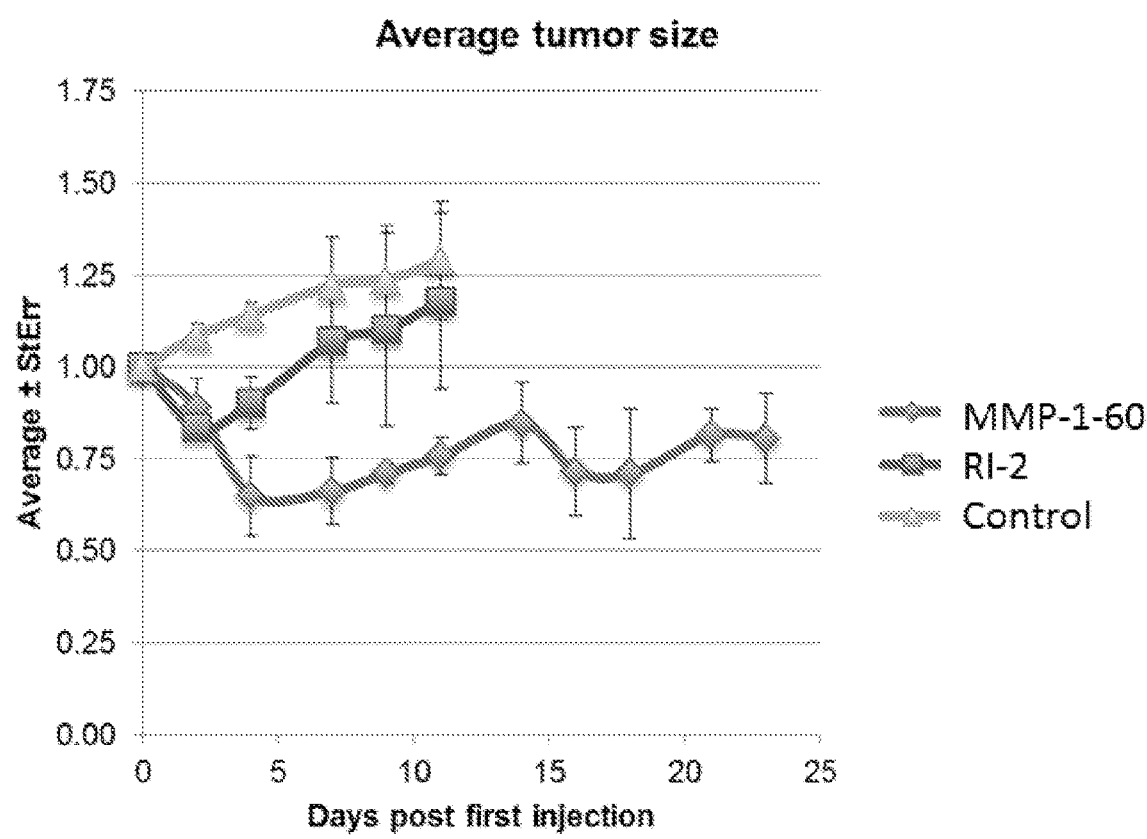
FIG. 8. RS-3 generate anti-tumor responses in a mouse xenograft tumor model. PC3 tumors were induced in the hind limbs of athymic nude mice. Mice were then randomized into three treatment groups. Starting on day 0, mice then received 5 daily intra-peritoneal injections with either RS-2 (12.4 mg/kg), RS-4 (15.7 mg/kg), or vehicle alone control. For both compounds, the daily dose administered to the mice was designed to yield an idealized concentration of 40.8 µM within the aqueous compartment of a mouse, based on an assumption of homogenous distribution across a 21 gm animal that is composed of 70% water.

To demonstrate that RI-2 is capable of gaining intracellular access and specifically inhibiting RAD51 in cells, the compound was tested in human cells that contain integrated reporter constructs that quantify the efficiency of specific DNA repair pathways. The reporter construct that measures HR repair consists of two non-functional copies of green fluorescence protein (GFP), one of which is interrupted by an I-SceI endonuclease site. Induction of a DNA break at the I-SceI site can lead to repair by homologous gene conversion that generates a functional copy of GFP (Pierce et al., 1999). A second parallel assay makes use of cells that contain a different reporter that measures single-strand annealing (SSA), which is an alternative method of re-ligating DNA when HR cannot be completed. SSA efficiency is known to be elevated in situations where RAD51 function has been disrupted (Mansour et al., 2008, Stark et al., 2004, and Bennardo et al., 2008). Consistent with our prior report (Budke et al., 2012), incubation of cells with 20 μM RI-1 led to an inhibition of HR and a stimulation of SSA (FIG. 3). RI-2 at 60 μM was capable of generating very similar effects. This suggests that RI-2 can indeed generate specific inhibition of RAD51 in cells, even though this compound lacks the Michael acceptor reactivity of RI-1.

Example 3

DNA Binding Assay

Human RAD51 protein was prepared as previously described (Budke et al., 2012). RAD51 was incubated with 100 nM (nucleotide concentration) of a 45-mer oligo-dT 5' Alexa 488 end-labeled substrate. Binding was measured as a function of fluorescence polarization (FP) of the Alexa 488 tag. 50 μl reactions were performed in 20 mM HEPES, pH 7.5, 2 mM ATP, 10 mM $MgCl_2$, 30 mM NaCl, 2% glycerol, 250 μM BSA, and 4% DMSO. Black polystyrene flat-bottom 384-well reaction plates were read using a Tecan Infinite F200 Pro plate reader, equipped with 485(20)/535 (25) FP filters. For experiments used to determine $IC_{50}$ values, RAD51 concentrations (typically 190-290 nM) were selected to generate FP signal of 50-80% maximum in the absence of any inhibitory compound. Reported $IC_{50}$ values represent the mean result of at least three replicate wells, and reported errors connote standard deviation.

Example 4

DNA Binding Competition Assays

Using a previously described method, human RAD51 protein was prepared with an N-terminal biotin tag (Jayathilaka et al., 2008). The tag is linked to the protein by a peptide sequence recognized by the Tobacco Etch Virus (TEV) protease. Tagged RAD51 was immobilized on streptavidin-conjugated polyacrylamide beads (Ultralink, Pierce) and incubated for 30 min at 37° C. with candidate compounds in 20 mM HEPES, pH 7.5, 30 mM NaCl, 2% glycerol, 4% DMSO. The polyacrylamide beads were then washed twice with ice-cold wash buffer (20 mM Tris-HCl, pH 8.0, 300 mM NaCl) containing 4% DMSO and then once with ice-cold wash buffer without DMSO. RAD51 protein was subsequently eluted from beads with TEV protease (gift from Phoebe Rice) and analyzed for DNA binding activity using the above FP-based DNA binding assay.

Example 5

Cell Toxicity Assays

HEK293 cells were plated into 96-well tissue culture plates at a density of 300 cells per well in the presence or absence of 50 nM MMC (Ben Venue Laboratories) for 24 hours at 37° C., 5% $CO_2$. Media was subsequently replaced with fresh media containing 0.5% DMSO plus a candidate compound for an additional 24 hours. Compounds were then removed, and cultures were allowed to grow to a 50-70% confluence. Average survival from at least three replicates was measured using CellGlo reagent (Promega) or via a previously described sulforhodamine B method (Jayathilaka et al., 2008). Compounds were deemed successful in sensitizing cells to MMC if they generated significantly greater toxicity in the presence of MMC relative to the absence of MMC. Specifically, sensitization was scored as a "+" when non-overlapping standard errors were observed for at least two pairs of compound doses.

Example 6

Quantification of HR and SSA Efficiencies in Cells

HEK293 cells stably transfected with the DR-GFP or SA-GFP reporters were provided by Jeremy Stark (Bennardo et al., 2008). 0.5-1.0×107 cells at 80% confluence were electroporated with 30-60 μg pCβASce (or pCAGGS) in 4 mm cuvettes, using the following settings: 240-350 V, 975 μF. Cells were transferred into the appropriate complete growth medium and allowed to grow for 24 hours in the presence or absence of a candidate compound. Compounds were removed and cells were incubated for an additional 24 hours in normal media, following which they were analyzed with a Becton-Dickinson FACScan. Live cells were collected based on size/complexity and 7-aminoactinomycin D (7-AAD) exclusion. The fraction of live cells exhibiting GFP positivity is displayed, and error bars denote standard error.

Example 7

Glutathione Stability Experiments

Compound (10 mg) and L-glutathione (5 mol equiv) were placed in a round-bottomed flask under argon and dissolved in DMSO (1 mL). The reaction was heated to 37° C. and stirred. Aliquots of the reaction mixture were removed every hour, including one at t=0 min, and analyzed by HPLC. Ratio of substrate and glutathione adduct was recorded and the expected glutathione adduct was then identified using mass spectrometry Example 8

General Information for Synthetic Procedures $^1$H NMR and $^{13}$C NMR spectra were obtained using a Bruker spectrometer with TMS as an internal standard. The following standard abbreviations indicating multiplicity were used: s=singlet, d=doublet, t=triplet, m=multiplet, and br=broad. HRMS experiments were carried out using a Shimadzu IT-TOF instrument with MeCN and $H_2O$ spiked with 0.1% formic acid as the mobile phase. Reaction progress was monitored by TLC using precoated silica gel plates (Merck silica gel 60 F254, 250 μm thickness). Automated column chromatography was performed using the CombiFlash Rf apparatus available from Teledyne ISCO and prepacked cartridges (50 g) loaded with Merck silica gel (40-60 mesh) along with the following conditions: Gradient: 100% hexane, 5 min; 0-50% EtOAc/hexane, 25 min; 50% EtOAc/hexane, 5 min. Flow rate=40 mL/min with wavelength monitoring at 254 and 280 nm. Preparatory HPLC was carried out using a Shimadzu preparative liquid chromatograph with the following specifications: Column: ACE 5 AQ (150×21.2 mm) with 5 μm particle size. Gradient: 25-100% MeOH/$H_2O$, 30 min; 100% MeOH, 5 min; 100-25% MeOH/$H_2O$, 4 min; 25% MeOH/$H_2O$, 1 min. Flow rate=17 mL/min with wavelength monitoring at 254 and 280 nm. Both solvents were spiked with 0.05% TFA. Resin bound bicarbonate was used to neutralize residual trifluoroacetic acid remaining from preparatory HPLC purification. Analytical HPLC was carried out using an Agilent 1100 series instrument with the following specifications: Column: Luna 5μ C18(2) 100 A (150×4.60 mm) with 5 μm particle size. Flow rate=1.4 mL/min with wavelength monitoring at 254 nm. Gradient: 10-100% MeOH/$H_2O$, 18 min; 100% MeOH, 3 min; 100-10% MeOH/$H_2O$, 3 min; 10% MeOH/$H_2O$, 5 min. Both solvents were spiked with 0.05% TFA. The purity of all tested compounds was ≥95%.

Example 9

General Procedures for Synthesis of RAD51 Inhibitors (Scheme 1)

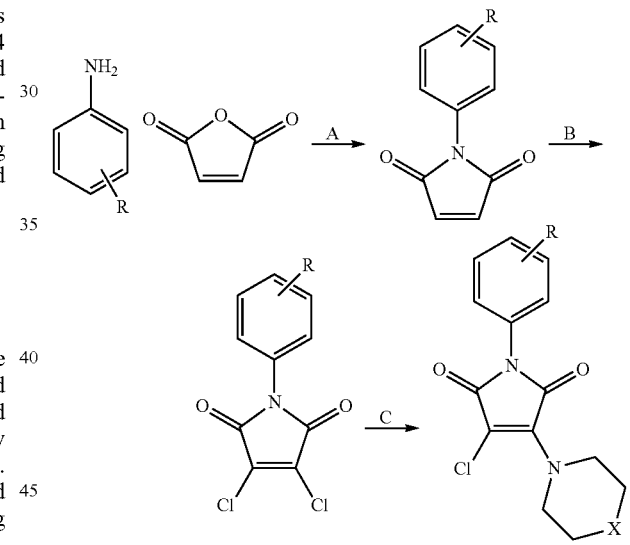

General Procedure A: Maleic anhydride was placed in a round-bottomed flask and to it was added anhydrous $Et_2O$ (2 mL/mmol) at RT. Upon complete dissolution of the maleic anhydride, the appropriate substituted aniline (1.1 mol equiv) dissolved in anhydrous $Et_2O$ (1 mL/mmol) was added dropwise at RT. The reaction was stirred for approximately 2 h resulting in the formation of a white precipitate. The reaction was then concentrated in vacuo, cooled in an ice bath and the N-substituted maleanic acid precipitate was isolated by filtration. The filter cake was then added to a round-bottomed flask charged with sodium acetate (1 mol equiv) and acetic anhydride (0.5 mL/mmol). The reaction was heated to 100° C. and stirred for 20-30 min after which it was cooled to room temperature and poured into ice water (50 mL). The organic products were extracted with EtOAc (3×15 mL), washed with water (3×15 mL) and brine (15 mL), dried with anhydrous $Na_2SO_4$, filtered and concentrated in vacuo. The resulting product was then purified using automated column chromatography.

General Procedure B: The appropriate maleimide was placed in a round-bottomed flask and dissolved in thionyl chloride (1 mL/mmol) at RT. The reaction was cooled to 0° C. in an ice bath and then pyridine (2.1 mol equiv) was added dropwise. The reaction was stirred at 0° C. for 15 min after which it was removed from the ice bath and heated at reflux for 1 h. The reaction was then cooled to RT and excess thionyl chloride was removed in vacuo. The resulting residue was taken up in $CHCl_3$ (30 mL), washed with 1N HCl (3×10 mL) and brine (15 mL), dried with anhydrous $Na_2SO_4$, filtered and concentrated in vacuo. The resulting 3,4-dichloromaleimide was then purified by automated column chromatography.

General Procedure C: The appropriate 3,4-dihalomaleimide was placed in a round-bottomed flask and dissolved in DCM (3 mL/mmol). To it was added either morpholine or N-methylpiperazine (2 mol equiv) at RT and the reaction was stirred for approximately 2 h. Upon addition of the amine, the reaction turned from clear to yellow and a yellow precipitate formed. When the reaction was complete as evidenced by TLC, the reaction was poured into water (15 mL) and the organic products were extracted with DCM (3×15 mL). The combined organic extracts were washed with brine (15 mL), dried with anhydrous $Na_2SO_4$, filtered and concentrated in vacuo. The crude product was then dissolved in DMF and purified by preparatory HPLC.

Example 10

General Procedures for Synthesis of RAD51 Inhibitors (Scheme 2)

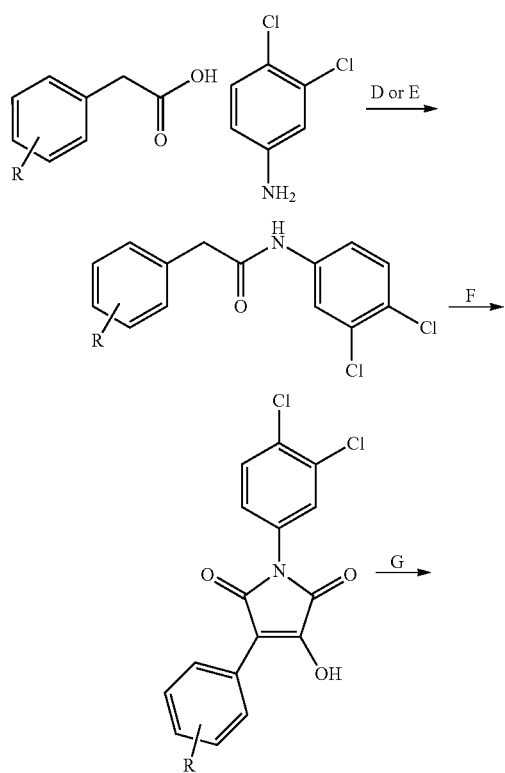

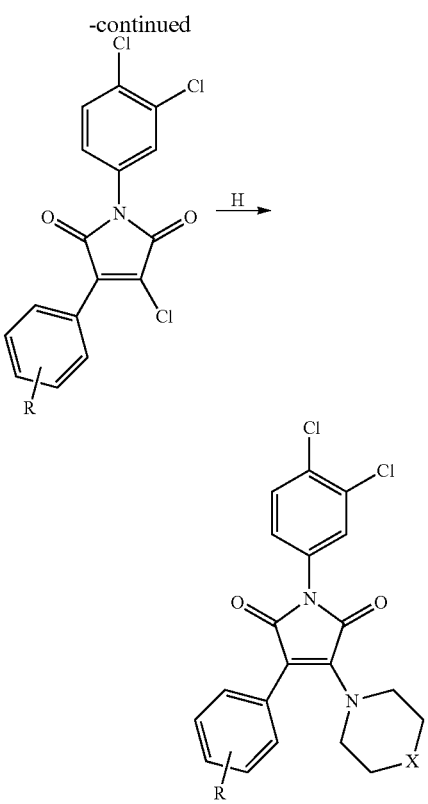

General Procedure D: The appropriate phenylacetic acid was placed in a two-necked round-bottomed flask fitted with a condenser under argon Anhydrous THF (2 mL/mmol) was added followed by three drops of anhydrous DMF after which the reaction was cooled to 0° C. in an ice bath. Oxalyl chloride (2 mol equiv) was added dropwise to the reaction which was then removed from the ice bath and heated to 80° C. for 15 min. Upon completion as evidenced by TLC, the reaction was cooled to RT and the volatiles were removed in vacuo. The freshly obtained acid chloride was then placed under argon and dissolved in anhydrous THF (2 mL/mmol). The appropriate aniline (1.2 mol equiv) dissolved in anhydrous THF (1 mL/mmol) was added followed by triethylamine (1 mol equiv) dropwise at RT. The reaction was then stirred at RT for 2 h after which water (15 mL) was added and the organic products were extracted with EtOAc (3×15 mL). The combined organic fractions were washed with brine (15 mL), dried with anhydrous $Na_2SO_4$, filtered and concentrated in vacuo. The desired amide product was purified by automated column chromatography.

General Procedure E: The appropriate phenylacetic acid, aniline (1 mol equiv), EDCl (1.2 molar equiv) and DMAP (0.1 mol equiv) were placed in a round-bottomed flask under argon and dissolved in anhydrous DCM (5 mL/mmol) at RT. The reaction was then stirred at RT overnight (approximately 16 h) after which water (15 mL) was added and the organic layer was isolated. The aqueous layer was further extracted with DCM (2×15 mL) and the combined organic fractions were washed water (2×20 mL) and brine (15 mL), dried with anhydrous $Na_2SO_4$, filtered and concentrated in vacuo. The desired amide product was then purified by automated column chromatography.

General Procedure F: The respective amide was placed in a round-bottomed flask under argon and dissolved in anhydrous THF (5 mL/mmol). The reaction was cooled to 0° C.

with an ice bath and then diethyl oxalate (2 mol equiv) was added after which potassium tert-butoxide (2.5 mol equiv) dissolved/suspended in anhydrous THF (3 mL/mmol) was added dropwise. The reaction was allowed to warm to RT and then stirred for 2 h. After 2 h, the reaction was poured into ice water (50 mL) and the pH was adjusted to approximately 3 with 1N HCl. The organic products were extracted with EtOAc (3×20 mL) and the combined organic extracts were washed with brine (15 mL), dried with anhydrous $Na_2SO_4$, filtered and concentrated in vacuo. The resulting maleimide product was purified by washing with MeOH.

General Procedure G: The appropriate alcohol was dissolved in DCM (2 mL/mmol) and DMF (2 mL/mmol) at RT. Then, oxalyl chloride (1.1 mol equiv) dissolved in DCM (2 mL/mmol) was added dropwise to the reaction at RT. The reaction was stirred for approximately 10 min and then poured into ice water (30 mL). The organic products were extracted with DCM (3×15 mL), washed with water (3×10 mL) and brine (15 mL), dried with anhydrous $Na_2SO_4$, filtered and concentrated in vacuo. The desired chloromaleimide product was purified by washing with MeOH.

General Procedure H: The appropriate chloromaleimide and either morpholine or N-methylpiperazine (2 mol equiv) were dissolved in anhydrous DMF (3 mL/mmol) and sealed inside a microwave reactor vessel. The reaction was then heated to 150° C. for 10 min after which the reaction was cooled to RT and poured into ice water (15 mL). The organic products were extracted with EtOAc (3×15 mL), washed with water (10 mL) and brine (10 mL), dried with $Na_2SO_4$, filtered and concentrated in vacuo. The desired final product was then purified by preparatory HPLC.

Example 11

Procedures for the Synthesis of RAD51 Derivatives 1-(2,3-Dichlorophenyl)-1H-pyrrole-2,5-dione (1d): The title compound was synthesized from maleic anhydride (2.5 g, 26 mmol) and 2,3-dichloroaniline (4.5 g, 28 mmol) according to general procedure A and isolated as an off-white solid (2.3 g, 37%). $^1$H-NMR (400 MHz, $CDCl_3$): δ 7.58 (dd, J=1.5 Hz, J=6.7 Hz, 1H), 7.33 (t, J=8.0 Hz, 1H), 7.21 (dd, J=1.5 Hz, J=6.4 Hz, 1H), 6.91 (s, 2H). $^{13}$C-NMR (100 MHz, $CDCl_3$): δ 168.4, 134.6, 134.3, 132.2, 131.5, 130.7, 129.0, 127.7. ESI-HRMS: calc. for $C_{10}H_5Cl_2NO_2$: [M+H]$^+$=m/z 241.9770, found: [M+H]$^+$=m/z 241.9776.

1-(3,4-Difluorophenyl)-1H-pyrrole-2,5-dione (1e): The title compound was synthesized from maleic anhydride (1.5 g, 15 mmol) and 3,4-difluoroaniline (2.2 g, 17 mmol) according to general procedure A and isolated as an off-white solid (2.6 g, 82%). $^1$H-NMR (400 MHz, $CDCl_3$): δ 7.28 (m, 2H), 7.16 (m, 1H), 6.88 (s, 2H). $^{13}$C-NMR (100 MHz, $CDCl_3$): δ 168.5, 150.7 (dd, J=14.0 Hz, J=38.7 Hz), 148.2 (dd, J=13.9 Hz, J=39.5 Hz), 133.9, 127.0 (dd, J=3.6 Hz, J=4.4 Hz), 121.7 (d, J=4.0 Hz, J=2.6 Hz), 117.2 (d, J=18.4 Hz), 115.1 (d, J=20.2 Hz). ESI-HRMS: calc. for $C_{10}H_5F_2NO_2$: [M+H]$^+$=m/z 210.0361, found: [M+H]$^+$=m/z 210.0370.

1-(3-Chloro-4-fluorophenyl)-1H-pyrrole-2,5-dione (1f): The title compound was synthesized from maleic anhydride (1.5 g, 15 mmol) and 3-chloro-4-fluoroaniline (2.4 g, 17 mmol) according to general procedure A and isolated as a light-yellow solid (3.1 g, 89%). $^1$H-NMR (400 MHz, $CDCl_3$): δ 7.48 (dd, J=2.2 Hz, J=4.1 Hz, 1H), 7.28 (m, 2H), 6.88 (s, 2H). $^{13}$C-NMR (100 MHz, $CDCl_3$): δ 168.5, 156.9 (d, J=250.3 Hz), 133.9, 127.8, 127.3 (d, J=3.7 Hz), 125.4 (d, J=7.7 Hz), 121.2 (d, J=19.0 Hz), 116.5 (d, J=22.3 Hz). ESI-HRMS: calc. for $C_{10}H_5ClFNO_2$: [M+H]$^+$=m/z 226.0066, found: [M+H]$^+$=m/z 226.0071.

1-(4-Chloro-3-fluorophenyl)-1H-pyrrole-2,5-dione (1g): The title compound was synthesized from maleic anhydride (0.15 g, 1.5 mmol) and 4-chloro-3-fluoroaniline (0.25 g, 1.7 mmol) according to general procedure A and isolated as a light-yellow solid (0.23 g, 65%). $^1$H-NMR (400 MHz, $CDCl_3$): δ 7.50 (t, J=8.3 Hz, 1H), 7.31 (dd, J=2.3 Hz, J=7.5 Hz, 1H), 7.21 (dq, J=1.2 Hz, J=5.3 Hz, 1H), 6.89 (s, 2H). $^{13}$C-NMR (100 MHz, $CDCl_3$): δ 168.7, 157.9 (d, J=249.7 Hz), 134.3, 130.9 (d, J=9.3 Hz), 130.7, 121.8 (d, J=3.9 Hz), 120.3 (d, J=17.6 Hz), 114.2 (d, J=24.4 Hz). ESI-HRMS: calc. for $C_{10}H_5ClFNO_2$: [M+H]$^+$=m/z 226.0066, found: [M+H]$^+$=m/z 226.0070.

1-(3-Bromo-4-chlorophenyl)-1H-pyrrole-2,5-dione (1h): The title compound was synthesized from maleic anhydride (0.11 g, 1.1 mmol) and 3-bromo-4-chloroaniline (0.26 g, 1.2 mmol) according to general procedure A and isolated as an off-white solid (0.30 g, 94%). $^1$H-NMR (400 MHz, $CDCl_3$): δ 7.72 (s, 1H), 7.56 (d, J=8.5 Hz, 1H), 7.43 (d, J=8.4 Hz, 1H), 6.89 (s, 2H). $^{13}$C-NMR (100 MHz, $CDCl_3$): δ 168.7, 134.4, 133.9, 130.63, 130.55, 130.49, 125.5, 122.7. ESI-HRMS: calc. for $C_4H_6NO_7Cl_3$: [M+H]$^+$=285.9283 m/z, found: [M+H]$^+$=m/z 285.9277 m/z.

1-(4-Bromo-3-chlorophenyl)-1H-pyrrole-2,5-dione (1i): The title compound was synthesized from maleic anhydride (0.44 g, 4.5 mmol) and 4-bromo-3-chloroaniline (1.0 g, 4.9 mmol) according to general procedure A and isolated as a brown solid (1.2 g, 97%). $^1$H-NMR (400 MHz, $CDCl_3$): δ 7.71 (d, J=8.6 Hz, 1H), 7.56 (m, 1H), 7.22 (m, 1H), 6.89 (s, 2H). $^{13}$C-NMR (100 MHz, $CDCl_3$): δ 168.7, 135.0, 134.4, 134.0, 131.3, 127.3, 124.9, 121.6. ESI-HRMS: calc. for $C_{10}H_5BrClNO_2$: [M−H]$^−$=m/z 283.9119, found: [M−H]$^−$=m/z 283.9123.

1-(3,4-Dichlorophenyl)-1H-pyrrole-2,5-dione (1j): The title compound was synthesized from maleic anhydride (2.5 g, 26 mmol) and 3,4-dichloroaniline (4.5 g, 28 mmol) according to general procedure A and isolated as an off-white solid (5.6 g, 91%). $^1$H-NMR (400 MHz, $CDCl_3$): δ 7.55 (m, 2H), 7.24 (d, J=9.1 Hz, 1H), 6.89 (s, 2H). $^{13}$C-NMR (100 MHz, $CDCl_3$): δ 168.3, 134.0, 132.7, 131.5, 130.3, 130.2, 127.1, 124.5. ESI-HRMS: calc. for $C_{10}H_5Cl_2NO_2$: [M+H]$^+$=m/z 241.9770, found: [M+H]$^+$=m/z 241.9762.

3,4-Dichloro-1-(2,3-dichlorophenyl)-1H-pyrrole-2,5-dione (2d): The title compound was synthesized from 1-(2,3-dichlorophenyl)-1H-pyrrole-2,5-dione (1d) (1.0 g, 4.1 mmol) according to general procedure B and isolated as a beige solid (1.0 g, 81%). $^1$H-NMR (400 MHz, $CDCl_3$): δ 7.64 (dd, J=1.3 Hz, J=6.8 Hz, 1H), 7.37 (t, J=8.0 Hz, 1H), 7.25 (m, 1H). $^{13}$C-NMR (100 MHz, $CDCl_3$): δ 161.0, 134.6, 134.0, 132.3, 132.1, 129.9, 128.8, 127.9. ESI-HRMS: calc. for $C_{10}H_3Cl_4NO_2$: [M+H]$^+$=m/z 309.8991, found: [M+H]$^+$=m/z 309.8998.

3,4-Dichloro-1-(3,4-difluorophenyl)-1H-pyrrole-2,5-dione (2e): The title compound was synthesized from 1-(3,4-difluorophenyl)-1H-pyrrole-2,5-dione (1e) (1.0 g, 4.8 mmol) according to general procedure B and isolated as a beige solid (0.74 g, 56%). $^1$H-NMR (400 MHz, DMSO-$d_6$): δ 7.63 (q, J=8.9 Hz, 1H), 7.51 (m, 1H), 7.28 (m, 1H). $^{13}$C-NMR (100 MHz, DMSO-$d_6$): δ 161.9, 150.5 (dd, J=11.7 Hz, J=13.1 Hz), 148.0 (dd, J=11.7 Hz, J=12.5 Hz), 132.9, 127.5 (dd, J=3.7 Hz, J=5.1 Hz), 124.6 (dd, J=3.6 Hz, J=3.4 Hz), 118.1 (d, J=18.4 Hz), 116.7 (d, J=19.6 Hz). ESI-HRMS: calc. for $C_{10}H_4NO_2F_2Cl_2$: [M+H]$^+$=277.9582 m/z, found: [M+H]$^+$=m/z 277.9573 m/z.

3,4-Dichloro-1-(3-chloro-4-fluorophenyl)-1H-pyrrole-2,5-dione (2f): The title compound was synthesized from 1-(3-chloro-4-fluorophenyl)-1H-pyrrole-2,5-dione (1f) (1.0 g, 4.4 mmol) according to general procedure B and isolated as a beige solid (0.92 g, 71%). $^1$H-NMR (400 MHz, CDCl$_3$): δ 7.49 (m, 1H), 7.28 (m, 2H). $^{13}$C-NMR (100 MHz, CDCl$_3$): δ 161.5, 157.7 (d, J=252.0 Hz), 133.8, 128.3, 126.9 (d, J=3.9 Hz), 125.8 (d, J=7.7 Hz), 122.0 (d, J=19.3 Hz), 117.2 (d, J=22.6 Hz). C$_{10}$H$_3$Cl$_3$FNO$_2$: [M+H]$^+$=m/z 293.9286, found: [M+H]$^+$=m/z 293.9293.

3,4-Dichloro-1-(4-chloro-3-fluorophenyl)-1H-pyrrole-2,5-dione (2g): The title compound was synthesized from 1-(4-chloro-3-fluorophenyl)-1H-pyrrole-2,5-dione (1g) (0.20 g, 0.89 mmol) according to general procedure B and isolated as a beige solid (0.17 g, 64%). $^1$H-NMR (400 MHz, CDCl$_3$): δ 7.53 (t, J=8.3 Hz, 1H), 7.29 (m, 1H), 7.17 (d, J=8.7 Hz, 1H). $^{13}$C-NMR (100 MHz, CDCl$_3$): δ 161.4, 157.9 (d, J=250.8 Hz), 133.8, 131.1, 130.1 (d, J=9.2 Hz), 121.9 (d, J=4.0 Hz), 121.3 (d, J=17.5 Hz), 114.3 (d, J=24.6 Hz). ESI-HRMS: calc. for C10H3NO2FCl3: [M+H]$^+$=293.9286 m/z, found: [M+H]$^+$=293.9288 m/z.

1-(3-Bromo-4-chlorophenyl)-3,4-dichloro-1H-pyrrole-2,5-dione (2h): The title compound was synthesized from 1-(3-bromo-4-chlorophenyl)-1H-pyrrole-2,5-dione (1h) (0.20 g, 0.70 mmol) according to general procedure B and isolated as a light-yellow solid (0.23 g, 94%). $^1$H-NMR (400 MHz, CDCl$_3$): δ 7.71 (d, J=2.1 Hz, 1H), 7.58 (d, J=8.6 Hz, 1H), 7.33 (dd, J=2.1 Hz, J=6.5 Hz, 1H). $^{13}$C-NMR (100 MHz, CDCl$_3$): δ 161.4, 134.8, 133.8, 130.75, 130.68, 129.7, 125.5, 122.9. ESI-HRMS: calc. for CHNO: [M+H]$^+$=m/z, found: [M+H]$^+$=m/z.

1-(4-Bromo-3-chlorophenyl)-3,4-dichloro-1H-pyrrole-2,5-dione (2i): The title compound was synthesized from 1-(4-bromo-3-chlorophenyl)-1H-pyrrole-2,5-dione (1i) (0.50 g, 1.7 mmol) according to general procedure B and isolated as a light-yellow solid (0.29 g, 47%). $^1$H-NMR (400 MHz, DMSO-d$_6$): δ 7.97 (d, J=8.6 Hz, 1H), 7.68 (d, J=1.7 Hz, 1H), 7.34 (dd, J=1.8 Hz, 6.8 Hz, 1H). $^{13}$C-NMR (100 MHz, DMSO-d$_6$): δ 162.1, 134.9, 133.8, 133.4, 131.8, 128.8, 127.7, 122.0. ESI-HRMS: calc. for CHNO: [M+H]$^+$=m/z, found: [M+H]$^+$=m/z.

3,4-Dichloro-1-(3,4-dichlorophenyl)-1H-pyrrole-2,5-dione (2j): The title compound was synthesized from 1-(3,4-dichlorophenyl)-1H-pyrrole-2,5-dione (1j) (2.0 g, 8.3 mmol) according to general procedure B and isolated as a beige solid (1.2 g, 45%). $^1$H-NMR (400 MHz, CDCl$_3$): δ 7.57 (m, 2H), 7.29 (m, 1H). $^{13}$C-NMR (100 MHz, CDCl$_3$): δ 161.4, 133.9, 133.4, 132.9, 131.0, 129.8, 127.5, 124.8. ESI-HRMS: calc. for C$_{10}$H$_3$Cl$_4$NO$_2$: [M+H]$^+$=m/z 309.8991, found: [M+H]$^+$=m/z 309.8977.

3-Chloro-1-(2,3-dichlorophenyl)-4-morpholino-1H-pyrrole-2,5-dione (3d): The title compound was synthesized from 3,4-dichloro-1-(2,3-dichlorophenyl)-1H-pyrrole-2,5-dione (2d) (0.10 g, 0.32 mmol) and morpholine according to general procedure C and isolated as a yellow solid (81 mg, 70%). $^1$H-NMR (400 MHz, CDCl$_3$): δ 7.57 (dd, J=1.5 Hz, J=6.7 Hz, 1H), 7.32 (t, J=8.0 Hz, 1H), 7.20 (dd, J=1.4 Hz, J=6.5 Hz, 1H), 4.05 (m, 4H), 3.85 (t, J=4.8 Hz, 4H). $^{13}$C-NMR (100 MHz, CDCl$_3$): δ 163.8, 163.4, 140.6, 133.9, 132.1, 131.0, 130.4, 128.7, 127.2, 95.7, 66.6, 48.1. ESI-HRMS: calc. for C$_{14}$H$_{11}$Cl$_3$N$_2$O$_3$: [M+H]$^+$=m/z 360.9908, found: [M+H]$^+$=m/z 360.9924.

3-Chloro-1-(3,4-difluorophenyl)-4-morpholino-1H-pyrrole-2,5-dione (3e): The title compound was synthesized from 3,4-dichloro-1-(3,4-difluorophenyl)-1H-pyrrole-2,5-dione (2e) (0.10 g, 0.36 mmol) and morpholine according to general procedure C and isolated as a yellow solid (68 mg, 57%). $^1$H-NMR (400 MHz, DMSO-d$_6$): δ 7.53 (m, 2H), 7.24 (m, 1H), 3.93 (t, J=4.4 Hz, 4H), 3.74 (t, J=4.8 Hz, 4H). $^{13}$C-NMR (100 MHz, DMSO-d$_6$): δ 165.0, 164.1, 150.6 (dd, J=13.5 Hz, J=7.1 Hz), 148.0 (dd, J=13.5 Hz, J=7.9 Hz), 142.2, 128.5 (dd, J=3.3 Hz, J=5.4 Hz), 124.7 (dd, J=3.5 Hz, J=3.5 Hz), 118.0 (d, J=18.4 Hz), 116.9 (d, J=19.6 Hz), 93.6, 66.8, 48.6. ESI-HRMS: calc. for C$_{14}$H$_{11}$ClF$_2$N$_2$O$_3$: [M+H]$^+$=m/z 329.0499, found: [M+H]$^+$=m/z 329.0504.

3-Chloro-1-(3-chloro-4-fluorophenyl)-4-morpholino-1H-pyrrole-2,5-dione (3f): The title compound was synthesized from 3,4-dichloro-1-(3-chloro-4-fluorophenyl)-1H-pyrrole-2,5-dione (2f) (0.10 g, 0.34 mmol) and morpholine according to general procedure C and isolated as a yellow solid (97 mg, 83%). $^1$H-NMR (400 MHz, DMSO-d$_6$): δ 7.62 (dd, J=2.5 Hz, J=4.3 Hz, 1H), 7.55 (t, J=9.0 Hz, 1H), 7.38 (m, 1H), 3.93 (t, J=4.4 Hz, 4H), 3.74 (t, J=4.9 Hz, 4H). $^{13}$C-NMR (100 MHz, DMSO-d$_6$): δ 164.7, 163.8, 156.4 (d, J=247.8 Hz), 141.9, 129.1, 128.6 (d, J=3.5 Hz), 128.0 (d, J=7.8 Hz), 119.5 (d, J=18.9 Hz), 117.2 (d, J=22.2 Hz), 93.3, 66.4, 48.3. ESI-HRMS: calc. for C$_{14}$H$_{11}$ClFN$_2$O$_3$: [M+H]$^+$=m/z 345.0204, found: [M+H]$^+$=m/z 345.0187.

3-Chloro-1-(4-chloro-3-fluorophenyl)-4-morpholino-1H-pyrrole-2,5-dione (3g): The title compound was synthesized from 3,4-dichloro-1-(4-chloro-3-fluorophenyl)-1H-pyrrole-2,5-dione (2g) (70 mg, 0.24 mmol) and morpholine according to general procedure C and isolated as a yellow solid (53 mg, 65%). $^1$H-NMR (400 MHz, DMSO-d$_6$): δ 7.72 (t, J=8.5 Hz, 1H), 7.46 (dd, J=2.2 Hz, J=8.2 Hz, 1H), 7.27 (dt, J=1.0 Hz, J=6.5 Hz, 1H), 3.93 (t, J=4.4 Hz, 4H), 3.75 (t, J=4.8 Hz, 4H). $^{13}$C-NMR (100 MHz, DMSO-d$_6$): δ 164.8, 163.9, 157.1 (d, J=246.6 Hz), 142.3, 132.1 (d, J=9.8 Hz), 131.0, 124.4 (d, J=3.7 Hz), 119.0 (d, J=17.3 Hz), 115.6 (d, J=23.8 Hz), 93.7, 66.8, 48.7. ESI-HRMS: calc. for C$_{14}$H$_{11}$Cl$_2$FN$_2$O$_3$: [M+H]$^+$=m/z 345.0204, found: [M+H]=m/z 345.0200.

1-(3-Bromo-4-chlorophenyl)-3-chloro-4-morpholino-1H-pyrrole-2,5-dione (3h): The title compound was synthesized from 1-(3-bromo-4-chlorophenyl)-3,4-dichloro-1H-pyrrole-2,5-dione (2h) (0.10 g, 0.28 mmol) and morpholine according to general procedure C and isolated as a yellow solid (50 mg, 44%). $^1$H-NMR (400 MHz, DMSO-d$_6$): δ 7.77 (m, 2H), 7.41 (dd, J=2.2 Hz, 6.4 Hz, 1H), 3.93 (t, J=4.3 Hz, 4H), 3.74 (t, J=4.7 Hz, 4H). $^{13}$C-NMR (100 MHz, DMSO-d$_6$): δ 164.5, 163.6, 141.9, 132.3, 131.6, 131.4, 130.6, 127.6, 121.2, 93.4, 66.4, 48.3. ESI-HRMS: calc. for C$_{14}$H$_{11}$BrCl$_2$N$_2$O$_3$: [M+H]$^+$=m/z 404.9403, found: [M+H]$^+$=m/z 404.9405.

1-(4-Bromo-3-chlorophenyl)-3-chloro-4-morpholino-1H-pyrrole-2,5-dione (3i): The title compound was synthesized from 1-(4-bromo-3-chlorophenyl)-3,4-dichloro-1H-pyrrole-2,5-dione (2i) (0.10 g, 0.28 mmol) and morpholine according to general procedure C and isolated as a yellow solid (73 mg, 64%). $^1$H-NMR (400 MHz, DMSO-d$_6$): δ 7.89 (d, J=8.6 Hz, 1H), 7.66 (d, J=2.2 Hz, 1H), 7.30 (dd, J=2.2 Hz, 6.4 Hz, 1H), 3.93 (t, J=4.3 Hz, 4H), 3.74 (t, J=4.5 Hz, 4H). $^{13}$C-NMR (100 MHz, DMSO-d$_6$): δ 164.8, 163.9, 142.3, 134.4, 133.5, 132.4, 128.7, 127.4, 120.8, 93.8, 66.8, 48.7. ESI-HRMS: calc. for C$_{14}$H$_{11}$BrCl$_2$N$_2$O$_3$: [M+H]$^+$=m/z 404.9403, found: [M+H]$^-$=m/z 404.9418.

3-Chloro-1-(3,4-dichlorophenyl)-4-(4-methylpiperazin-1-yl)-1H-pyrrole-2,5-dione (3j): The title compound was synthesized from 3,4-dichloro-1-(3,4-dichlorophenyl)-1H-pyrrole-2,5-dione (2j) (0.10 g, 0.32 mmol) and N-methylpiperazine according to general procedure C and isolated as a yellow solid (71 mg, 59%). $^1$H-NMR (400 MHz, CDCl$_3$): δ 7.53 (m, 2H), 7.26 (dd, J=2.4 Hz, J=6.3 Hz, 1H), 4.05 (t, J=4.6 Hz, 4H), 2.57 (t, J=4.8 Hz, 4H), 2.35 (s, 3H). $^{13}$C-NMR (100 MHz, CDCl$_3$): δ 164.2, 163.6, 140.5, 132.5, 131.3, 130.3, 130.2, 127.3, 124.7, 95.0, 54.8, 47.8, 45.6.

ESI-HRMS: calc. for $C_{15}H_{14}Cl_3N_3O_2$: $[M+H]^+$=m/z 374.0224, found: $[M+H]^-$=m/z 374.0207.

N-(3,4-Dichloro-phenyl)-2-(4-methoxy-phenyl)-acetamide (4a): The title compound was synthesized from 2-(4-methoxyphenyl)acetic acid (1.5 g, 9.0 mmol) and 3,4-dichloroaniline according to general procedure D and isolated as a white solid (2.4 g, 87%). $^1$H-NMR (400 MHz, DMSO-$d_6$): δ 10.40 (s, 1H), 7.99 (d, J=2.0 Hz, 1H), 7.51 (m, 2H), 7.24 (d, J=8.5 Hz, 2H), 6.88 (d, J=8.5 Hz, 2H), 3.73 (s, 3H), 3.58 (s, 2H). $^{13}$C-NMR (100 MHz, DMSO-$d_6$): δ 170.4, 158.6, 139.8, 131.4, 131.1, 130.6, 127.8, 125.0, 120.7, 119.5, 114.2, 55.5, 42.8. ESI-HRMS: calc. for $C_{15}H_{13}Cl_2NO_2$: $[M+H]^+$=m/z 310.0396, found: $[M+H]^+$=mz 310.0406.

N-(3,4-Dichlorophenyl)-2-(2,4-dimethoxyphenyl)acetamide (4b): The title compound was synthesized from 2-(2,4-dimethoxyphenyl)acetic acid (1.0 g, 5.1 mmol) and 3,4-dichloroaniline according to general procedure D and isolated as a light-yellow solid (1.4 g, 81%). $^1$H-NMR (400 MHz, CDCl$_3$): δ 7.76 (br, 1H), 7.66 (s, 1H), 7.27 (m, 3H), 6.54 (m, 2H), 3.91 (s, 3H), 3.84 (s, 3H), 3.64 (s, 2H). $^{13}$C-NMR (100 MHz, CDCl$_3$): δ 170.0, 160.7, 157.9, 137.6, 132.6, 131.8, 130.3, 127.0, 121.2, 118.8, 115.0, 105.0, 99.1, 55.7, 55.5, 39.3. ESI-HRMS: calc. for $C_{16}H_{15}Cl_2NO_3$: $[M+H]^+$=m/z 340.0502, found: $[M+H]^+$=m/z 340.0514.

N-(3,4-Dichlorophenyl)-2-(4-(dimethylamino)phenyl)acetamide (4c): The title compound was synthesized from 2-(4-(dimethylamino)phenyl)acetic acid (0.50 g, 2.8 mmol) and 3,4-dichloroaniline according to general procedure E and isolated as a white solid (0.73 g, 81%). $^1$H-NMR (400 MHz, CDCl$_3$): δ 7.65 (d, J=2.1 Hz, 1H), 7.44 (br, 1H), 7.29 (m, 2H), 7.16 (d, J=8.6 Hz, 2H), 6.75 (d, J=8.6 Hz, 2H), 3.64 (s, 2H), 2.99 (s, 6H). $^{13}$C-NMR (100 MHz, CDCl$_3$): δ 170.5, 150.1, 137.3, 132.6, 130.3, 130.2, 127.3, 121.4, 120.9, 119.0, 113.1, 43.7, 40.5. ESI-HRMS: calc. for $C_{16}H_{16}Cl_2N_2O$: $[M+H]^+$=m/z 323.0713, found: $[M+H]^+$=m/z 323.0727.

N-(3,4-Dichlorophenyl)-2-(3,4-dimethoxyphenyl)acetamide (4d): The title compound was synthesized from 2-(3,4-dimethoxyphenyl)acetic acid (1.0 g, 5.1 mmol) and 3,4-dichloroaniline according to general procedure D and isolated as an off-white solid (0.73 g, 42%). $^1$H-NMR (400 MHz, CDCl$_3$): δ 7.67 (d, J=2.3 Hz, 1H), 7.27 (m, 3H), 6.87 (m, 3H), 3.92 (s, 3H), 3.90 (s, 3H), 3.69 (s, 2H). $^{13}$C-NMR (100 MHz, CDCl$_3$): δ 169.5, 149.6, 148.7, 137.1, 132.7, 130.4, 127.6, 126.2, 121.7, 121.3, 118.9, 112.4, 111.7, 56.0, 55.9, 44.3. ESI-HRMS: calc. for $C_{16}H_{15}Cl_2NO_3$: $[M+H]^+$=m/z 340.0502, found: $[M+H]^+$=m/z 340.0518.

tert-Butyl 4-(2-(3,4-dichlorophenylamino)-2-oxoethyl)phenylcarbamate (4e): 2-(4-Aminophenyl)acetic acid (2.0 g, 13.2 mmol) and sodium carbonate (1.4 g, 13.2 mmol) were placed in a round-bottomed flask and dissolved in a mixture of water (25 mL) and 1,4-dioxane (25 mL). The reaction was cooled to 0° C. and then di-tert-butyl dicarbonate (3.2 g, 14.6 mmol) was added to the reaction in one portion. The reaction was allowed to warm to RT and then stirred for 4 h. After the reaction was complete as evidenced by TLC, the 1,4-dioxane was removed in vacuo and the pH of the remaining aqueous solution was adjusted to approximately 4 with 1N HCl. The organic products were extracted with EtOAc (3×30 mL), washed with brine (20 mL), dried with anhydrous Na$_2$SO$_4$ and concentrated in vacuo. The product, 2-(4-(tert-butoxycarbonylamino)phenyl)acetic acid was purified by recrystallization from MeOH and isolated as a white solid (2.8 g, 84%). The title compound was then synthesized from 2-(4-(tert-butoxycarbonylamino)phenyl) acetic acid (1.0 g, 4.0 mmol) and 3,4-dichloroaniline according to general procedure E and isolated as a white solid (1.4 g, 92%). $^1$H-NMR (400 MHz, DMSO-$d_6$): δ 10.47 (s, 1H), 9.19 (s, 1H), 7.60 (s, 1H), 7.48 (m, 2H), 7.33 (d, J=7.7 Hz, 2H), 7.18 (d, J=8.0 Hz, 2H), 3.53 (s, 2H), 1.41 (s, 9H). $^{13}$C-NMR (100 MHz, DMSO-$d_6$): δ 170.7, 153.4, 139.3, 138.4, 131.5, 131.0, 129.8, 129.5, 125.4, 120.9, 119.7, 118.8, 79.7, 42.9, 28.4. ESI-HRMS: calc. for $C_{19}H_{20}Cl_2N_2O_3$: $[M-H]^-$=m/z 393.0778, found: $[M-H]^-$=m/z 393.0797.

N-(3,4-Dichloro-phenyl)-2-phenyl-acetamide (4f): The title compound was synthesized from 2-phenylaceitic acid (1.5 g, 11 mmol) and 3,4-dichloroaniline according to general procedure D and isolated as a white solid (2.1 g, 68%). $^1$H-NMR (400 MHz, DMSO-$d_6$): δ 10.47 (s, 1H), 8.00 (d, J=2.2 Hz, 1H), 7.51 (m, 2H), 7.33 (d, J=4.4 Hz, 4H), 7.26 (m, 1H), 3.66 (s, 2H). $^{13}$C-NMR (100 MHz, DMSO-$d_6$): δ 170.1, 139.7, 135.9, 131.4, 131.1, 129.6, 128.8, 127.1, 125.1, 120.7, 119.6, 43.7. ESI-HRMS: calc. for $C_{14}H_{11}Cl_2NO$: $[M+H]^+$=m/z 280.0291, found: $[M+H]^+$=m/z 280.0304.

N-(3,4-Dichloro-phenyl)-2-(4-trifluoromethyl-phenyl)-acetamide (4g): The title compound was synthesized from 2-(4-(trifluoromethyl)phenyl)acetic acid (1.5 g, 7.4 mmol) and 3,4-dichloroaniline according to general procedure D and isolated as an off-white solid (2.1 g, 82%). $^1$H-NMR (400 MHz, DMSO-$d_6$): δ 10.53 (s, 1H), 7.99 (d, J=2.1 Hz, 1H), 7.68 (d, J=8.0 Hz, 2H), 7.49 (m, 4H), 3.79 (s, 2H). $^{13}$C-NMR (100 MHz, DMSO-$d_6$): δ 169.0, 140.3, 139.2, 131.1, 130.8, 130.2, 125.8, 125.2 (q, J=3.6 Hz), 124.8, 123.1, 120.4, 119.2, 42.8. ESI-HRMS: calc. for $C_{15}H_{10}Cl_2F_3NO$: $[M+H]^+$=m/z 348.0164, found: $[M+H]^+$=m/z 348.0162.

1-(3,4-Dichloro-phenyl)-3-hydroxy-4-(4-methoxy-phenyl)-pyrrole-2,5-dione (5a): The title compound was synthesized from N-(3,4-dichloro-phenyl)-2-(4-methoxy-phenyl)-acetamide (4a) (2.1 g, 6.8 mmol) according to general procedure F and isolated as a yellow solid (2.5 g, 79%). $^1$H-NMR (400 MHz, DMSO-$d_6$): δ 7.96 (d, J=8.9 Hz, 2H), 7.75 (m, 2H), 7.47 (dd, J=2.3 Hz, J=6.3 Hz, 1H), 7.01 (d, J=8.9 Hz, 2H), 3.78 (s, 3H). $^{13}$C-NMR (100 MHz, DMSO-$d_6$): δ 169.7, 165.3, 158.7, 152.1, 131.8, 131.0, 130.7, 129.8, 129.2, 128.4, 126.9, 122.0, 114.0, 106.3, 55.2. ESI-HRMS: calc. for $C_{17}H_{11}Cl_2NO_4$: $[M+H]^+$=m/z 361.9992, found: $[M+H]^+$=m/z 361.9994.

1-(3,4-Dichlorophenyl)-3-(2,4-dimethoxyphenyl)-4-hydroxy-1H-pyrrole-2,5-dione (5b): The title compound was synthesized from N-(3,4-dichlorophenyl)-2-(2,4-dimethoxyphenyl)acetamide (4b) (0.79 g, 2.3 mmol) according to general procedure F and isolated as a yellow solid (0.44 g, 48%). $^1$H-NMR (400 MHz, CDCl$_3$): δ 8.56 (s, 1H), 7.88 (d, J=8.8 Hz, 1H), 7.64 (d, J=2.4 Hz, 1H), 7.54 (d, J=8.7 Hz, 1H), 7.37 (dd, J=2.4 Hz, 6.3 Hz, 1H), 6.72 (dd, J=2.4 Hz, 6.4 Hz, 1H), 6.44 (d, J=2.4 Hz, 1H), 4.05 (s, 3H), 3.89 (s, 3H). $^{13}$C-NMR (100 MHz, DMSO-$d_6$): δ 169.4, 165.4, 161.2, 158.6, 152.9, 131.9, 131.6, 131.2, 130.7, 129.9, 127.9, 126.5, 108.9, 106.4, 105.0, 98.4, 55.5, 55.4. ESI-HRMS: calc. for $C_{18}H_{13}Cl_2NO_5$: $[M+H]^+$=m/z 394.0244, found: $[M+H]^+$=m/z 394.0261.

1-(3,4-Dichlorophenyl)-3-(3,4-dimethoxyphenyl)-4-hydroxy-1H-pyrrole-2,5-dione (5d): The title compound was synthesized from N-(3,4-dichlorophenyl)-2-(3,4-dimethoxyphenyl)acetamide (4d) (0.72 g, 2.1 mmol) according to general procedure F and isolated as a yellow-orange solid (0.74 g, 89%). $^1$H-NMR (400 MHz, DMSO-$d_6$): δ 7.76 (m, 2H), 7.67 (s, 1H), 7.63 (d, J=8.1 Hz, 1H), 7.47 (d, J=8.4 Hz, 1H), 7.05 (d, J=8.6 Hz, 1H), 3.79 (s, 3H), 3.77 (s, 3H). $^{13}$C-NMR (100 MHz, DMSO-$d_6$): δ 170.1, 165.6, 152.6, 148.9, 148.7, 132.1, 131.4, 131.1, 130.2, 128.7, 127.3, 122.6, 121.4, 112.1, 111.5, 106.6, 55.9, 55.8. ESI-HRMS: calc. for $C_{18}H_{13}Cl_2NO_5$: [M−H]⁻=m/z 392.0098, found: [M−H]⁻=m/z 392.0096.

tert-Butyl 4-(1-(3,4-dichlorophenyl)-4-hydroxy-2,5-dioxo-2,5-dihydro-1H-pyrrol-3-yl)phenylcarbamate:
¹H-NMR (400 MHz, DMSO-d₆): δ 9.36 (s, 1H), 7.88 (d, J=8.8 Hz, 2H), 7.66 (m, 2H), 7.41 (m, 3H), 1.44 (s, 9H). ¹³C-NMR (100 MHz, DMSO-d₆): δ 170.3, 165.6, 154.4, 153.3, 138.8, 132.0, 131.4, 131.0, 130.2, 128.5, 128.3, 127.0, 124.2, 118.3, 105.4, 80.0, 28.4. ESI-HRMS: calc. for $C_{21}H_{18}Cl_2N_2O_5$: [M−H]⁻=m/z 447.0520, found: [M−H]⁻=m/z 447.0541.

1-(3,4-Dichloro-phenyl)-3-hydroxy-4-phenyl-pyrrole-2,5-dione (5f): The title compound was synthesized from N-(3,4-dichloro-phenyl)-2-phenyl-acetamide (4f) (1.0 g, 3.6 mmol) according to general procedure F and isolated as a yellow solid (0.95 g, 80%). ¹H-NMR (400 MHz, DMSO-d₆): δ 8.00 (d, J=7.3 Hz, 2H), 7.77 (m, 2H), 7.45 (m, 3H), 7.30 (t, J=7.4 Hz, 1H). ¹³C-NMR (100 MHz, DMSO-d₆): δ 170.0, 165.4, 155.1, 132.2, 131.4, 131.1, 130.2, 128.8, 128.7, 127.9, 127.8, 127.3, 105.7. ESI-HRMS: calc. for $C_{16}H_9Cl_2NO_3$: [M+H]⁺=m/z 331.9887, found: [M+H]⁺=m/z 331.9894.

1-(3,4-Dichloro-phenyl)-3-hydroxy-4-(4-trifluoromethyl-phenyl)-pyrrole-2,5-dione (5g): The title compound was synthesized from N-(3,4-dichloro-phenyl)-2-(4-trifluoromethyl-phenyl)-acetamide (4g) (1.5 g, 4.3 mmol) according to general procedure F and isolated as a yellow solid (1.7 g, 95%). ¹H-NMR (400 MHz, DMSO-d₆): δ 10.97 (br, 1H), 8.22 (d, J=8.3 Hz, 2H), 7.72 (m, 4H), 7.44 (dd, J=2.3 Hz, J=6.3 Hz, 1H). ¹³C-NMR (100 MHz, DMSO-d₆): δ 169.7, 164.8, 159.7, 135.3, 132.0, 131.0, 130.7, 129.7, 128.3, 126.8, 126.7, 125.1, 125.0, 123.1, 101.3. ESI-HRMS: calc. for $C_{17}H_8Cl_2F_3NO_3$: [M−H]⁻=m/z 399.9761, found: [M−H]⁻=m/z 399.9772.

3-Chloro-1-(3,4-dichloro-phenyl)-4-(4-methoxy-phenyl)-pyrrole-2,5-dione (6a): The title compound was synthesized from 1-(3,4-dichlorophenyl)-3-hydroxy-4-(4-methoxy-phenyl)-pyrrole-2,5-dione (5a) (1.0 g, 2.7 mmol) according to general procedure G and isolated as a yellow solid (0.99 g, 95%). ¹H-NMR (400 MHz, CDCl₃): δ 8.06 (d, J=9.0 Hz, 2H), 7.57 (m, 2H), 7.34 (dd, J=2.4 Hz, J=6.3 Hz, 1H), 7.05 (d, J=9.0 Hz, 2H), 3.90 (s, 3H). ¹³C-NMR (100 MHz, CDCl₃): δ 166.7, 163.6, 161.6, 134.3, 132.7, 131.8, 131.4, 130.4, 130.2, 128.1, 127.3, 124.6, 118.9, 114.0, 55.1. ESI-HRMS: calc. for $C_{17}H_{10}Cl_3NO_3$: [M+H]⁺=m/z 381.9799, found: [M+H]⁺=m/z 381.9801.

3-Chloro-1-(3,4-dichloro-phenyl)-4-(2,4-dimethoxyphenyl)-1H-pyrrole-2,5-dione (6b): The title compound was synthesized from 1-(3,4-dichlorophenyl)-3-(2,4-dimethoxyphenyl)-4-hydroxy-1H-pyrrole-2,5-dione (5b) (0.40 g, 1.0 mmol) according to general procedure G and isolated as a yellow solid (0.35 g, 85%). ¹H-NMR (400 MHz, CDCl₃): δ 7.58 (m, 2H), 7.37 (m, 2H), 6.34 (m, 2H), 3.90 (s, 6H). ¹³C-NMR (100 MHz, CDCl₃): δ 166.5, 163.9, 163.6, 159.2, 135.9, 133.0, 132.2, 131.9, 130.8, 130.7, 127.5, 124.9, 108.1, 105.3, 99.0, 55.6. ESI-HRMS: calc. for $C_{18}H_{12}Cl_3NO_4$: [M+H]⁺=m/z 411.9905, found: [M+H]⁺=m/z 411.9920.

3-Chloro-1-(3,4-dichlorophenyl)-4-(4-(dimethylamino)phenyl)-1H-pyrrole-2,5-dione (6c): 1-(3,4-Dichlorophenyl)-3-(4-(dimethylamino)phenyl)-4-hydroxy-1H-pyrrole-2,5-dione (5c) was synthesized from N-(3,4-dichlorophenyl)-2-(4-(dimethylamino)phenyl)acetamide (4c) (0.70 g, 2.2 mmol) according to general procedure F and isolated as a light-orange solid (0.27 g, 33%). ESI-HRMS: calc. for $C_{18}H_{14}Cl_2N_2O_3$: [M+H]⁺=m/z 377.0454, found: [M+H]⁺=m/z 377.0465. The obtained intermediate (5c) (0.50 g, 1.3 mmol) was then immediately subjected to general procedure G to yield the title compound as a dark-red solid (0.35 g, 66%). ¹H-NMR (400 MHz, CDCl₃): δ 8.15 (d, J=9.1 Hz, 2H), 7.63 (d, J=2.2 Hz, 1H), 7.56 (d, J=8.6 Hz, 1H), 7.35 (dd, J=2.3 Hz, 6.4 Hz, 1H), 6.78 (d, J=9.1 Hz, 2H), 3.11 (s, 6H). ¹³C-NMR (100 MHz, CDCl₃): δ 167.2, 164.1, 151.6, 134.2, 132.6, 131.4, 131.2, 130.5, 130.2, 127.3, 124.7, 123.3, 114.1, 111.1, 39.6. ESI-HRMS: calc. for $C_{18}H_{13}Cl_3N_2O_2$: [M+H]⁺=m/z 395.0115, found: [M+H]⁺=m/z 395.0131.

3-Chloro-1-(3,4-dichlorophenyl)-4-(3,4-dimethoxyphenyl)-1H-pyrrole-2,5-dione (6d): The title compound was synthesized from 1-(3,4-dichlorophenyl)-3-(3,4-dimethoxyphenyl)-4-hydroxy-1H-pyrrole-2,5-dione (5d) (0.50 g, 1.3 mmol) according to general procedure G and isolated as a yellow solid (0.43 g, 82%). ¹H-NMR (400 MHz, CDCl₃): δ 7.78 (dd, J=2.0 Hz, 6.5 Hz, 1H), 7.67 (d, J=1.9 Hz, 1H), 7.62 (d, J=2.35 Hz, 1H), 7.57 (d, J=8.6 Hz, 1H), 7.34 (dd, J=2.4 Hz, 6.3 Hz, 1H), 7.02 (d, J=8.6 Hz, 1H), 3.98 (s, 3H), 3.96 (s, 3H). ¹³C-NMR (100 MHz, CDCl₃): δ 167.1, 163.8, 151.8, 148.9, 134.4, 133.1, 132.2, 130.7, 130.5, 128.5, 127.7, 125.0, 124.2, 119.5, 112.3, 111.0, 56.0, 55.9.

3-(4-Aminophenyl)-4-chloro-1-(3,4-dichlorophenyl)-1H-pyrrole-2,5-dione (6e): tert-Butyl 4-(4-chloro-1-(3,4-dichlorophenyl)-2,5-dioxo-2,5-dihydro-1H-pyrrol-3-yl)phenylcarbamate was synthesized from tert-butyl 4-(1-(3,4-dichlorophenyl)-4-hydroxy-2,5-dioxo-2,5-dihydro-1H-pyrrol-3-yl)phenylcarbamate (5e) (0.40 g, 0.89 mmol) according to general procedure G and isolated as a yellow solid (0.39 g, 93%). ¹H-NMR (400 MHz, CDCl₃): δ 7.98 (d, J=8.8 Hz, 2H), 7.51 (m, 3H), 7.29 (dd, J=2.4 Hz, 6.3 Hz, 1H), 7.05 (s, 1H), 1.54 (s, 9H). ¹³C-NMR (100 MHz, CDCl₃): δ 166.9, 163.9, 152.3, 141.5, 134.4, 133.0, 132.0, 131.0, 130.7, 130.5, 129.0, 127.5, 125.0, 120.9, 118.0, 81.3, 28.3. ESI-HRMS: calc. for $C_{21}H_{17}Cl_3N_2O_4$: [M+H]⁺=m/z 467.0327, found: [M+H]⁺=m/z 467.0338.

tert-Butyl 4-(4-chloro-1-(3,4-dichlorophenyl)-2,5-dioxo-2,5-dihydro-1H-pyrrol-3-yl)phenylcarbamate (0.10 g, 0.21 mmol) was placed in a round-bottomed flask and dissolved in DCM (9 mL) at RT. Trifluoroacetic acid (1 mL) was added and the reaction was stirred at RT for 2 h. After the reaction was complete as evidenced by TLC, it was concentrated in vacuo and purified by preparatory HPLC. The title compound was isolated as a red solid (34 mg, 43%). ¹H-NMR (400 MHz, CDCl₃): δ 8.01 (d, J=8.6 Hz, 2H), 7.59 (m, 2H), 7.34 (dd, J=2.2 Hz, 6.4 Hz, 1H), 6.77 (d, J=8.6 Hz, 2H), 4.18 (s, 2H). ¹³C-NMR (100 MHz, CDCl₃): δ 167.3, 164.3, 149.6, 134.7, 133.0, 132.0, 131.9, 130.7, 127.7, 125.8, 125.0, 116.7, 114.5. ESI-HRMS: calc. for $C_{16}H_9Cl_3N_2O_2$: [M−H]⁻=m/z 364.9657, found: [M−H]⁻=m/z 364.9655.

3-Chloro-1-(3,4-dichloro-phenyl)-4-phenyl-pyrrole-2,5-dione (6f): The title compound was synthesized from 1-(3,4-dichloro-phenyl)-3-hydroxy-4-phenyl-pyrrole-2,5-dione (5f) (0.80 g, 2.4 mmol) according to general procedure G and isolated as a yellow solid (0.73 g, 87%). ¹H-NMR (400 MHz, DMSO-d₆): δ 7.87 (m, 3H), 7.78 (d, J=2.3 Hz, 1H), 7.61 (m, 3H), 7.50 (dd, J=2.3 Hz, J=6.3 Hz, 1H). ¹³C-NMR (100 MHz,): δ 167.0, 164.0, 135.7, 131.7, 131.6, 131.5, 131.4, 131.3, 131.2, 130.0, 129.2, 129.1, 127.6, 127.2. ESI-HRMS: calc. for $C_{16}H_8Cl_3NO_2$: [M+H]⁺=m/z 351.9693, found: [M+H]⁺=m/z 351.9700.

3-Chloro-1-(3,4-dichloro-phenyl)-4-(4-trifluoromethyl-phenyl)-pyrrole-2,5-dione (6g): The title compound was synthesized from 1-(3,4-dichlorophenyl)-3-hydroxy-4-(4-trifluoromethyl-phenyl)-pyrrole-2,5-dione (5g) (1.5 g, 4.3 mmol) according to general procedure G and isolated as a yellow solid (0.94 g, 90%). $^1$H-NMR (400 MHz, CDCl$_3$): δ 8.10 (d, J=8.2 Hz, 2H), 7.81 (d, J=8.3 Hz, 2H), 7.60 (m, 2H), 7.35 (dd, J=2.4 Hz, J=6.2 Hz, 1H). $^{13}$C-NMR (100 MHz, CDCl$_3$): δ 166.2, 163.1, 134.0, 133.7, 133.3, 132.9, 132.6, 130.9, 130.1, 130.0, 129.8 (d, J=1.3 Hz), 127.6, 125.7 (q, J=3.7 Hz), 124.9, 124.8.

1-(3,4-Dichloro-phenyl)-3-(4-methoxy-phenyl)-4-morpholin-4-yl-pyrrole-2,5-dione (7a): The title compound was synthesized from 3-chloro-1-(3,4-dichloro-phenyl)-4-(4-methoxy-phenyl)-pyrrole-2,5-dione (6a) (0.40 g, 1.0 mmol) and morpholine according to general procedure H and isolated as a yellow solid (0.31 g, 69%). $^1$H-NMR (400 MHz, DMSO-d$_6$): δ 7.74 (m, 2H), 7.41 (dd, J=2.2 Hz, J=6.4 Hz, 1H), 7.31 (d, J=8.6 Hz, 2H), 6.99 (d, J=8.7 Hz, 2H), 3.78 (s, 3H), 3.63 (t, J=4.0 Hz, 4H), 3.48 (t, J=4.5 Hz, 4H). $^{13}$C-NMR (100 MHz, DMSO-d$_6$): δ 168.8, 165.9, 158.8, 143.0, 132.1, 131.5, 131.0, 130.7, 129.7, 128.3, 126.8, 122.5, 113.5, 104.6, 66.0, 55.2, 48.9. ESI-HRMS: calc. for C$_{21}$H$_{18}$Cl$_2$N$_2$O$_4$: [M+H]$^+$=m/z 433.0716, found: [M+H]$^+$=m/z 433.0718.

1-(3,4-Dichlorophenyl)-3-(2,4-dimethoxyphenyl)-4-morpholino-1H-pyrrole-2,5-dione (7b): The title compound was synthesized from 3-chloro-1-(3,4-dichlorophenyl)-4-(2,4-dimethoxyphenyl)-1H-pyrrole-2,5-dione (6b) (0.10 g, 0.24 mmol) and morpholine according to general procedure H and isolated as a yellow solid (60 mg, 53%). $^1$H-NMR (400 MHz, CD$_3$CN): δ 7.62 (m, 2H), 7.39 (dd, J=2.4 Hz, 6.2 Hz, 1H), 7.19 (m, 1H), 6.61 (m, 2H), 3.84 (m, 6H), 3.63 (m, 6H), 2.33 (m, 2H). $^{13}$C-NMR (100 MHz, DMSO-d$_6$): δ 168.6, 165.8, 160.8, 158.4, 143.7, 132.6, 132.1, 131.0, 130.6, 129.6, 128.2, 126.7, 111.4, 104.8, 101.1, 98.2, 66.1, 55.5, 55.3, 47.9. ESI-HRMS: calc. for C$_{22}$H$_{20}$Cl$_2$N$_2$O$_5$: [M+H]$^+$=m/z 463.0822, found: [M+H]$^+$=m/z 463.0866.

1-(3,4-Dichlorophenyl)-3-(4-(dimethylamino)phenyl)-4-morpholino-1H-pyrrole-2,5-dione (7c): The title compound was synthesized from 3-chloro-1-(3,4-dichlorophenyl)-4-(4-(dimethylamino)phenyl)-1H-pyrrole-2,5-dione (6c) (0.10 g, 0.25 mmol) and morpholine according to general procedure H and isolated as a red solid (80 mg, 71%). $^1$H-NMR (400 MHz, DMSO-d$_6$): δ 7.72 (m, 2H), 7.41 (dd, J=2.3 Hz, 6.4 Hz, 1H), 7.23 (d, J=8.7 Hz, 2H), 6.75 (d, J=8.8 Hz, 2H), 3.64 (t, J=3.9 Hz, 4H), 3.47 (br, 4H), 2.94 (s, 6H). $^{13}$C-NMR (100 MHz, DMSO-d$_6$): δ 169.5, 166.5, 150.0, 142.3, 132.5, 131.3, 131.2, 131.0, 129.9, 128.7, 127.2, 117.6, 111.8, 106.6, 66.4, 49.1, 40.3. ESI-HRMS: calc. for C$_{22}$H$_{21}$Cl$_2$N$_3$O$_3$: [M+H]$^+$=mz 446.1033, found: [M+H]$^+$=m/z 446.1053.

1-(3,4-Dichlorophenyl)-3-(3,4-dimethoxyphenyl)-4-morpholino-1H-pyrrole-2,5-dione (7d): The title compound was synthesized from 3-chloro-1-(3,4-dichlorophenyl)-4-(3,4-dimethoxyphenyl)-1H-pyrrole-2,5-dione (6d) (0.50 g, 1.3 mmol) and morpholine according to general procedure H and isolated as a yellow solid (0.43 g, 82%). $^1$H-NMR (400 MHz, DMSO-d$_6$/MeOD): δ 7.73 (m, 2H), 7.42 (d, J=8.7 Hz, 1H), 6.94 (m, 3H), 3.79 (s, 3H), 3.78 (s, 3H), 3.64 (br, 4H), 3.52 (br, 4H). $^{13}$C-NMR (100 MHz, DMSO-d$_6$/MeOD): δ 169.1, 166.2, 148.9, 148.5, 143.4, 132.4, 131.4, 131.0, 130.1, 128.6, 127.1, 123.4, 123.2, 114.1, 111.6, 105.0, 66.4, 55.9, 55.8, 49.2. ESI-HRMS: calc. for C$_{22}$H$_{20}$Cl$_2$N$_2$O$_5$: [M+H]$^+$=m/z 463.0822, found: [M+H]$^+$=m/z 463.0832.

3-(4-Aminophenyl)-1-(3,4-dichlorophenyl)-4-morpholino-1H-pyrrole-2,5-dione (7e): tert-Butyl 4-(1-(3,4-dichlorophenyl)-4-morpholino-2,5-dioxo-2,5-dihydro-1H-pyrrol-3-yl)phenylcarbamate was synthesized from tert-butyl 4-(4-chloro-1-(3,4-dichlorophenyl)-2,5-dioxo-2,5-dihydro-1H-pyrrol-3-yl)phenylcarbamate (0.13 g, 0.27 mmol) (precursor to 6e) and morpholine according to general procedure H. However, before HPLC purification, the crude extract was placed in a round-bottomed flask and dissolved in DCM (9 mL) at RT. Trifluoroacetic acid (1 mL) was added and the reaction was stirred for 2 h at RT. After the reaction was complete as evidenced by TLC, it was concentrated in vacuo and purified by preparatory HPLC. The title compound was isolated as an orange solid (79 mg, 71%). $^1$H-NMR (400 MHz, DMSO-d$_6$): δ 7.74 (d, J=8.7 Hz, 1H), 7.69 (d, J=2.3 Hz, 1H), 7.41 (dd, J=2.3 Hz, 6.3 Hz, 1H), 7.07 (d, J=8.4 Hz, 2H), 6.59 (d, J=8.4 Hz, 2H), 5.33 (s, 2H), 3.63 (t, J=4.1 Hz, 4H), 3.46 (t, J=4.5 Hz, 4H). $^{13}$C-NMR (100 MHz, DMSO-d$_6$): δ 169.5, 166.5, 148.9, 142.1, 132.5, 131.34, 131.31, 131.0, 129.9, 128.6, 127.1, 117.2, 113.6, 107.2, 66.4, 49.0. ESI-HRMS: calc. for C$_{20}$H$_{17}$Cl$_2$N$_3$O$_3$: [M+H]$^+$=m/z 418.0720, found: [M+H]$^+$=m/z 418.0725.

1-(3,4-Dichloro-phenyl)-3-morpholin-4-yl-4-phenyl-pyrrole-2,5-dione (7f): The title compound was synthesized from 3-chloro-1-(3,4-dichloro-phenyl)-4-phenyl-pyrrole-2,5-dione (6f) (0.30 g, 0.85 mmol) and morpholine according to general procedure H and isolated as a yellow-orange solid (0.24 g, 71%). $^1$H-NMR (400 MHz, DMSO-d$_6$): δ 7.75 (m, 2H), 7.39 (m, 6H), 3.63 (d, J=4.2 Hz, 4H), 3.50 (d, J=4.1 Hz, 4H). $^{13}$C-NMR (100 MHz, DMSO-d$_6$): δ 169.0, 166.0, 144.0, 132.4, 131.4, 131.1, 131.0, 130.7, 130.1, 128.7, 128.4, 128.1, 127.2, 104.6, 66.3, 49.4. ESI-HRMS: calc. for C$_{20}$H$_{16}$Cl$_2$N$_2$O$_3$: [M+H]$^+$=m/z 403.0611, found: [M+H]$^+$=m/z 403.0618.

1-(3,4-Dichloro-phenyl)-3-morpholin-4-yl-4-(4-trifluoromethyl-phenyl)-pyrrole-2,5-dione (7g): The title compound was synthesized from 3-chloro-1-(3,4-dichloro-phenyl)-4-(4-trifluoromethyl-phenyl)-pyrrole-2,5-dione (6g) (0.40 g, 0.95 mmol) and morpholine according to general procedure H and isolated as a yellow-orange solid (0.45 g, 64%). $^1$H-NMR (400 MHz, DMSO-d$_6$): δ 7.78 (m, 4H), 7.61 (d, J=7.9 Hz, 2H), 7.43 (d, J=7.3 Hz, 1H), 3.66 (t, J=4.0 Hz, 4H), 3.54 (t, J=3.8 Hz, 4H). $^{13}$C-NMR (100 MHz, CD$_3$CN): δ 168.6, 165.8, 144.6, 135.3, 131.9, 131.8, 130.8, 130.6, 130.5, 128.0, 126.1, 124.8 (q, J=3.9 Hz), 117.3, 102.8, 66.2, 49.4. ESI-HRMS: calc. for C$_{21}$H$_{15}$Cl$_2$F$_3$N$_2$O$_3$: [M+H]$^+$=m/z 471.0485, found: [M+H]$^+$=m/z 471.0494.

3,4-Dibromo-1-(3,4-dichlorophenyl)-1H-pyrrole-2,5-dione (8a): Maleic anhydride (2.0 g, 20 mmol), aluminum(III) chloride (68 mg, 0.51 mmol) and bromine (2.1 mL, 41 mmol) were placed in a sealed reaction vessel and heated to 120° C. for 16 h. After cooling to RT, the reaction was diluted with EtOAc (30 mL) and filtered. The filtrate was then concentrated in vacuo to yield the crude product, 3,4-dibromofuran-2,5-dione, as an orange solid which was used in the next step without further purification. The 3,4-dibromofuran-2,5-dione (1.0 g, 3.9 mmol) was placed in a round-bottomed flask and dissolved in glacial acetic acid (10 mL) at RT. 3.4-Dichloroaniline (0.70 g, 4.3 mmol) was added at RT and then the reaction was heated at reflux for 3 h (120-130° C.). The reaction was then cooled to RT and volatiles were removed in vacuo. The crude product was recrystallized from MeOH to yield the title compound as a reddish-brown solid (1.3 g, 80%). $^1$H-NMR (400 MHz, DMSO-d$_6$): δ 7.80 (d, J=8.6 Hz, 1H), 7.69 (d, J=1.6 Hz, 1H), 7.42 (dd, J=1.8 Hz, 6.8 Hz, 1H). $^{13}$C-NMR (100 MHz, DMSO-d$_6$): δ 162.9, 131.3, 131.2, 131.1, 129.9, 128.7, 127.3.

1-(3,4-Dichlorophenyl)-3,4-diiodo-1H-pyrrole-2,5-dione (8b): 3,4-dibromo-1-(3,4-dichlorophenyl)-1H-pyrrole-2,5-dione (8a) (0.50 g, 1.3 mmol) was placed in a round-bottomed flask and dissolved in glacial acetic acid (10 mL) at RT. Sodium iodide (0.56 g, 3.8 mmol) was added and the reaction was heated to reflux for 2 h. When the reaction was complete as evidenced by TLC, it was cooled to RT, diluted with water (20 mL) and filtered.

The filter cake was washed with water (3×10 mL), dissolved in EtOAc (30 mL), washed again with a 10% aqueous solution of sodium thiosulfate (15 mL), then water (10 mL) and brine (10 mL), dried with anhydrous $Na_2SO_4$, filtered and concentrated in vacuo. The title compound was obtained as an orange solid (0.55 g, 89%) and did not require further purification. $^1$H-NMR (400 MHz, $CDCl_3$): δ 7.54 (m, 2H), 7.26 (dd, J=6.2 Hz, 2.5 Hz, 1H). $^{13}$C-NMR (100 MHz, $CDCl_3$): δ 164.7, 133.2, 132.6, 130.8, 130.6, 127.5, 124.8, 118.0. ESI-HRMS: calc. for $C_{10}H_3Cl_2I_2NO_2$: [M+H]$^+$=m/z 493.7703, found: [M+H]$^+$=m/z 493.7707.

3-Bromo-1-(3,4-dichlorophenyl)-4-morpholino-1H-pyrrole-2,5-dione (9a): The title compound was synthesized from 3,4-dibromo-1-(3,4-dichlorophenyl)-1H-pyrrole-2,5-dione (8a) (0.10 g, 0.25 mmol) and morpholine according to general procedure C and isolated as a yellow solid (39 mg, 38%). $^1$H-NMR (400 MHz, DMSO-$d_6$): δ 7.76 (d, J=8.7 Hz, 1H), 7.67 (d, J=2.3 Hz, 1H), 7.38 (dd, J=2.3 Hz, 6.3 Hz, 1H), 3.95 (t, J=4.4 Hz, 4H), 3.75 (t, J=4.7 Hz, 4H). $^{13}$C-NMR (100 MHz, DMSO-$d_6$): δ 165.1, 164.4, 145.2, 132.1, 131.4, 131.2, 130.6, 128.9, 127.4, 81.7, 66.8, 48.9. ESI-HRMS: calc. for $C_{14}H_{11}BrCl_2N_2O_3$: [M+H]$^+$=m/z 404.9403, found: [M+H]$^+$=m/z 404.8420.

1-(3,4-Dichlorophenyl)-3-iodo-4-morpholino-1H-pyrrole-2,5-dione (9b): The title compound was synthesized from 1-(3,4-dichlorophenyl)-3,4-diiodo-1H-pyrrole-2,5-dione (8b) (0.10 g, 0.20 mmol) and morpholine according to general procedure C and isolated as a yellow solid (66 mg, 72%). $^1$H-NMR (400 MHz, DMSO-$d_6$): δ 7.75 (d, J=8.6 Hz, 1H), 7.65 (d, J=2.1 Hz, 1H), 7.36 (dd, J=2.1 Hz, 6.5 Hz, 1H), 3.96 (t, J=4.2 Hz, 4H), 3.74 (t, J=4.6 Hz, 4H). $^{13}$C-NMR (100 MHz, DMSO-$d_6$): δ 166.4, 164.8, 149.7, 132.1, 131.0, 130.7, 130.1, 128.4, 126.9, 66.4, 54.3, 48.8. ESI-HRMS: calc. for $C_{14}H_{11}Cl_2IN_2O_3$: [M+H]$^+$=m/z 452.9264, found: [M+H]$^+$=m/z 452.9252.

1-(3,4-dichlorophenyl)-3-((2-(dimethylamino)ethyl) thio)-4-(4-methoxyphenyl)-1H-pyrrole-2,5-dione (MMP-1-60). 3-Chloro-1-(3,4-dichloro-phenyl)-4-(4-methoxy-phenyl)-pyrrole-2,5-dione (6a) (100 mg, 0.26 mmol), 2-Dimethylamino-ethanethiol hydrochloride (45 mg, 0.31 mmol) and potassium carbonate (138 mg, 1.00 mmol) were stirred in 5 mL of THF for 20 h. After this time solvent was evaporated, and compound purified first by chromatography on silica gel and then re-purified by preparative HPLC. Product (62 mg, 43%) was obtained as TFA salt, as a yellow solid. $^1$H-NMR (400 MHz, DMSO-$d_6$): δ 10.19 (bs, 1H), 7.82 (d, J=8.4 Hz, 1H), 7.76 (d, J=2.4 Hz, 1H), 7.70 (d, J=8.8 Hz, 2H), 7.48 (dd, J=8.8 Hz, J=2.4 Hz, 1H), 7.12 (d, J=8.8 Hz, 2H), 3.84 (s, 3H), 3.60 (m, 2H), 3.40 (m, 2H) 2.95 (s, 6H). $^{13}$C-NMR (100 MHz, DMSO-$d_6$): δ 166.9, 166.2, 160.8, 136.4, 132.2, 131.7, 131.6, 131.2, 130.9, 130.5, 128.5, 127.1, 120.7, 114.2, 56.3, 55.5, 42.4, 25.4.

3-((2-aminoethyl)thio)-1-(3,4-dichlorophenyl)-4-(4-methoxyphenyl)-1H-pyrrole-2,5-dione (MMP-1-75). 3-chloro-1-(3,4-dichlorophenyl)-4-(4-methoxyphenyl)-1H-pyrrole-2,5-dione (6a) (0.190 g, 0.5 mmol), tert-butyl (2-mercaptoethyl)carbamate (0.177 g, 1 mmol), anhydrous potassium carbonate (0.138 g, 1 mmol) and 4 mL of THF were stirred at room temperature overnight. Solvents were removed under reduced pressure and the residue was dissolved in methylene chloride and extracted twice with water and once with brine. Organic phase was dried with sodium sulfate. Residue after evaporation of solvent was dissolved in 5 mL of methylene chloride, 5 mL of TFA was added and solution was stirred for 2 h. Solvents were evaporated, residue dissolved in methylene chloride, extracted with sodium bicarbonate, water and brine. Organic phase was dried with sodium sulfate and residue, after evaporation of solvents, was chromatographed on silica gel using hexane and ethyl acetate as eluents (2:1). The compound was further purified by preparative HPLC to afford 106 mg (41%) of 3-((2-aminoethyl)thio)-1-(3,4-dichlorophenyl)-4-(4-methoxyphenyl)-1H-pyrrole-2,5-dione TFA salt (MMP-1-75) as a yellow solid. $^1$H-NMR (400 MHz, DMSO-$d_6$): δ 8.03 (bs, 3H), 7.82 (d, J=8.4 Hz, 1H), 7.77 (d, J=2.0 Hz, 1H), 7.72 (d, J=8.8 Hz, 2H), 7.48 (dd, J=8.8 Hz, J=2.0 Hz, 1H), 7.13 (d, J=8.8 Hz, 2H), 3.85 (s, 3H), 3.54 (m, 2H), 3.16 (m, 2H). $^{13}$C-NMR (100 MHz, DMSO-$d_6$): δ 167.3, 166.6, 161.1, 136.1, 133.1, 132.1, 131.9, 131.5, 131.3, 130.8, 129.0, 127.5, 121.2, 114.5, 55.5, 39.9, 29.1

1-(3,4-dichlorophenyl)-3-(3,4-dimethoxyphenyl)-4-((2-(dimethylamino)ethyl)thio)-1H-pyrrole-2,5-dione (MMP-1-77). 3-chloro-1-(3,4-dichlorophenyl)-4-(3,4-dimethoxyphenyl)-1H-pyrrole-2,5-dione (6d) (0.206 g, 0.5 mmol), 2-(dimethylamino)ethane-1-thiol hydrochloride (0.142 g, 6 mmol), anhydrous potassium carbonate (0.138 g, 1 mmol) and 4 mL of THF were stirred at room temperature overnight. Solvents were removed under reduced pressure and the residue was chromatographed on silica gel using hexane and ethyl acetate as eluents (3:1). The compound was further purified by preparative HPLC to afford 96 mg (33%) of 1-(3,4-dichlorophenyl)-3-(3,4-dimethoxyphenyl)-4-((2-(dimethylamino)ethyl)thio)-1H-pyrrole-2,5-dione TFA salt (MMP-1-77) as yellow solid. $^1$H-NMR (400 MHz, DMSO-$d_6$): δ 10.5 (bs, 1H), 7.82 (d, J=8.8 Hz, 1H), 7.77 (d, J=2.4 Hz, 1H), 7.49 (dd, J=8.4 Hz, J=2.4 Hz, 1H), 7.35 (m, 2H), 7.15 (d, J=8.8 Hz, 1H), 3.84 (s, 3H), 3.80 (s, 3H), 3.63 (m, 2H), 3.41 (m, 2H) 2.78 (s, 6H). $^{13}$C-NMR (100 MHz, DMSO-$d_6$): δ 166.8, 166.1, 158.6, 158.3, 136.2, 132.3, 131.6, 131.2, 130.9, 130.5, 128.5, 127.1, 123.7, 120.8, 112.9, 111.6, 56.3, 55.7, 42.3, 25.4.

1-(3,4-dichlorophenyl)-3-((2-(dimethylamino)ethyl) thio)-4-(4-(trifluoromethyl)phenyl)-1H-pyrrole-2,5-dione (MMP-1-73). 3-chloro-1-(3,4-dichlorophenyl)-4-(4-(trifluoromethyl)phenyl)-1H-pyrrole-2,5-dione (6g) (0.209 g, 0.5 mmol), 2-(dimethylamino)ethane-1-thiol hydrochloride (0.142 g, 1 mmol), anhydrous potassium carbonate (0.138 g, 1 mmol) and 4 mL of THF were stirred at room temperature overnight. Solvents were removed under reduced pressure and the residue was chromatographed on silica gel using hexane and ethyl acetate as eluents (4:1). The compound was further purified by preparative HPLC to afford 91 mg (31%) of 11-(3,4-dichlorophenyl)-3-((2-(dimethylamino) ethyl)thio)-4-(4-(trifluoromethyl)phenyl)-1H-pyrrole-2,5-dione TFA salt (MMP-1-73) as yellow solid. $^1$H-NMR (400 MHz, DMSO-$d_6$): δ 7.97 (d, J=8.4 Hz, 2H), 7.88 (d, J=8.2 Hz, 2H), 7.86 (d, J=8.7 Hz, 1H), 7.78 (d, J=2.4 Hz, 1H), 7.51 (dd, J=8.6 Hz, J=2.3 Hz, 1H), 3.68 (m, 2H), 3.42 (m, 2H) 2.78 (s, 6H). $^{13}$C-NMR (100 MHz, DMSO-$d_6$): δ 166.6, 166.0, 134.6, 131.8, 131.6, 131.4, 131.1, 130.8, 128.9, 127.4, 125.8, 56.6, 42.8, 25.7.

3-((2-aminoethyl)thio)-1-(3,4-dichlorophenyl)-4-morpholino-1H-pyrrole-2,5-dione (MMP-1-14). 1-(3,4-Dichlorophenyl)-3-chloro-4-morpholino-1H-pyrrole-2,5-dione (RI-1) (0.190 g, 0.5 mmol), tert-butyl (2-mercaptoethyl) carbamate (0.177 g, 1 mmol), anhydrous potassium carbonate (0.138 g, 1 mmol) and 4 mL of THF were stirred at room temperature overnight. Solvents were removed under reduced pressure and the residue was dissolved in methylene chloride and extracted twice with water and once with brine, organic phase was dried with sodium sulfate. Residue was dissolved in 5 mL of methylene chloride, 5 mL of TFA was added and solution was stirred for 2 h. Solvents were evaporated, residue dissolved in methylene chloride, extracted with sodium bicarbonate, water and brine. Organic phase was dried with sodium sulfate and residue, after evaporation of solvents, was chromatographed on silica gel using hexane and ethyl acetate as eluents (2:1). The compound was further purified by preparative HPLC to afford 94 mg (38%) of 3-((2-aminoethyl)thio)-1-(3,4-dichlorophenyl)-4-morpholino-1H-pyrrole-2,5-dione TFA salt (MMP-1-14) as a yellow oil. $^1$H-NMR (400 MHz, DMSO-d$_6$): δ 752 (m, 2H), 7.26 (dd, J=8.4 Hz, J=2.4 Hz, 1H), 4.24 (t, J=4.8 Hz, 4H), 3.76 (t, J=4.8 Hz, 4H), 3.07 (t, J=6.0 Hz, 2H), 2.82 (t, J=6.0 Hz, 2H). $^{13}$C-NMR (100 MHz, DMSO-d$_6$): δ 171.5, 164.2, 149.8, 132.9, 132.2, 130.8, 128.1, 152.7, 89.2, 67.1, 49.3, 38.6, 34.6.

1-(3,4-dichlorophenyl)-3-((2-(dimethylamino)ethyl)thio)-4-morpholino-1H-pyrrole-2,5-dione (14-ING-9). 1-(3,4-Dichlorophenyl)-3-chloro-4-morpholino-1H-pyrrole-2,5-dione (RI-1) (0.180 g, 0.5 mmol), 2-(dimethylamino)ethane-1-thiol hydrochloride (0.142 g, 1 mmol), anhydrous potassium carbonate (0.138 g, 1 mmol) and 4 mL of THF were stirred at room temperature overnight. Solvents were removed under reduced pressure and the residue was chromatographed on silica gel using hexane and ethyl acetate as eluents (2:1). The compound was further purified by preparative HPLC to afford 63 mg (24%) of 1-(3,4-dichlorophenyl)-3-((2-(dimethylamino)ethyl)thio)-4-morpholino-1H-pyrrole-2,5-dione TFA salt (14-ING-9) as yellow solid. $^1$H-NMR (400 MHz, DMSO-d$_6$): δ 7.53 (m, 2H), 7.29 (s, 1H), 4.28 (t, J=4.6 Hz, 4H), 3.86 (t, J=4.6 Hz, 4H), 3.41 (m, 2H), 3.05 (m, 2H), 2.86 (s, 6H). $^{13}$C-NMR (100 MHz, DMSO-d$_6$): δ 169.1, 164.5, 148.6, 131.8, 130.6, 130.1, 127.7, 125.7, 92.7, 66.6, 58.2, 58.2, 48.8, 43.7, 32.2.

1-(3,4-dichlorophenyl)-3-((2-hydroxyethyl)thio)-4-morpholino-1H-pyrrole-2,5-dione (HP-1-16). 1-(3,4-Dichlorophenyl)-3-chloro-4-morpholino-1H-pyrrole-2,5-dione (RI-1) (0.15 g, 0.41 mmol) was placed in a round-bottomed flask and dissolved in THF (5 mL) at room temperature. 2-Mercaptoethanol (58 µL, 0.83 mmol) was added and the reaction was stirred at room temperature overnight. After reaction was complete as evidenced by TLC, it was diluted with water (20 mL) and the organic products were extracted with methylene chloride. The combined organic extracts were dried with anhydrous sodium sulfate. The crude product was then purified by preparative HPLC to afford 57 mg (34%) of 1-(3,4-dichlorophenyl)-3-((2-hydroxyethyl)thio)-4-morpholino-1H-pyrrole-2,5-dione (HP-1-16) as yellow oil. $^1$H-NMR (400 MHz, CDCl$_3$): δ 7.51 (m, 2H), 7.24 (m, 1H), 4.32 (t, J=4.6 Hz, 4H), 3.86 (t, J=4.8 Hz, 4H), 3.73 (q, J=6.1 Hz, 2H), 3.20 (t, J=6.6 Hz, 1H), 2.83 (t, J=5.6 Hz, 2H). $^{13}$C-NMR (100 MHz, DMSO-d$_6$): δ 173.5, 169.6, 153.9, 136.9, 136.2, 135.8, 135.2, 133.5, 132.0, 97.2, 71.4, 65.0, 53.6, 42.7. ESI-HRMS: calc. for $C_{16}H_{16}Cl_2N_2O_4S$: [M+H]$^+$=m/z 403.0281, found: [M+H]$^+$=m/z 403.0294.

All of the methods and apparatuses disclosed and claimed herein can be made and executed without undue experimentation in light of the present disclosure. While the compositions and methods of this invention have been described in terms of preferred embodiments, it will be apparent to those of skill in the art that variations may be applied to the methods and apparatuses and in the steps or in the sequence of steps of the methods described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 4,684,611
U.S. Pat. No. 4,873,191
U.S. Pat. No. 4,952,500
U.S. Pat. No. 5,175,384
U.S. Pat. No. 5,175,385
U.S. Pat. No. 5,187,260
U.S. Pat. No. 5,302,523
U.S. Pat. No. 5,322,783
U.S. Pat. No. 5,384,253,
U.S. Pat. No. 5,464,765
U.S. Pat. No. 5,530,179
U.S. Pat. No. 5,538,877
U.S. Pat. No. 5,538,880
U.S. Pat. No. 5,550,318
U.S. Pat. No. 5,563,055
U.S. Pat. No. 5,565,186
U.S. Pat. No. 5,580,859
U.S. Pat. No. 5,589,466
U.S. Pat. No. 5,591,616
U.S. Pat. No. 5,610,042
U.S. Pat. No. 5,612,486
U.S. Pat. No. 5,616,491
U.S. Pat. No. 5,625,125
U.S. Pat. No. 5,639,457
U.S. Pat. No. 5,656,610
U.S. Pat. No. 5,702,932
U.S. Pat. No. 5,736,524
U.S. Pat. No. 5,780,448
U.S. Pat. No. 5,789,215,
U.S. Pat. No. 5,945,100
U.S. Pat. No. 5,981,274
U.S. Pat. No. 5,994,624
Alda et al., *Clin. Cancer Res.*, 4:235-240, 1998.
Bello et al., *Biochem. Pharmacol.*, 63:1585-1588, 2002.
Bennardo, et al., *PLoS Genet.*, 4:e1000110, 2008.
Budke, et al., *Nucleic Acids Res.*, 40(15):7347-7357, 2012.
Chen et al., *J. Biol. Chem.*, 274:32931-32935, 1999.
Chen et al., *Proc. Natl. Acad. Sci. USA*, 95:5287-5292, 1998.
Connell, et al., *Int. J. Oncol.*, 28:1113-1119, 2006.
Davies et al., *Mol. Cell*, 7:273-282, 2001.
Dubernet, et al., *Tetrahedron*, 61:4585-4593, 2005.
Esashi et al., *Nature*, 434:598-604, 2005.
Han et al., *Cancer Res.*, 62:2890-2896, 2002.
*Handbook of Pharmaceutical Salts: Properties, Selection and Use*, Stahl & Wermuth (Eds.), Verlag Helvetica Chimica Acta, 2002.
Hansen et al., *Int. J. Cancer*, 105:472-479, 2003.
Henning and Sturzbecher, *Toxicology*, 193:91-109, 2003.
Hine, et al., *Proc. Nat. Acad. Sci.*, 105:20810-20815, 2008.
Ito et al., *J. Gene Med.*, 7(8):1044-1052, 2005.
Jayathilaka, et al., *Proc. Nat. Acad. Sci.*, 105:15848-15853, 2008.
Klein, H., *DNA Repair*, 7:686-693, 2008.
Lipinski, et al. *Adv. Drug Deliv. Rev.*, 46:3-26, 2001.
Liu et al., *Mol. Cell.*, 1:783-793, 1998.
Maacke et al., *Int. J. Cancer*, 88:907-913, 2000a.

Maacke et al., *J. Cancer Res. Clin. Oncol.,* 128:219-222, 2002.
Maacke et al., *Oncogene,* 19:2791-2795, 2000b.
Mansour, et al. *Nucleic Acids Res.,* 36: 4088-4098, 2008.
Matuszak, et al., *J. Med. Chem.,* 52:7410-7420, 2009.
Marcus et. al., *Cancer,* 77(4):697-670, 1996.
Moynahan et al., *Mol. Cell,* 7:263-272, 2001.
Pellegrini et al., *Nature,* 420:287-293, 2002.
Pierce, et al., *Genes Dev.,* 13:2633-2638, 1999.
Porter et al., *Br. J. Surg.,* 81:1512-1515, 1994.
Qiao et al., *Br. J. Cancer,* 93:137-143, 2005.
Raderschall et al., *Cancer Res.,* 62:219-225, 2002.
Relies and Schluenz, *J. Org. Chem.,* 37:1742-1745, 1972.
Remington's Pharmaceutical Sciences, 18th Ed. Mack Printing Company, 1289-1329, 1990.
Rubin et al., *N. Engl. J. Med.,* 335:1413-1416, 1996.
Russell et al., *Cancer Res.,* 63:7377-7383, 2003.
Shin et al., *Embo. J.,* 22:4566-4576, 2003.
Shinohara et al., *Cell,* 69:457-470, 1992.
Slupianek et al., *Mol. Cell Biol.,* 22:4189-4201, 2002.
Slupianek et al., *Mol. Cell,* 8:795-806, 2001.
Smith, et al., *JACS,* 132:1960-1965, 2010.
Stark, et al., *Mol. Cell Biol.,* 24:9305-9316, 2004.
Takata et al., *Mol. Cell Biol.,* 21:2858-2866, 2001.
Tebbs et al., *Proc. Nat. Acad. Sci.,* 92:6354-6358, 1995.
Thompson and Schild, *Mutat. Res.,* 477:131-153, 2001.
Vispe et al., *Nucleic Acids Res.,* 26:2859-2864, 1998.
Walter, et al., *Acrhiv der Pharmazie,* 337:201-206, 2004.
Wang et al., *J. Natl. Cancer Inst.,* 93:1473-1478, 2001.
Wong et al., *J. Biol. Chem.,* 272:31941-31944, 1997.
Xu, et al., *Letters in Drug Design & Discovery,* 6:51-55, 2009.
Yuan et al., *Cancer Res.,* 59:3547-3551, 1999.

The invention claimed is:

1. A method for inhibiting RAD51 protein in a cell comprising providing to the cell an effective amount of a RAD51 protein inhibitor, wherein the RAD51 inhibitor is the compound of the formula:

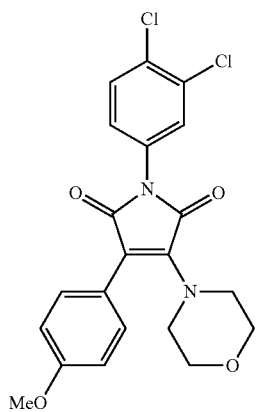

or a salt thereof.

2. A method for inhibiting RAD51 protein in a cell comprising providing to the cell an effective amount of a RAD51 protein inhibitor, wherein the RAD51 inhibitor is the compound of the formula:

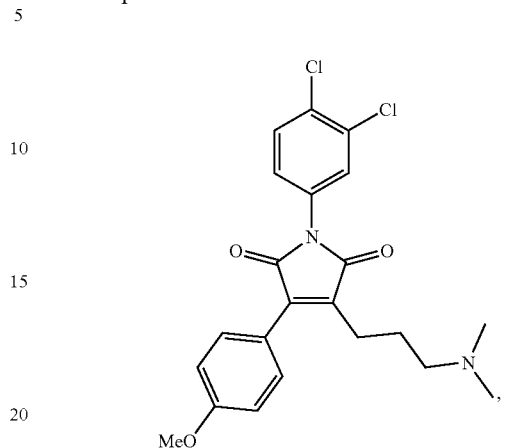

or a salt thereof.

3. The method of claim 1, wherein the cell is a cancer cell.
4. The method of claim 3, wherein the cancer cell is resistant to chemotherapy or radiation.
5. The method of claim 4, wherein the cancer cell is in a patient.
6. The method of claim 5, wherein the patient has a chemotherapy- or radiation-resistant cancer.
7. The method of claim 1, wherein the cell has been treated or will be treated with a DNA damaging agent.
8. The method of claim 7, wherein the DNA damaging agent is a cross linking agent, an alkylating agent, nitrosourea, anti-metabolite, plant alkaloid, plant extract, or radioisotope.
9. The method of claim 7, wherein the DNA damaging agent is actinomycin, amsacrine, anthracyclines, bleomycin, busulfan, camptothecin, carboplatin, chlorambucil, cisplatin, cyclophosphamide, cytoxan, dactinomycin, daunorubicin, docetaxel, doxorubicin, epirubicin, hexamethylmelamineoxaliplatin, iphosphamide, melphalan, merchlorethamine, mitomycin, mitoxantrone, nitrosourea, paclitaxel, plicamycin, procarbazine, teniposide, triethylenethiophosphoramide or etoposide (VP16).
10. The method of claim 7, wherein the agent generates inter-strand DNA crosslinks (ICL).
11. The method of claim 10, wherein ICL-generating agent is mytomycin C.
12. The method of claim 2, wherein the cell is a cancer cell.
13. The method of claim 12, wherein the cancer cell is resistant to chemotherapy or radiation.
14. The method of claim 13, wherein the cancer cell is in a patient.
15. The method of claim 14, wherein the patient has a chemotherapy- or radiation-resistant cancer.
16. The method of claim 2, wherein the cell has been treated or will be treated with a DNA damaging agent.
17. The method of claim 16, wherein the DNA damaging agent is a cross linking agent, an alkylating agent, nitrosourea, anti-metabolite, plant alkaloid, plant extract, or radioisotope.
18. The method of claim 16, wherein the DNA damaging agent is actinomycin, amsacrine, anthracyclines, bleomycin, busulfan, camptothecin, carboplatin, chlorambucil, cisplatin, cyclophosphamide, cytoxan, dactinomycin, daunorubicin, docetaxel, doxorubicin, epirubicin, hexamethylmelamineoxaliplatin, iphosphamide, melphalan, merchlorethamine, mitomycin, mitoxantrone, nitrosourea, paclitaxel, plicamycin, procarbazine, teniposide, triethylenethiophosphoramide or etoposide (VP16).

19. The method of claim 16, wherein the agent generates inter-strand DNA crosslinks (ICL).

20. The method of claim 19, wherein ICL-generating agent is mytomycin C.

* * * * *

UNITED STATES PATENT AND TRADEMARK OFFICE
CERTIFICATE OF CORRECTION

PATENT NO. : 10,912,761 B2  
APPLICATION NO. : 14/648115  
DATED : February 9, 2021  
INVENTOR(S) : Philip P. Connell et al.

Page 1 of 1

It is certified that error appears in the above-identified patent and that said Letters Patent is hereby corrected as shown below:

In the Claims

In Claim 2, on Column 50, Line 7, the compound formula should read as follows:

" 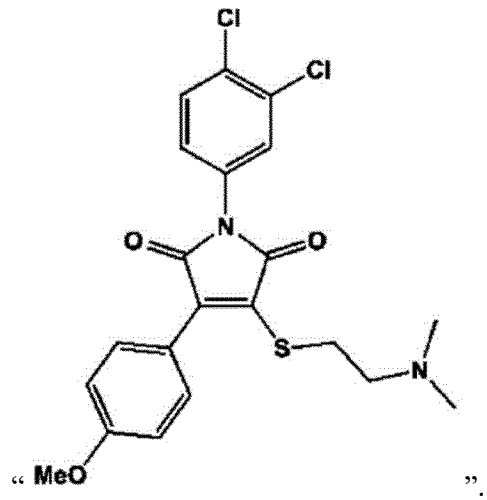 ".

Signed and Sealed this  
Sixteenth Day of March, 2021

Drew Hirshfeld  
*Performing the Functions and Duties of the  
Under Secretary of Commerce for Intellectual Property and  
Director of the United States Patent and Trademark Office*